US006355419B1

(12) United States Patent
Alfenito

(10) Patent No.: US 6,355,419 B1
(45) Date of Patent: *Mar. 12, 2002

(54) PREPARATION OF POOLS OF NUCLEIC ACIDS BASED ON REPRESENTATION IN A SAMPLE

(75) Inventor: Mark R. Alfenito, Redwood City, CA (US)

(73) Assignee: Hyseq, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/067,317

(22) Filed: Apr. 27, 1998

(51) Int. Cl.[7] ............................. C12Q 1/68; G01N 1/00; G01N 15/00
(52) U.S. Cl. ........................ 435/6; 435/183.1; 422/50; 422/68.1
(58) Field of Search ...................... 435/6, 69.1, 183.1, 435/810; 422/50, 68.1; 436/501; 935/77, 78

(56) References Cited

U.S. PATENT DOCUMENTS

| | | | |
|---|---|---|---|
| 4,302,204 A | 11/1981 | Wahl et al. | 23/230.3 |
| 4,562,159 A | 12/1985 | Shafritz | 436/501 |
| 4,591,567 A | 5/1986 | Britten et al. | 435/293 |
| 4,613,566 A | 9/1986 | Potter | 435/6 |
| 4,675,283 A | 6/1987 | Roninson | 435/6 |
| 4,677,054 A | 6/1987 | White et al. | 435/6 |
| 4,731,325 A | 3/1988 | Palva et al. | 435/6 |
| 4,766,062 A | 8/1988 | Diamond et al. | 435/6 |
| 4,806,546 A | 2/1989 | Carrico et al. | 536/27 |
| 4,806,631 A | 2/1989 | Carrico et al. | 536/27 |
| 4,849,334 A | 7/1989 | Lorinez | 435/5 |
| 4,883,761 A | 11/1989 | Keith et al. | 435/320 |
| 4,916,056 A | 4/1990 | Brown, III et al. | 435/7 |
| 4,981,783 A | 1/1991 | Augenlicht | 435/6 |
| 4,988,617 A | 1/1991 | Landegren et al. | 435/6 |
| 5,002,867 A | 3/1991 | Macevicz | 435/6 |
| 5,008,080 A | 4/1991 | Brown, III et al. | 422/56 |
| 5,143,854 A | 9/1992 | Pirrung et al. | 436/518 |
| 5,160,701 A | 11/1992 | Brown, III et al. | 422/56 |
| 5,202,231 A | 4/1993 | Drmanac et al. | 435/6 |
| 5,242,794 A | 9/1993 | Whiteley et al. | 435/6 |
| 5,310,893 A | 5/1994 | Erlich et al. | 536/24.31 |
| 5,348,855 A | 9/1994 | Dattagupta et al. | 435/6 |
| 5,354,657 A | 10/1994 | Höltke et al. | 435/6 |
| 5,405,783 A | 4/1995 | Pirrung et al. | 436/518 |
| 5,424,186 A | 6/1995 | Fodor et al. | 435/6 |

(List continued on next page.)

FOREIGN PATENT DOCUMENTS

| | | |
|---|---|---|
| EP | 0 197 266 B1 | 10/1986 |
| EP | 0 202 758 A1 | 11/1986 |
| EP | 0 228 075 A2 | 7/1987 |
| EP | 0 235 726 A3 | 9/1987 |
| EP | 0 237 362 B1 | 9/1987 |
| EP | 0 373 203 B1 | 6/1990 |
| EP | 0 721 016 A2 | 7/1996 |
| WO | WO 85/01051 | 3/1985 |
| WO | WO 86/03782 | 7/1986 |
| WO | WO 88/01302 | 2/1988 |
| WO | WO 88/10313 | 12/1988 |
| WO | WO 89/10977 | 11/1989 |
| WO | WO 89/11548 | 11/1989 |
| WO | WO 90/03382 | 4/1990 |
| WO | WO 90/04652 | 5/1990 |
| WO | WO 92/10588 | 6/1992 |
| WO | WO 94/11530 | 5/1994 |
| WO | WO 94/27719 | 12/1994 |
| WO | WO 96/31622 | 10/1996 |
| WO | WO 96/29212 | 8/1997 |
| YU | 18617/87—P-570/87 | 2/1988 |

OTHER PUBLICATIONS

Angelini, G., De Preval, C., Gorski, J., and Mach, B., (1986), "High–Resolution Analysis of the Human HLA–DR Polymorphism by Hybridization with Sequence–Specific Oligonucleotide Probes," Proc. Natl. Acad. Sci. USA, 83, 4489–4493.

Bains W., and Smith, G.C., (1988), "A Novel Method for Nucleic Acid Sequence Determination," Journal of Theoretical Biology, 135: 303–307.

Beltz, G.A., Jacobs, K.A., Eickbush, T.H., Cherbas, P.T., and Kafatos, F.C., (1983), "Isolation of Multigene Families and Determination of Homologies by Filter Hybridization Methods," Methods in Enzymology, 100(19), 266–285.

Besmer, P., Miller Jr. , R.C. , Caruthers, M.H., Kumar, A., Minamoto, K., Van De Sande, J.H., Sidarova, N., and Khorana, H.G., (1972), "Hybridization of Polydeoxynucleotides with Tyrosine Transfer RNA Sequences to the r–Strand of ø80psu$^{+III}$ DNA," J. Mol. Biol., 72, 503–522.

Breslauer, K.J., Frank, R., Blocker, H., and Marky, L.A., (1986), "Predicting DNA Duplex Stability from the Base Sequence," Proc. Natl. Acad. Sci., 83, 3746–3750.

(List continued on next page.)

Primary Examiner—Ardin H. Marschel
(74) Attorney, Agent, or Firm—Marshall, Gerstein & Borun

(57) ABSTRACT

The invention relates to methods for preparing nucleic acid pools useful in hybridization studies. Such methods allow hybridization conditions, such as time, temperature, ionic strength, etc., to be adjusted to increase the likelihood that hybridization to the nucleic acids within each pool is within the linear range of detection (i.e., detectable but not saturating). The methods rely on pooling nucleic acids derived from a sample, based on the degree of representation within the sample, i.e., nucleic acids having similar degrees of representation within in a sample are combined into a pool. The invention also provides arrays and kits produced from pooled nucleic acids, and an improved method for identifying a nucleic acid and/or its representation in a sample.

10 Claims, No Drawings

U.S. PATENT DOCUMENTS

| | | | |
|---|---|---|---|
| 5,436,327 A | 7/1995 | Southern et al. | 536/25.34 |
| 5,445,934 A | 8/1995 | Fodor et al. | 435/6 |
| 5,525,464 A | 6/1996 | Drmanac et al. | 435/6 |
| 5,545,531 A | 8/1996 | Rava et al. | 435/6 |
| 5,800,992 A * | 9/1998 | Fodor et al. | 435/6 |

OTHER PUBLICATIONS

Bugawan, T.L., Horn, G.t., Long, C.M., Mickelson, E., Hansen, J.A., Ferrara, G.B., Angeline, G., and Erlich, H.A., (1988), "Analysis of HLA–DP allelic Sequence Polymorphism Using the in Vitro Enzymatic DNA Amplification of DP–α and DP–β Loci," Journal of Immunology, 141 (12), 4024–4030.

Chetverin, Alexander B., Kramer, Fred R., (1994), "Oligonucleotide Arrays: New concepts and Possibilities," Bio/Technology, vol. 12, 1093–1099.

Church, G.M., and Gilbert, W., (1984), "Genomic Sequencing,", Proc. Natl. Acad. Sci., 81, 1991–1995.

Conner, B.J., Reyes, A.A., Morin, C., Itakura, K., Teplitz, R.L., and Wallace, R.B., (1983), "Detection of Sickle Cell $\beta^s$ – globin Allele by Hybridization with Synthetic Oligonucleotides," Proc. Natl. Acad. Sci. USA, 80, 278–282.

Craig, A., Michiels, F., Zehetner, G., Sproat, B., Burmeister, M., Bucan, M., Poustka, A., Pohl, T., Frischauf, A.M., Lehrach, H., (1987), "Molecular Techniques in Mammalian Genetics: A New Era in Genetic Analysis," Human Genetics, pp. 126–132.

Craig, A.G., Nizetic, D., Hoheisel, J.D., Zehetner, G., and Lehrach, H. (1990). "Ordering of cosmid clones covering the herpes simplex virus type I (HSV–I) genome: a test case for fingerprinting by hybridisation." Nucleic Acids Res, (18)(9), 2653–60.

Crkvenjakov, R., Bucan, M., Konstantinovic, M., Fogel, M., Savic, A., and Glisin, V., (1984), "Characterization of Two Rat Globin cDNA Clones," Hemoglobin, 8(6), 597–611.

Drmanac, R., Labat, I., Brukner, I., and Crkvenjakov, R. (1989). "Sequencing of megabase plus DNA by hybridization: theory of the method." Genomics, 4(2), 114–28.

Drmanac, R., Labat, I., Strezoska, Z., and Crkvenjakov, R. (1989). "An alternative large DNA sequencing method: the theoretical and informational feasability of sequencing by hybridization." Abstracts of papers presented at the 1989 meeting on Genome Mapping and Sequencing: Apr. 26–30, 1989, C. Cantor, M. Olson, and R. Roberts, eds., Cold Spring Harbor Laboratory, Cold Spring Harbor, 44.

Drmanac, R., Lennon, G., Drmanac, S., Labat, I., Crkvenjakov, R., and Lehrach, H. (1990). "Partial sequencing by oligo–hybridization: concept and applications in genome analysis." The First International Conference on Electrophoresis, Supercomputing and the Human Genome, C. Cantor and H. Lim, eds., World Scientific, Singapore, 60–74.

Drmanac, R., Drmanac, S., Labat, I., Stavropoulos, N., (1994), "Requirements in Screening cDNA Libraries For New Genes and Solutions Offered by SBH Technology," Plenum Press, 239–249.

Gillam, S., Waterman, K., and Smith, M. (1975). "The base–pairing specificity of cellulose–pdT9." Nucleic Acids Res, 2(5), 625–34.

Gorski, J., Tilanus, M., Giphart, M., and Mach, B., (1987), "Oligonucleotide Genotyping Shows that Alleles at the HLA–DR III Locus of the DRw52 Supertypic Group Segregate Independently of Known DR or Dw Specificities," Immunogenetics, 25, 79–83.

Gusev, V.D., Kulichkov, V.A., and Titkova, T.N., (1980), "Analysis of Genetic Texts. I. 1–Gram Characteristics," Emperical Prediction and Recognition of Patterns, 83, 11–33.

Hobden, A.N., Read, M.J., Dykes, C.W., and Harford S., (1985), "M13 Clones Carrying Point Mutations: Identification by Solution Hybridization," Analytical Biochemistry, 144, 75–78.

Ikuta, S., Takagi, K., Wallace, R.B., and Itakura, K., (1987), "Dissociation Kinetics of 19 Base Paired Oligonucleotide–DNA Duplexes Containing Different Single Mismatched Base Pairs," Nucleic Acids Research, 15(2) 797–811.

Khrapko, K. R., Lysov Yu, P., Khorlin, A. A., Shick, V. V., Florentiev, V. L., and Mirzabekov, A. D. (1989). "An oligonucleotide hybridization approach to DNA sequencing." FEBS Lett, 256(1–2), 118–22.

Khrapko, K.R., Lysov, Yu.P., Khorlin, A.A., Ivanov, I.B., Yershov, G.M., Vasilenko, S.K., Florentiev, V.L., and Mirzabekov, A.D., (1991), "A Method for DNA Sequencing by Hybridization with Oligonucleotide Matrix," J. DNA Sequencing and Mapping, 1:375–388.

Kohara, Y., Akiyama, K., and Isono, K., (Jul. 31, 1987), "The Physical Map of the Whole E. coli Chromosome: Application of a New Strategy for Rapid Analysis and Sorting of a Large Genomic Library," 50, 495–508.

Labat, I., (1988), "Subfragements as an Informative Characteristic of the DNA Molecule–Computer Simulation," Research Report, pp1–33.

Landry, M.D., M.L., Fong, Ph.D., C.K.Y., (1985), "Nucleic Acid Hybridization in the Diagnosis of Viral Infections," Clinics in Laboratory Medicine, 5(3), 513–529.

Latham, T., and Smith, F. I. (1989). "Detection of single–base mutations in DNA molecules using the solution melting method." DNA, 8(3), 223–31.

Lehrach, H., Drmanac, R., Hoheisel, J., Larin, Z., Lennon, G., Nizetic, D., Monaco, T., Zehetner, G., and Poustka, A. (1990). "Hybridization fingerprinting in genome mapping and sequencing." Genome Analysis I, Genetic and Physical Mapping, Cold Spring Harbor, 39–81.

Lehrach, H., Zehetner, G., Nicetic, D., Craig, A., Michiels, F., (1988), "Oligonucleotide fingerprinting, A Parallel Approach to Establish Ordered Clone Libraries," Abstracts and Papers presented at the 1988 meeting on Genome Mapping and Sequencing, p. 11.

Lysov Iu, P., Florent'ev, V. L., Khorlin, A. A., Khrapko, K. R., and Shik, V. V. (1988). "[Determination of the nucleotide sequence of DNA using hybridization with oligonucleotides. A new method]." Dokl Akad Nauk SSSR, 303(6), 1508–11.

Matthews, J. A., and Kricka, L. J. (1988). "Analytical strategies for the use of DNA probes." Analytical Biochem, 169(1), 1–25.

Meinkoth, J., and Wahl, G. (1984). "Hybridization of nucleic acids immobilized on solid supports." Anal Biochem, 138(2), 267–84.

Michiels, F., Craig, A.G., Zehetner, G., Smith, G.P., and Lehrach, H., (1987), "Molecular Approaches to Genome Analysis: A Strategy for the Construction of Ordered Overlapping Clone Libraries," Cabios: Molecular Analysis of Genetic Distances, 3(3), 203–210.

Poustka, A., Phol, T., Barlow, D.P., Zehetner, G., Craig, A., Michiels, F., Ehrich, E., Frischauf, A.M., and Lehrach, H., (1986), "Molecular Approaches to Mammalian Genetics," Cold Spring Harbor Symposia on Quantitative Biology, LI, 131–139.

Reyes et al., (1984), "Use of Synthetic Oligonucleotide Hybridization Probes for the Characterization and Isolation of Cloned DNA's," Genetic Engineering, Principles and Methods, vol. 6, pp. 157–173.

Saiki, R.K., Bugawan, T.L., Horn, G.T., Mullis, K.B., and Erlich, H.A., (1986), "Analysis of Enzymatically Amplified β–Globin and HLA–DQ α DNA with Allele–Specific Oligonucleotide Probes," Letters to Nature, 324, 163–166.

Saiki, R.K., Scharf, S., Faloona, F., Mullis, K.B., Horn, G.T., Erlich, H.A., Arnheim, N., (1985), "Enzymatic Amplification of β–Globin Genomic Sequences and Restriction Site Analysis for Diagnosis of Sickle Cell Anemia," Science: Research Article, 230, 1350–1354.

Sambrook, J., Fritsch, E.F., and Maniatis, T., (1989) "Molecular Cloning: A Laboratory Manual," Cold Spring Harbor Laboratory Press, Second Edition, 5.80, 7.58–7.78.

Scharf, S.J., Friedmann, A., Brautbar, C., Szafer, F., Steinman, L., Horn, G., Gyllensten, U., and Erlich, H.A., (1988), "HLA Class II Allelic Variation and Susceptibility to *Pemphigus Vulgaris,*" Proceedings of Natl. Academy of Science, 85, 3504–3508.

Schildkraut, C.L., Marmur, J., and Doty, P., (1961), "The Formation of Hybrid DNA Moleculres and Their Use in Studies of DNA Homologies," J. Mol. Biol., 8, 595–617.

Sim, G.K., Kafatos, F.C., Jones, C.W., and Koehler, M.D., (1979), "Use of a cDNA Library for Studies on Evolution and Developmental Expression of the Chorion Multigene Families," Cell, pp. 1303–1316.

Stein, S.K., (1961), "The Mathematician as an Explorer," Scientific American, 204, 149–158.

Suggs, S.V., Wallace, R.B., Hirose, T., Kawashima, E.H., and Itakura, K., (1981), "Use of Synthetic Oligonucleotides as Hybridization Probes: Isolation of Cloned cDNA Sequences for Human $β_2$–Microglobulin," Proc. Natl. Acad. Sci. USA, 78(11) 6613–6617.

Syvanen, A.C., (1986), "Nucleic Acid Hybridization: From Research Tool to Routine Diagnostic Method," Review Article, Medical Biology, 64, 313–324.

Termijtelen, A., Gorski, J., Robbins, F.M., Tanigaki, N., Tosi, R., Tilanus, M.G.J., Schroeijers, W.E.M., and Van Rood, J.j., (1988), "Correlations Between Polymorphisms at the DNA and at the Protein Level of Drw52 Haplotypes, Revealed with a Variety of Techniques," Human Immunology, 22, 171–178.

Thein, S.L., and Wallace, R.B., (1986), "The Use of Synthetic Oligonucleotides as Specific Hybridization Probes in the Diagnosis of Genetic Disorders," Human Genetic Diseases: A Practical Approach, Ch. 3, 33–50.

Tiercy, J.M., Gorski, J., Jeannet M., Mach, B., (1988), "Identification and Distribution of Three Serologically Undetetected Alleles of HLA–DR by Oligonucleotide DNA Typing Analysis," Proc. Natl. Acad. Sci. USA, 85, 198–202.

Ucla, C., Van Rood, J.J., Gorski, J., and Mach, B., (Oct. 1987), "Analysis of HLA–D Micropolymorphism by a Simple Procedure: RNA Oligonucleotide Hybridization," J. Clin. Invest., 80, 1155–1159.

Wallace, R.B., Johnson, M.J., Hirose, T., Miyake, T., Kawashima, E.H., and Itakura, K., (1981), "The Use of Synthetic Oligonucleotides as Hybridization Probes, II. Hybridization of Oligonucleotides of Mixed Sequence to Rabbit β–Globin DNA," Nucleic Acids Research, 9(4) 879–894.

Wallace, R.B., Shaffer, J., Murphy, R.F., Bonner, J., Hirose, T., and Itakura, K., (1979), "Hybridization of Synthetic Oligodeoxyribonucleotides to $Ø_x$ 174 DNA: The Effect of Single Base Pair Mismatch," Nucleic Acids Research, 6(11) 3543–3557.

Wallace et al., (1987), "Oligonucleotide Probes for the Screening of Recombinant DNA Libraries" Methods in Enzymology, vol. 152, pp. 432–442.

Wetmur, J.G., Davidson, N., (1968), "Kinetics of Renaturation of DNA," J. Mol. Biol., 31, 349–370.

Wetmur, J.G., (1976), "Hybridization and Renaturation Kinetics of Nucleic Acids," Annual Review of Biophysics and Bioengineering, 5, 337–361.

Wood, W.I., Gitschier, J., Lasky, L.A., and Lawn, R.M., (1985), "Base Composition–Independent Hybridization in Tetramethylammonium Chloride: A Method for Oligonucleotide Screening of Highly Complex Gene Libraries," Proc. Natl. Acad. Sci. USA, 82, 1585–1588.

(1988), "Automation of Sanger's protocol for high thruput DNA sequencing," A poster presented at the 1988 Meeting on Genome Mapping and Sequencing, p. III.

Blanchard, A.P., Kaiser, R.J., Hood, L.E., (1996), "High–density oligonucleotide arrays," Biosensors & Bioelectronics, vol. 11., No. 617, pp. 687–690.

Blanchard, A.P., Hood, L., (1996), "Sequence to array: Probing the genome's secrets," Nature Biotechnology, vol. 14, p. 1649.

Chee, M., Yang, R., Hubbell, E., Berno, A., Huang, X.C., Stern, D., Winkler, J., Lockhart, D.J., Morris, M.S., Fodor, S.P.A., (1996), "Accessing Genetic Information with High–Density DNA Arrays," Science, vol. 274, pp. 610–614.

Church, G.M., Kieffer–Higgins, S., (1988), "Multiplex DNA Sequencing," Research Articles, pp. 185–188.

Drmanac, R., Drmanac, S., Labat, I., Crkvenjakov, R., Vicentic, A., Gemmell, A., (1992), "Sequencing by hybridization: Towards an automated sequencing of one million M13 clones arrayed on membranes," Electrophoresis, 13, 566–573.

Drmanac, R., Drmanac, S., Labat, I., Vicentic, A., Gemmell, A., Stavropoulos, N., Jarvis, J., (1993), "SBH and the Integration of Complementary Approaches in the Mapping, Sequencing, and Understanding of Complex Genomes," Second International Conference on Bioinformatics, Supercomputing and Complex Genomes, pp. 121–134.

Drmanac, R., Drmanac, S., Strezoska, Z., Paunesku, T., Labat, I., Zeremski, M., Snoddy, J., Funkhouser, W.K., Koop, B., Hood, L., Crkvenjakov, R., (1993), "DNA Sequence Determination by Hybridization: A Stategy for Efficient Large–Scale Sequencing," Science, vol. 260, pp. 1649–1652.

Drmanac, R., Nizetic, D., Lennon, G.G., Beitverda, A., Lehrach, H., (1991), "W (A or T) sequences as probes and primers suitable for genomic mapping and fingerprinting," Nucleic Acids Research, vol. 19, No. 21, pp. 5839–5842.

Drmanac, S., Stavropoulos, A., Labat, I., Vonau, J., Hauser, B., Soares, M.B., Drmanac, R., (1996), "Gene–Representing cDNA Clusters Defined by Hybridization of 57,419 Clones from Infant Brain Libraries with Short Oligonucleotide Probes," Genomics 37, pp. 29–40.

Drmanac, R., Strezoska, Z., Labat, I., Drmanac, S., Crkvenjakov, R., (1990), "Reliable Hybridization of Oligonucleotides as Short as Six Nucleotides," DNA and Cell Biology, vol. 9, No. 7, pp. 527–534.

Dubiley, S., Kirillov, E., Lysov, Y., Mirzabekov, A., (1997), "Fractionation, phosphorylation and ligation on oligonucleotide microchips to enhance sequencing by hybridization," Nucleic Acids Research, vol. 25, No. 12, pp. 2259–2265.

Evans, G.A., Lewis, K.A., (1989), "Physical mapping of complex genomes by cosmid multiplex analysis," Proc. Natl. Acad. Sci. USA, vol. 86, pp. 5030–5034.

Fodor, S.P.A., Huang, X.C., Lipshutz, R.J., (1994), "Oligonucleotide Arrays and Sequence Analysis by Hybridization," Clinical Chemistry, vol. 40, No. 4, p. 653.

Fodor, S.P.A., Lipshutz, R.J., Rava, R.P., (1994), "Oligonucleotide Arrays and Sequence Analysis by Hybridization," Abstract of Paper, 207th American Chemical Society National Meeting, San Diego, CA, Mar. 13–17, 1994.

Gingeras, T.R., Kwoh, D.Y., Davis, G.R., (1987), "Hybridization properties of immobilized nucleic acids," Nucleic Acids Research, vol. 15, No. 13, pp. 5373–5389.

Hacia, J.G., Brody, L.C., Chee, M.S., Fodor, S.P.A., Collins, F.S., (1996), "Detection of heterozygous mutation in BRCA1 using high density oligonucleotide arrays and two-color fluorescence analysis," Nature Genetics, vol. 14, pp. 441–447.

Kreiner, (1996), "Rapid genetic sequence analysis using a DNA probe array system," American Laboratory, pp. 39–43.

Lipshutz, R.J., (1994), "Oligonucleotide Arrays and Sequence Analysis by Hybridization," Clinical Chemistry, vol. 40, No. 6, p. 1173.

Lipshutz, R.J., Morris, D., Chee, M., Hubbell, E., Kozal, J.J., Shah, N., Shen, N., Yong, R., and Fodor, S.P.A., (1995), "Using Oligonucleotide Probe Arrays To Access Genetic Diversity," BioTechniques, vol. 19, No. 3, pp. 442–447.

Lockhart, D.J., Dong, H., Byrne, M.C., Follettie, M.T., Gallo, M.V., Chee, M.S., Mittmann, M., Wang, C., Kobayaski, Michiko, Horton, H., Brown, E.L., (1996), "Expression monitoring by hybridization to high–density oligonucleotide arrays," Nature BioTechnology, vol. 14, pp. 1675–1680.

Milosavlievic, A., Savkovic, S., Crkvenjakov, R., Salbego, D., Serrao, H., Kreuzer, H., Gemmell, A., Batus, S., Grujic, D., Carnahan, S., Paunesku, T., Tepavcevic, J., (1996), "DNA Sequence Recognition by Hybridization to short Oligomers: Experimental Verification of the Method on the E. coli Genome," Genomics 37, pp. 77–86.

Milosavlievic, A., Savkovic, S., Crkvenjakov, R., Salbego, D., Serrao, H., Kreuzer, H., Gemmell, A., Batus, S., Grujic, D., Carnahan, S., Tepavcevic, J., "Genome–scale DNA sequence recognition by hybridization to short oligomers," ISMB–96, pp. 176–181. (1996).

Milosavlievic, A., Strezoska, Z., Zeremski, M., Grujic, Paunesku, T., Crkvenjakov, R., (1995), "Clone Clustering by Hybridization," Genomics 27, pp. 83–89.

Pevzner, P.A., Lysov, Yu.P., Khrapko, K.R., Belyavsky, A.V., Florentiev, V.L., Mirzabekov, A.D., (1991) "Improved Chips for Sequencing by Hybridization," Journal of Biomolecular Structure & Dynamics, ISSN 0739–1102, vol. 9, No. 2, pp. 399–410.

Venter, J.C., Adams, M.D., Martin–Gallardo, A., McCombie, W.R., Fields, C., (1992), "Genome sequence analysis: scientific objectives and practical strategies," TIBECH, vol. 10, pp. 8–11.

* cited by examiner

PREPARATION OF POOLS OF NUCLEIC ACIDS BASED ON REPRESENTATION IN A SAMPLE

FIELD OF THE INVENTION

The invention relates to nucleic acid pools useful in hybridization studies. In particular, the invention relates to methods for preparing such nucleic acid pools, arrays and kits produced from such pools, and an improved method for identifying a nucleic acid and/or its representation in a sample.

BACKGROUND

The rate of determining the sequence of the four nucleotides in nucleic acid samples is a major technical obstacle for further advancement of molecular biology, medicine, and biotechnology. Nucleic acid sequencing methods which involve separation of nucleic acid molecules in a gel have been in use since 1978. The other proven method for sequencing nucleic acids is sequencing by hybridization (SBH).

The traditional method of determining a sequence of nucleotides (i.e., the order of the A, G, C and T nucleotides in a sample) is performed by preparing a mixture of randomly-terminated, differentially labelled nucleic acid fragments by degradation at specific nucleotides, or by dideoxy chain termination of replicating strands. Resulting nucleic acid fragments in the range of 1 to 500 bp are then separated on a gel to produce a ladder of bands wherein the adjacent samples differ in length by one nucleotide.

The array-based approach of SBH does not require single base resolution in separation, degradation, synthesis or imaging of a nucleic acid molecule. Using mismatch discriminative hybridization of short oligonucleotides K bases in length, lists of constituent K-mer oligonucleotides may be determined for target nucleic acid. Sequence for the target nucleic acid may be assembled by uniquely overlapping scored oligonucleotides.

There are several approaches available to achieve sequencing by hybridization. In a process called SBH Format 1, nucleic acid samples are arrayed, and labeled probes are hybridized with the samples. Replica membranes with the same sets of sample nucleic acids may be used for parallel scoring of several probes and/or probes may be multiplexed. Nucleic acid samples may be arrayed and hybridized on nylon membranes or other suitable supports. Each membrane array may be reused many times. Format 1 is especially efficient for batch processing large numbers of samples.

In SBH Format 2, probes are arrayed at locations on a substrate which correspond to their respective sequences, and a labelled nucleic acid sample fragment is hybridized to the arrayed probes. In this case, sequence information about a fragment may be determined in a simultaneous hybridization reaction with all of the arrayed probes. For sequencing other nucleic acid fragments, the same oligonucleotide array may be reused. The arrays may be produced by spotting or by in situ synthesis of probes.

In Format 3 SBH, two sets of probes are used. In one embodiment, a set may be in the form of arrays of probes with known positions, and another, labelled set may be stored in multiwell plates. In this case, target nucleic acid need not be labelled. Target nucleic acid and one or more labelled probes are added to the arrayed sets of probes. If one attached probe and one labelled probe both hybridize contiguously on the target nucleic acid, they are covalently ligated, producing a detected sequence equal to the sum of the length of the ligated probes. The process allows for sequencing long nucleic acid fragments, e.g. a complete bacterial genome, without nucleic acid subcloning in smaller pieces.

In the present invention, SBH is applied to the efficient identification and sequencing of one or more nucleic acid samples. The procedure has many applications in nucleic acid diagnostics, forensics, and gene mapping. It also may be used to identify mutations responsible for genetic disorders and other traits, to assess biodiversity and to produce many other types of data dependent on nucleic acid sequence.

SUMMARY OF THE INVENTION

The present invention provides a method for detecting a target nucleic acid species including the steps of providing an array of probes affixed to a substrate and a plurality of labeled probes wherein each labeled probe is selected to have a first nucleic acid sequence which is complementary to a first portion of a target nucleic acid and wherein the nucleic acid sequence of at least one probe affixed to the substrate is complementary to a second portion of the nucleic acid sequence of the target, the second portion being adjacent to the first portion; applying a target nucleic acid to the array under suitable conditions for hybridization of probe sequences to complementary sequences; introducing a labeled probe to the array; hybridizing a probe affixed to the substrate to the target nucleic acid; hybridizing the labeled probe to the target nucleic acid; affixing the labeled probe to an adjacently hybridized probe in the array; and detecting the labeled probe affixed to the probe in the array. According to preferred methods of the invention the array of probes affixed to the substrate comprises a universal set of probes. According to other preferred aspects of the invention at least two of the probes affixed to the substrate define overlapping sequences of the target nucleic acid sequence and more preferably at least two of the labelled probes define overlapping sequences of the target nucleic acid sequences. Still further, according to another aspect of the invention a method is provided for detecting a target nucleic acid of known sequence comprising the steps of: contacting a nucleic acid sample with a set of immobilized oligonucleotide probes attached to a solid substrate under hybridizing conditions wherein the immobilized probes are capable of specific hybridization with different portions of said target nucleic acid sequence; contacting the target nucleic acid with a set of labelled oligonucleotide probes in solution under hybridizing conditions wherein the labeled probes are capable of specific hybridization with different portions of said target nucleic acid sequence adjacent to the immobilized probes; covalently joining the immobilized probes to labelled probes that are immediately adjacent to the immobilized probe on the target sequence (e.g., with ligase); removing any non-ligated labelled probes; detecting the presence of the target nucleic acid by detecting the presence of said labelled probe attached to the immobilized probes. The invention also provides a method of determining expression of a member of a set of partially or completely sequenced genes in a cell type, a tissue or a tissue mixture comprising the steps of: defining pairs of fixed and labeled probes specific for the sequenced gene; hybridizing unlabeled nucleic acid sample and corresponding labeled probes to one or more arrays of fixed probes; forming covalent bonds between adjacent hybridized labeled and fixed probes; removing unligated probes; and determining the presence of the sequenced gene by detection of labeled probes bound to prespecified locations in the array. In a preferred embodiment of this aspect of the invention, the target nucleic acid will identify the presence of an infectious agent.

Further, the present invention provides for an array of oligonucleotide probes comprising a nylon membrane; a plurality of subarrays of oligonucleotide probes on the nylon membrane, the subarrays comprising a plurality of individual spots wherein each spot is comprised of a plurality of oligonucleotide probes of the same sequence; and a plurality of hydrophobic barriers located between the subarrays on the nylon membrane, whereby the plurality of hyydrophobic barriers prevents cross contamination between adjacent subarrays.

Still further, the present invention provides a method for sequencing a repetitive sequence, having a first end and a second end, in a target nucleic acid comprising the steps of: (a) providing a plurality of spacer oligonucleotides of varying lengths wherein the spacer oligonucleotides comprise the repetitive sequence; (b) providing a first oligonucleotide that is known to be adjacent to the first end of the repetitive sequence; (c) providing a plurality of second oligonucleotides one of which is adjacent to the second end of the repetitive sequence, wherein the plurality of second oligonucleotides is labeled; (d) hybridizing the first and the plurality of second oligonucleotides, and one of the plurality of spacer oligonucleotides to the target nucleic acid; (e) ligating the hybridized oligonucleotides; (f) separating ligated oligonucleotides from unligated oligonucleotides; and (g) detecting label in the ligated oligonucleotides.

Still further, the present invention provides a method for sequencing a branch point sequence, having a first end and a second end, in a target nucleic acid comprising the steps of: (a) providing a first oligonucleotide that is complementary to a first portion of the branch point sequence wherein the first oligonucleotide extends from the first end of the branch point sequence by at least one nucleotide; (b) providing a plurality of second oligonucleotides that are labeled, and are complementary to a second portion of the branch point sequence wherein the plurality of second oligonucleotides extend from the second end of the branch point sequence by at least one nucleotide, and wherein the portion of the second oligonucleotides that extend from the second end of the branch point sequence comprise sequences that are complementary to a plurality of sequences that arise from the branch point sequence; (c) hybridizing the first oligonucleotide, and one of the plurality of second oligonucleotides to the target DNA; (d) ligating the hybridized oligonucleotides; (e) separating ligated oligonucleotides from unligated oligonucleotides; and (f) detecting label in the ligated oligonucleotides.

Still further, the present invention provides a method for confirming a sequence by using probes that are predicted to be negative for the target nucleic acid. The sequence of a target is then confirmed by hybridizing the target nucleic acid to the "negative" probes to confirm that these probes do not form perfect matches with the target nucleic acid.

Still further, the present invention provides a method for analyzing a nucleic acid using oligonucleotide probes that are complexed with different labels so that the probes may be multiplexed in a hybridization reaction without a loss of sequence information (i.e., different probes have different labels so that hybridization of the different probes to the target can be distinguished). In a preferred embodiment, the labels are radioisotopes, or floursecent molecules, or enzymes, or electrophore mass labels. In a more preferred embodiment, the differently labeled oligonucleotides probes are used in format III SBH, and multiple probes (more than two, with one probe being the immobilized probe) are ligated together.

Still further, the present invention provides a method for detecting the presence of a target nucleic acid having a known sequence when the target is present in very small amounts compared to homologous nucleic acids in a sample. In a preferred embodiment, the target nucleic acid is an allele present at very low frequency in a sample that has nucleic acids from a large number of sources. In an alternative preferred embodiment, the target nucleic acid has a mutated sequence, and is present at very low frequency within a sample of nucleic acids.

Still further, the present invention provides a method for confirming the sequence of a target nucleic acid by using single pass gel sequencing. Primers for single pass gel sequencing are derived from the sequence obtained by SBH, and these primers are used in standard Sanger sequencing reactions to provide gel sequence information for the target nucleic acid. The sequence obtained by single pass gel sequencing is then compared to the SBH derived sequence to confirm the sequence.

Still further, the present invention provides a method for solving branch points by using single pass gel sequencing. Primers for the single pass gel sequencing reactions are identified from the ends of the Sfs obtained after a first round of SBH sequencing, and these primers are used in standard Sanger-sequencing reactions to provide gel sequencing information through the branch points of the Sfs. Sfs are then aligned by comparing the Sanger-sequencing results through the branch points to the Sfs to identify adjoining Sfs.

Still further, the present invention provides for a method of preparing a sample containing target nucleic acids by PCR, without purifying the PCR products prior to the SBH reactions. In Format I SBH, crude PCR products are applied to a substrate without prior purification, and the substrate may be washed prior to introduction of the labeled probes.

Still further, the present invention provides a method and an apparatus for analyzing a target nucleic acid. The apparatus comprises two arrays of nucleic acids that are mixed together at the desired time. In a preferred embodiment, the nucleic acids in one of the arrays are labeled. In a more preferred embodiment, a material is disposed between the two arrays and this material prevents the mixing of nucleic acids in the arrays. When this material is removed, or rendered permeable, the nucleic acids in the two arrays are mixed together. In an alternative preferred embodiment, the nucleic acids in one array are target nucleic acids and the nucleic acids in the other are oligonucleotide probes. In another preferred embodiment, the nucleic acids in both arrays are oligonucleotide probes. In another preferred embodiment, the nucleic acids in one array are oligonucleotide probes and target nucleic acids, and nucleic acids in the other array are oligonucleotide probes. In another preferred embodiment, the nucleic acids in both arrays are oligonucleotide probes and target nucleic acids.

One method of the present invention using the apparatus described above comprises the steps of providing an array of nucleic acids fixed to a substrate, providing a second array of nucleic acids, providing conditions that allow the nucleic acids in the second array to come into contact with the nucleic acids of the fixed array wherein one of the arrays of nucleic acids are target nucleic acids and the other array is oligonucleotide probes, and analyzing the hybridization results. In a preferred embodiment, the fixed array is target nucleic acid and the second array is labeled oligonucleotide probes. In a more preferred embodiment, there is a material disposed between the two arrays that prevents mixing of the nucleic acids until the material is removed or rendered permeable to the nucleic acids.

In a second method of the present invention using the apparatus described above comprises the steps of providing two arrays of nucleic acid probes, providing conditions that allow the two arrays of probes to come into contact with each other and a target nucleic acid, ligating together probes that are adjacent on the target nucleic acid, and analyzing the results. In a preferred embodiment, the probes in one array are fixed and the probes in the other array are labeled. In a more preferred embodiment, there is a material disposed between the two arrays that prevents mixing of the probes until the material is removed or rendered permeable to the probes.

Still further, the present invention provides substrates on which arrays of oligonucleotide probes are fixed, wherein each probe is separated from its neighboring probes by a physical barrier that is resistant to the flow of the sample solution. In a preferred embodiment, the physical barrier is made of a hydrophobic material.

Still further, the present invention provides a method for making the arrays of oligonucleotide probes that are separated by physical barriers. In a preferred embodiment, a grid is applied to the substrate using an ink-jet head that applies a material which reduces the reaction volume of the array.

Still further, the present invention provides substrates on which oligonucleotides are fixed to form a three-dimensional array. The three-dimensional array combines high resolution for reading probe results (each level has a relatively low density of probes per $cm^2$), with high information content in three dimensional space (multiple levels or probes).

Still further, the present invention provides a substrate to which oligonucleotide probes are fixed, wherein the oligonucleotide probes have spacers, and wherein the spacers increase the distance between the substrate and the informational portion of the oligonucleotide probe (e.g., the portion of the oligonucleotide probe which binds to the target and gives sequence information). In a preferred embodiment, the spacer comprises ribose sugars and phosphates, wherein the phosphates covalently bind the ribose sugars into a polymer by forming esters with the ribose sugars through their 5' and 3' hydroxyl groups.

Still further, the present invention provides a method for clustering cDNA clones into groups of similar or identical sequences, so that single representative clones may be selected from each group for sequencing. In a preferred embodiment, the method for clustering is used in the sequencing of a plurality of clones, comprising the steps of: interrogating each clone with a plurality of oligonucleotide probes; determining which probes bind to each clone and the signal intensity for each probe; clustering clones into a plurality of groups by identifying clones that bind to similar probes with similar intensities; and sequencing at least one clone from each group. In a more preferred embodiment, the plurality of probes comprises from about 50 to about 500 different probes. In a another more preferred embodiment, the plurality of probe comprises about 300 different probes. In a most preferred embodiment, the plurality of clones are a plurality of cDNA clones.

Still further, the invention relates to oligonucleotide probes complexed (covalent or noncovalent) to discrete particles wherein the particles can be grouped into a plurality of sets based on a physical property. In a preferred embodiment, a different probe is attached to the discrete particles of each set, and the identity of the probe is determined by identifying the physical property of the discrete particles. In an alternative embodiment, the probe is identified on the basis of a physical property of the probe. The physical property includes any that can be used to differentiate the discrete particles, and includes, for example, size, flourescence, radioactivity, electromagnetic charge, or absorbance, or label(s) may be attached to the particle such as a dye, a radionuclide, or an EML. In a preferred embodiment, discrete particles are separated by a flow cytometer which detects the size, charge, flourescence, or absorbance of the particle.

The invention also relates to methods using the probes complexed with the discrete particles to analyze target nucleic acids. These probes may be used in any of the methods described above, with the modification of identifying the probe by the physical property of the discrete particle. These probes may also be used in a format III approach where the "free" probe is identified by a label, and the probe complexed to the discrete particle is identified by the physical property. In a preferred embodiment, the probes are used to sequence a target nucleic acid using SBH.

The invention also relates to methods using agents which destabilize the binding of complementary polynucleotide strands (decrease the binding energy), or increase stability of binding between complementary polynucleotide strands (increase the binding energy). In preferred embodiments, the agent is a tetraalkyl ammonium salt, sodium chloride, a phosphate salt, a borate salt, an organic solvent such as formamide, glycol, dimethylsulfoxide, and dimethylformamide, urea, guanidinium, an amino acid analog such as betaine, a polyamine such as spermidine and spermine, or other positively charged molecules which neutralize the negative charge of the phosphate backbone, a detergent such as sodium dodecyl sulfate, and sodium lauryl sarcosinate, a minor/major groove binding agent, a positively charged polypeptide, an intercalating agent such as acridine, ethidium bromide, and anthracine, and a polyanion such as an alkyl polysulphonic acid. In a preferred embodiment, an agent is used to reduce or increase the $T_m$ of a pair of complementary polynucleotides. In a more preferred embodiment, a mixture of the agents is used to reduce or increase the $T_m$ of a pair of complementary polynucleotides. In a preferred embodiment, the agent or agents are added so that the binding energy from an AT base pair is approximately equivalent to the binding energy of a GC base pair. The energy of binding of these complementary polynucleotides may be increased by adding an agent that neutralizes or shields the negative charges of the phosphate groups in the polynucleotide backbone. In a most preferred embodiment, the agent or agents are used to enhance the discrimination of discrimination of perfect matches from mismatches for complementary polynucleotides.

The invention also relates to methods of increasing the discrimination of perfect matches from mismatches for complementary polynucleotides. In preferred embodiments, this discrimination is increased by changing a physical property in the method, e.g., the temperature, and/or adding an agent which increases discrimination, e.g., spermadine or formamide. In a more preferred embodiment, a mixture of agents and/or physical conditions is used to increase the discrimination of perfect matches from mismatches between a probe and a target nucleic acid. In a most preferred embodiment, the change in physical condition or addition of an agent enhances discrimination in a number of ways, for example, the physical condition or agent may increase the difference in the on rates or off rates between a perfect match product and a mismatch product (a kinetic effect); or the reaction time may be decreased so that binding of the probe to a perfect match site and/or a mismatch site does not reach equilibrium; or the physical condition or agent may increase the binding energy difference between a perfect match and a mismatch (a free energy [$\Delta G$] effect); or the physical condition or agent may enhance the discrimination effect of another agent or physical condition ($\Delta G$ or kinetic effect); or the physical condition or agent may preferentially modify the perfect match or mismatch complexes formed between complementary polynucleotides; or the physical condition or agent may enhance the discrimination of the physical condition or agent which physically modifies the complexed polynucleotides ($\Delta G$, kinetic, or conformational effect); or some combination of these and other factors. In a preferred embodiment, the agent, agents or physical condition(s) modify the activity of a protein which binds to and/or modifies the complexed or uncomplexed nucleic acids. In a preferred embodiment, the agent is one of those recited supra. In a preferred embodiment, the physical condition is selected from the group comprising temperature, pH, ionic strength, time, and/or others such as, e.g., those listed in *The Handbook of Chemistry and Physics,* CRC Press.

The invention also relates to methods for enhancing the activity of a nucleic acid modifying polypeptide on a target nucleic acid, comprising the steps of contacting the target nucleic acid with at least one polynucleotide under conditions which allow a perfect match to be discriminated from a mismatch, wherein an agent is added to enhance the discrimination of the perfect match from the mismatch; and contacting the complex formed between the polynucleotide and the target nucleic acid with the nucleic acid modifying polypeptide, wherein the activity of the nucleic acid modifying polypeptide is enhanced by the enhanced discrimination. In preferred embodiments, the nucleic acid modifying polypeptide is selected from the group comprising a ligase, a nucleic acid polymerase, an integrase, a gyrase, a nuclease, a helicase, a methylase, and a capping enzyme. In an alternative preferred embodiment, the methods are used to enhance the binding of nucleic acid binding proteins, such as, for example, transcription factors, repressors, and structural polypeptides such as, for example, histones. In a most preferred embodiment, the nucleic acid modifying polypeptide is a ligase that has been modified to enhance its discrimination of perfect matches from mismatches.

In one embodiment, the invention includes methods for preparing nucleic acid pools useful in the hybridization studies described herein. This embodiment allows hybridization conditions, such as time, temperature, ionic strength, etc., to be adjusted to increase the likelihood that hybridization to the nucleic acids within each pool is within the linear range of detection (i.e., detectable but not saturating).

The methods of this embodiment rely on pooling nucleic acids derived from a sample, based on the degree of representation within the sample, i.e., nucleic acids having similar degrees of representation within in a sample are combined into a pool. As used herein, the term "combined" can refer to physical mixing of nucleic acids, but also encompasses the classification of nucleic acids as belonging to a particular pool without physical mixing of nucleic acids. Two, three, four, five, or more pools can be produced from each sample. Conveniently, three pools are produced: one pool containing nucleic acids having "low" representation, one pool containing nucleic acids having "intermediate" representation, and one pool containing nucleic acids having "high" representation. The terms "low," "intermediate," and "high" are used in this context to define relationships among the pools, rather than to refer to absolute degrees of representation. In other words, "high representation" refers to a higher degree of representation than "intermediate representation," and those skilled in the art understand that what constitutes high representation can vary from sample to sample.

The nucleic acid pools can be prepared from any nucleic acids, including genomic DNA, DNA produced by amplification, cDNA, and RNA. Samples from which the nucleic acids are typically derived include, for example, a tissue, cell (eukaryotic or prokaryotic), and nucleic acid library (e.g., a genomic or cDNA library). Nucleic acid pools are conveniently prepared from cDNA, such as a cDNA library. In this instance, cDNA clones can be pooled based on the degree of representation in the cDNA library. Such pools can then be used in hybridization studies. Nucleic acid pools according to the invention are particularly useful for determining the degree of representation of one or more target nucleic acids in a sample. For example, pools of cDNA clones can be employed in an expression monitoring study where RNA or cDNA from a tissue or cell of interest is contacted with the pooled cDNAs to determine the presence and expression levels of the RNAs in the tissue or cell.

Thus, the invention also provides an improved method for identifying a nucleic acid and/or its representation in a sample. In this method, the nucleic acids in each pool can be contacted with one or more target nucleic acids and/or oligonucleotide probes under conditions suitable for hybridization and hybridization detected. Suitable hybridization conditions are different for each pool. Conveniently, a shorter hybridization time is used when hybridizing nucleic acids from a "high representation" pool relative to the hybridization time for nucleic acids from a lower representation pool. Alternatively (or in addition), one or more factors affecting the rate of association of nucleic acid strands can be adjusted to help ensure linearity.

Hybridization can be carried out in any of a variety of formats. In particular, the invention includes a method in which nucleic acids subjected to pooling (hereafter "pooled nucleic acids") are affixed to one or more substrates and hybridized with soluble target nucleic acid(s) and/or oligonucleotide probe(s) (i.e., sequencing by hybridization [SBH] Format 1), a method in which target nucleic acid(s) and/or oligonucleotide probe(s) are affixed to one or more substrates and hybridized with the pooled nucleic acids (i.e., SBH Format 2), and a method in which both the pooled nucleic acids and the target nucleic acid(s) and/or oligonucleotide probe(s) are in solution. The invention further encompasses methods in which pooled nucleic acids are employed in SBH Format 3 hybridization studies in which the pooled nucleic acids are either affixed to one or more substrates or are in solution. In all of these formats, where the pooled nucleic acids are in solution, they are generally labeled.

In methods wherein the pooled nucleic acids are affixed to one or more substrates, the nucleic acids can conveniently be arrayed such that, for each dot in the array, the corresponding pool is known, and thus the degree of representation of the nucleic acid in the dot is known. Hybridization conditions are then adjusted to facilitate hybridization with nucleic acids of a given pool, and hybridization at all dots corresponding to that pool is then determined. In a variation of this embodiment, each pool of representative nucleic acids is arrayed on a substrate to form a separate array of nucleic acids. This step produces multiple arrays, each containing nucleic acids having a degree of representation in the sample that is within a predetermined range, wherein the range differs for each array so produced. The arrays produced from nucleic acids derived from a given sample can be combined to form kits. Thus, in addition to methods, the present invention provides arrays and kits produced from pooled nucleic acids.

Another aspect of the invention is a method in which nucleic acids are selected from a sample and assigned to pools based on an SBH study in which nucleic acids are clustered into groups having the same or similar nucleotide sequences. More specifically, nucleic acids from a sample are contacted with a plurality of oligonucleotide probes under suitable conditions for hybridization of oligonucleotide probes to nucleic acids. Nucleic acids that bind to the same sets of oligonucleotide probes are identified and clustered into a plurality of groups. Each such group includes nucleic acids that share a common "oligonucleotide probe signature" and therefore is expected to include nucleic acids having the same or similar nucleotide sequences. The number of nucleic acids in each group is determined as an indication of their degree of representation in the sample. A representative nucleic acid is selected from each group to obtain a series of representative nucleic acids, which are then combined into a plurality of pools based on degree of representation in the sample.

In another variation of this embodiment, the degree of representation in a sample is determined by any conventional method, such as, for example, intensity of hybridization signal in a hybridization study.

DETAILED DESCRIPTION OF THE PREFERRED EMBODIMENTS

Format 1 SBH is appropriate for the simultaneous analysis of a large set of samples. Parallel scoring of thousands of samples on large arrays may be performed in thousands of independent hybridization reactions using small pieces of membranes. The identification of DNA may involve 1–20 probes per reaction and the identification of mutations may in some cases involve more than 1000 probes specifically selected or designed for each sample. For identification of the nature of the mutated DNA segments, specific probes may be synthesized or selected for each mutation detected in the first round of hybridizations.

DNA samples may be prepared in small arrays which may be separated by appropriate spacers, and which may be simultaneously tested with probes selected from a set of oligonucleotides which may be arrayed in multiwell plates. Small arrays may consist of one or more samples. DNA samples in each small array may include mutants or individual samples of a sequence. Consecutive small arrays may be organized into larger arrays. Such larger arrays may include replication of the same small array or may include arrays of samples of different DNA fragments. A universal set of probes includes sufficient probes to analyze a DNA fragment with prespecified precision, e.g. with respect to the redundancy of reading each base pair ("bp"). These sets may include more probes than are necessary for one specific fragment, but may include fewer probes than are necessary for testing thousands of DNA samples of different sequence.

DNA or allele identification and a diagnostic sequencing process may include the steps of:

1) Selection of a subset of probes from a dedicated, representative or universal set to be hybridized with each of a plurality of small arrays;
2) Adding a first probe to each subarray on each of the arrays to be analyzed in parallel;
3) Performing hybridization and scoring of the hybridization results;
4) Stripping off previously used probes;
5) Repeating hybridization, scoring and stripping steps for the remaining probes which are to be scored;
5) Processing the obtained results to obtain a final analysis or to determine additional probes to be hybridized;
6) Performing additional hybridizations for certain subarrays; and
7) Processing complete sets of data and obtaining a final analysis.

This approach provides fast identification and sequencing of a small number of nucleic acid samples of one type (e.g. DNA, RNA), and also provides parallel analysis of many sample types in the form of subarrays by using a presynthesized set of probes of manageable size. Two approaches have been combined to produce an efficient and versatile process for the determination of DNA identity, for DNA diagnostics, and for identification of mutations.

For the identification of known sequences, a small set of shorter probes may be used in place of a longer unique probe. In this approach, although there may be more probes to be scored, a universal set of probes may be synthesized to cover any type of sequence. For example, a full set of 6-mers includes only 4,096 probes, and a complete set of 7-mers includes only 16,384 probes.

Full sequencing of a DNA fragment may be performed with two levels of hybridization. One level is hybridization of a sufficient set of probes that cover every base at least once. For this purpose, a specific set of probes may be synthesized for a standard sample. The results of hybridization with such a set of probes reveal whether and where mutations (differences) occur in non-standard samples. Further, this set of probes may include "negative" probes to confirm the hybridization results of the "positive" probes. To determine the identity of the changes, additional specific probes may be hybridized to the sample. This additional set of probes will have both "positive" (the mutant sequence) and "negative" probes, and the sequence changes will be identified by the positive probes and confirmed by the negative probes.

In another embodiment, all probes from a universal set may be scored. A universal set of probes allows scoring of a relatively small number of probes per sample in a two step process without an undesirable expenditure of time. The hybridization process may involve successive probings, in a first step of computing an optimal subset of probes to be hybridized first and, then, on the basis of the obtained results, a second step of determining additional probes to be scored from among those in a universal set. Both sets of probes have "negative" probes that confirm the positive probes in the set. Further, the sequence that is obtained may then be confirmed in a separate step by hybridizing the sample with a set of "negative" probes identified from the SBH results.

In SBH sequence assembly, K-1 oligonucleotides which occur repeatedly in analyzed DNA fragments due to chance or biological reasons may be subject to special consideration. If there is no additional information, relatively small fragments of DNA may be fully assembled in as much as every base pair is read several times.

In the assembly of relatively longer fragments, ambiguities may arise due to the repeated occurrence in a set of positively-scored probes of a K-1 sequence (i.e., a sequence shorter than the length of the probe). This problem does not exist if mutated or similar sequences have to be determined (i.e., the K-1 sequence is not identically repeated). Knowledge of one sequence may be used as a template to correctly assemble a sequence known to be similar (e.g. by its presence in a database) by arraying the positive probes for the unknown sequence to display the best fit on the template.

The use of an array of sample avoids consecutive scoring of many oligonucleotides on a single sample or on a small set of samples. This approach allows the scoring of more probes in parallel by manipulation of only one physical object. Subarrays of DNA samples 1000 bp in length may be sequenced in a relatively short period of time. If the samples are spotted at 50 subarrays in an array and the array is reprobed 10 times, 500 probes may be scored. In screening for the occurrence of a mutation, enough probes may be used to cover each base three times. If a mutation is present, several covering probes will be affected. The use of information about the identity of negative probes may map the mutation with a two base precision. To solve a single base mutation mapped in this way, an additional 15 probes may be employed. These probes cover any base combination for two questionable positions (assuming that deletions and insertions are not involved). These probes may be scored in one cycle on 50 subarrays which contain a given sample. In the implementation of a multiple label color scheme (i.e., multiplexing), two to six probes, each having a different label such as a different fluorescent dye, may be used as a pool, thereby reducing the number of hybridization cycles and shortening the sequencing process.

In more complicated cases, there may be two close mutations or insertions. They may be handled with more probes. For example, a three base insertion may be solved with 64 probes. The most complicated cases may be approached by several steps of hybridization, and the selecting of a new set of probes on the basis of results of previous hybridizations.

If subarrays to be analyzed include tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel facilitates scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be analyzed. These targets may represent pools of fragments such as pools of exon clones.

A specific hybridization scoring method may be employed to define the presence of mutants in a genomic segment to be sequenced from a diploid chromosomal set. Two variations are where: i) the sequence from one chromosome represents a known allele and the sequence from the other represents a new mutant; or, ii) both chromosomes contain new, but different mutants. In both cases, the scanning step designed to map changes gives a maximal signal difference of two-fold at the mutant position. Further, the method can be used to identify which alleles of a gene are carried by an individual and whether the individual is homozygous or heterozygous for that gene.

Scoring two-fold signal differences required in the first case may be achieved efficiently by comparing corresponding signals with homozygous and heterozygous controls. This approach allows determination of a relative reduction in the hybridization signal for each particular probe in a given sample. This is significant because hybridization efficiency may vary more than two-fold for a particular probe hybridized with different nucleic acid fragments having the same full match target. In addition, different mutant sites may affect more than one probe depending upon the number of oligonucleotide probes. Decrease of the signal for two to four consecutive probes produces a more significant indication of a mutant site. Results may be checked by testing with small sets of selected probes among which one or few probes selected to give a full match signal which is on average eight-fold stronger than the signals coming from mismatch-containing duplexes.

Partitioned membranes allow a very flexible organization of experiments to accommodate relatively larger numbers of samples representing a given sequence type, or many different types of samples represented with relatively small numbers of samples. A range of 4–256 samples can be handled with particular efficiency. Subarrays within this range of numbers of dots may be designed to match the configuration and size of standard multiwell plates used for storing and labeling oligonucleotides. The size of the subarrays may be adjusted for different number of samples, or a few standard subarray sizes may be used. If all samples of a type do not fit in one subarray, additional subarrays or membranes may be used and processed with the same probes. In addition, by adjusting the number of replicas for each subarray, the time for completion of identification or sequencing process may be varied.

As used herein, "intermediate fragment" means an oligonucleotide between 5 and 1000 bases in length, and preferably between 10 and 40 bp in length.

In Format 3, a first set of oligonucleotide probes of known sequence is immobilized on a solid support under conditions which permit them to hybridize with nucleic acids having respectively complementary sequences. A labeled, second set of oligonucleotide probes is provided in solution. Both within the sets and between the sets the probes may be of the same length or of different lengths. A nucleic acid to be sequenced or intermediate fragments thereof may be applied to the first set of probes in double-stranded form (especially where a recA protein is present to permit hybridization under non-denaturing conditions), or in single-stranded form and under conditions which permit hybrids of different degrees of complementarity (for example, under conditions which allow discrimination between full match and one base pair mismatch hybrids). The nucleic acid to be sequenced or intermediate fragments thereof may be applied to the first set of probes before, after or simultaneously with the second set of probes. Probes that bind to adjacent sites on the target are bound together (e.g., by stacking interactions or by a ligase or other means of causing chemical bond formation between the adjacent probes). After permitting adjacent probes to be bound, fragments and probes which are not immobilized to the surface by chemical bonding to a member of the first set of probe are washed away, for example, using a high temperature (up to 100 degrees C.) wash solution which melts hybrids. The bound probes from the second set may then be detected using means appropriate to the label employed (which may, for example, be chemiluminescent, fluorescent, radioactive, enzymatic, densitometric, or electrophore mass labels).

Herein, nucleotide bases "match" or are "complementary" if they form a stable duplex by hydrogen bonding under specified conditions. For example, under conditions commonly employed in hybridization assays, adenine ("A") matches thymine ("T"), but not guanine ("G") or cytosine ("C"). Similarly, G matches C, but not A or T. Other bases which will hydrogen bond in less specific fashion, such as inosine or the Universal Base ("M" base, Nichols et al 1994), or other modified bases, such as methylated bases, for example, are complementary to those bases for which they form a stable duplex under specified conditions. A probe is said to be "perfectly complementary" or is said to be a "perfect match" if each base in the probe forms a duplex by hydrogen bonding to a base in the nucleic acid to be sequenced according to the Watson and Crick base paring rules (i.e., absent any surrounding sequence effects, the duplex formed has the maximal binding energy for a particular probe). "Perfectly complementary" and "perfect match" are also meant to encompass probes which have analogs or modified nucleotides. A "perfect match" for an analog or modified nucleotide is judged according to a "perfect match rule" selected for that analog or modified nucleotide (e.g., the binding pair that has maximal binding energy for a particular analog or modified nucleotide). Each base in a probe that does not form a binding pair according to the "rules" is said to be a "mismatch" under the specified hybridization conditions.

A list of probes may be assembled wherein each probe is a perfect match to the nucleic acid to be sequenced. The probes on this list may then be analyzed to order them in maximal overlap fashion. Such ordering may be accomplished by comparing a first probe to each of the other probes on the list to determine which probe has a 3' end which has the longest sequence of bases identical to the sequence of bases at the 5' end of a second probe. The first and second probes may then be overlapped, and the process may be repeated by comparing the 5' end of the second probe to the 3' end of all of the remaining probes and by comparing the 3' end of the first probe with the 5' end of all of the remaining probes. The process may be continued until there are no probes on the list which have not been overlapped with other probes. Alternatively, more than one probe may be selected from the list of positive probes, and more than one set of overlapped probes ("sequence nucleus") may be generated in parallel. The list of probes for either such process of sequence assembly may be the list of all probes which are perfectly complementary to the nucleic acid to be sequenced or may be any subset thereof.

The 5' and 3' ends of the probes may be overlapped to generate longer stretches of sequence. This process of assembling probes continues until an ambiguity arises because of a branch point (a probe is repeated in the fragment), repetitive sequences longer than the probes, or an uncloned segment. The stretches of sequence between any two ambiguities are referred to as fragment of a subclone sequence (Sfs). Where ambiguities arise in sequence assembly due to the availability of alternative proper overlaps with probes, hybridization with longer probes spanning the site of overlap alternatives, competitive hybridization, ligation of alternative end to end pairs of probes spanning the site of ambiguity or single pass gel analysis (to provide an unambiguous ordering of Sfs) may be used.

By employing the above procedures, one may obtain any desired level of sequence, from a pattern of hybridization (which may be correlated with the identity of a nucleic acid sample to serve as a signature for identifying the nucleic acid sample) to overlapping or non-overlapping probes up through assembled Sfs and on to complete sequence for an intermediate fragment or an entire source DNA molecule (e.g. a chromosome).

Sequencing may generally comprise the following steps:
(a) contacting an array of immobilized oligonucleotide probes with a nucleic acid fragment under conditions effective to allow the fragment to form a primary complex with an immobilized probe having a complementary sequence;
(b) contacting this primary complex with a set of labeled oligonucleotide probes in solution under conditions effective to allow the primary complex to hybridize to the labeled probe, thereby forming secondary complexes wherein the fragment is hybridized with both an immobilized probe and a labeled probe;
(c) removing from a secondary complex any labeled probe that has not hybridized adjacent to an immobilized probe;
(d) detecting the presence of adjacent labeled and unlabeled probes by detecting the presence of the label; and
(e) determining a nucleotide sequence of the fragment by connecting the known sequence of the immobilized and labeled probes.

Hybridization and washing conditions may be selected to detect substantially perfect match hybrids (such as those wherein the fragment and probe hybridize at six out of seven positions), may be selected to allow differentiation of perfect matches and one base pair mismatches, or may be selected to permit detection only of perfect match hybrids.

Suitable hybridization conditions may be routinely determined by optimization procedures or pilot studies. Such procedures and studies are routinely conducted by those skilled in the art to establish protocols for use in a laboratory. See e.g., Ausubel et al., *Current Protocols in Molecular Biology*, Vol. 1–2, John Wiley & Sons (1989); Sambrook et al., Molecular Cloning A Laboratory Manual, 2nd Ed., Vols. 1–3, Cold Springs Harbor Press (1989); and Maniatis et al., *Molecular Cloning: A Laboratory Manual,* Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

In embodiments wherein the labeled and immobilized probes are not physically or chemically linked, detection may rely solely on washing steps of controlled stringency. Under such conditions, adjacent probes have increased binding affinity because of stacking interactions between the adjacent probes. Conditions may be varied to optimize the process as described above.

In embodiments wherein the immobilized and labeled probes are ligated, ligation may be implemented by a chemical ligating agent (e.g. water-soluble carbodiimide or cyanogen bromide), or a ligase enzyme, such as the commercially available $T_4$ DNA ligase may be employed. The washing conditions may be selected to distinguish between adjacent versus nonadjacent labeled and immobilized probes exploiting the difference in stability for adjacent probes versus nonadjacent probes.

Oligonucleotide probes may be labeled with fluorescent dyes, chemiluminescent systems, radioactive labels (e.g., $^{35}S$, $^{3}H$, $^{32}P$ or $^{33}P$) or with isotopes detectable by mass spectrometry.

Where a nucleic acid molecule of unknown sequence is longer than about 45 or 50 bp, the molecule may be fragmented and the sequences of the fragments determined. Fragmentation may be accomplished by restriction enzyme digestion, shearing or NaOH. Fragments may be separated by size (e.g. by gel electrophoresis) to obtain a preferred fragment length of about ten to forty bps.

Oligonucleotides may be immobilized, by a number of methods known to those skilled in the art, such as laser-activated photodeprotection attachment through a phosphate group using reagents such as a nucleoside phosphoramidite or a nucleoside hydrogen phosphorate. Glass, nylon, silicon and fluorocarbon supports may be used.

In a preferred embodiment, oligonucleotides are attached to a glass surface using a modified protocol from Zehn Gao et al., Nucl. Acids. Res. (1994) 22:5456–5465. In this protocol, the glass surface is activated by adding an aminosilane functional group, that is coupled with a phenyldiisothiocyanate (DITC). 5'-amino oligonucleotides are attached to this glass substrate by spotting onto the DITC activated glass surface and incubating for one hour at 37° C. in a humid chamber.

Oligonucleotides may be organized into arrays, and these arrays may include all or a subset of all probes of a given length, or sets of probes of selected lengths. Hydrophobic partitions may be used to separate probes or subarrays of probes. Arrays may be designed for various applications (e.g. mapping, partial sequencing, sequencing of targeted regions for diagnostic purposes, mRNA sequencing and large scale sequencing). A specific chip may be designed to be dedicated to a particular application by selecting a combination and arrangement of probes on a substrate.

For example, 1024 immobilized probe arrays of all oligonucleotide probes 5 bases in length (each array containing 1024 distinct probes) may be constructed. The probes in this example are 5-mers in an informational sense (they may actually be longer probes). A second set of 1024 5-mer probes may be labeled, and one of each labeled probe may be applied to an array of immobilized probes along with a fragment to be sequenced. In this example, 1024 arrays would be combined in a large superarray, or "superchip." In those instances where an immobilized probe and one of the labeled probes hybridize end-to-end along a nucleic acid fragment, the two probes are joined, for example by ligation, and, after removing unbound label, 10-mers complementary to the sample fragment are detected by the correlation of the presence of a label at a point in an array having an immobilized probe of known sequence to which was applied a labeled probe of known sequence. The sequence of the sample fragment is simply the sequence of the immobilized probe continued in the sequence of the labeled probe. In this way, all one million possible 10-mers may be tested by a combinatorial process which employs only 5-mers and which thus involves one thousandth of the amount of effort for oligonucleotide synthesis.

In a preferred embodiment, the substrate which supports the array of oligonucleotide probes is partitioned into sections so that each probe in the array is separated from adjacent probes by a physical barrier which may be, for example, a hydrophobic material. In a preferred embodiment, the physical barrier has a width of from 100 $\mu$m to 30 $\mu$m. In a more preferred embodiment, the distance from the center of each probe to the center of any adjacent probes is 325 $\mu$m. These arrays of probes may be "mass-produced" using a nonmoving, fixed substrate or a substrate fixed to a rotating drum or plate with an ink-jet deposition apparatus, for example, a microdrop dosing head; and a suitable robotic system, for example, an anorad gantry.

In an alternative preferred embodiment, the oligonucleotide probes are fixed to a three-dimensional array. The three-dimensional array is comprised of multiple layers, and each layer may be analyzed separate and apart from the other layers. The three dimensional array may take a number of forms, including, for example, the array may be disposed on a substrate having multiple depressions with probes located at different depths within the depressions (each level is made up of probes at similar depths within the depression); or the array may be disposed on a substrate having depressions of different depths with the probes located at the bottom of the depression, or at the peaks separating the depressions or some combination of peaks and depressions may be used (each level is made up of all the probes at a certain depth); or the array may be disposed on a substrate comprised of multiple sheets that are layered to form a three-dimensional array.

The probes in these arrays may include spacers that increase the distance between the surface of the substrate and the informational portion of the probes. The spacers may be comprised of atoms capable of forming at least two covalent bonds such as carbon, silicon, oxygen, sulfur, phosphorous, and the like, or may be comprised of molecules capable of forming at least two covalent bonds such as sugar-phosphate groups, amino acids, peptides, nucleosides, nucleotides, sugars, carbohydrates, aromatic rings, hydrocarbon rings, linear and branched hydrocarbons, and the like.

A nucleic acid sample to be sequenced may be fragmented or otherwise treated (for example, by the use of recA) to avoid hindrance to hybridization from secondary structure in the sample. The sample may be fragmented by, for example, digestion with a restriction enzyme such as Cvi JI, physical shearing (e.g. by ultrasound ), or by NaOH treatment. The resulting fragments may be separated by gel electrophoresis and fragments of an appropriate length, such as between about 10 bp and about 40 bp, may be extracted from the gel. In a preferred embodiment, the "fragments" of the nucleic acid sample cannot be ligated to other fragments in the pool. Such a pool of fragments may be obtained by treating the fragmented nucleic acids with a phosphatase (e.g., calf intestinal phosphatase). Alternatively, nonligatable fragments of the sample nucleic acid may be obtained by using random primers (e.g., $N_5$–$N_9$, where N=A, G, T, or C) in a Sanger-dideoxy sequencing reaction with the sample nucleic acid. This will produce fragments of DNA that have a complementary sequence to the target nucleic acid and that are terminated in a dideoxy residue that cannot be ligated to other fragments.

A reusable Format 3 SBH array may be produced by introducing a cleavable bond between the fixed and labeled probes and then cleaving this bond after a round of Format 3 analyzes is finished. The labeled probes may be ribonucleotides or a ribonucleotide may be used as the joining base in the labeled probe so that this probe may subsequently be removed, e.g., by RNAse or uracil-DNA glycosylate treatment, or NaOH treatment. In addition, bonds produced by chemical ligation may be selectively cleaved.

Other variations include the use of modified oligonucleotides to increase specificity or efficiency, cycling hybridizations to increase the hybridization signal, for example by performing a hybridization cycle under conditions (e.g. temperature) optimally selected for a first set of labeled probes followed by hybridization under conditions optimally selected for a second set of labeled probes. Shifts in reading frame may be determined by using mixtures (preferably mixtures of equimolar amounts) of probes ending in each of the four nucleotide bases A, T, C and G.

Branch points produce ambiguities as to the ordered sequence of a fragment. Although the sequence information is determined by SBH, either: (i) long read length, single-pass gel sequencing at a fraction of the cost of complete gel sequencing; or (ii) comparison to related sequences, may be used to order hybridization data where such ambiguities ("branch points") occur. Primers for single pass gel sequencing through the branch points are identified from the SBH sequence information or from known vector sequences, e.g., the flanking sequences to the vector insert site, and standard Sanger-sequencing reactions are performed on the sample nucleic acid. The sequence obtained from this single pass gel sequencing is compared to the Sfs that read into and out of the branch points to identify the order of the Sfs. Alternatively, the Sfs may be ordered by comparing the sequence of the Sfs to related sequences and ordering the Sfs to produce a sequence that is closest to the related sequence.

In addition, the number of tandem repetitive nucleic acid segments in a target fragment may be determined by single-pass gel sequencing. As tandem repeats occur rarely in protein-encoding portions of a gene, the gel-sequencing step will be performed only when one of these noncoding regions is identified as being of particular interest (e.g., if it is an important regulatory region).

Obtaining information about the degree of hybridization exhibited for a set of only about 200 oligonucleotides probes (about 5% of the effort required for complete sequencing) defines a unique signature of each gene and may be used for sorting the cDNAs from a library to determine if the library contains multiple copies of the same gene. By such signatures, identical, similar and different cDNAs can be distinguished and inventoried.

Nucleic acids and methods for isolating, cloning and sequencing nucleic acids are well known to those of skill in the art. See e.g., Ausubel et al., *Current Protocols in Molecular Biology*, Vol. 1–2, John Wiley & Sons (1989); and Sambrook et al., Molecular Cloning A Laboratory Manual, 2nd Ed., Vols. 1–3, Cold Springs Harbor Press (1989), both of which are incorporated by reference herein.

SBH is a well developed technology that may be practiced by a number of methods known to those skilled in the art. Specifically, techniques related to sequencing by hybridization of the following documents is incorporated by reference herein: Drmanac et al., U.S. Pat. No. 5,202,231 (hereby incorporated by reference herein)—Issued Apr. 13, 1993; Drmanac et al., *Genomics*, 4, 114–128 (1989); Drmanac et al., *Proceedings of the First Int'l. Conf. Electrophoresis Supercomputing Human Genome Cantor et al.* eds, World Scientific Pub. Co., Singapore, 47–59 (1991); Drmanac et al., *Science*, 260, 1649–1652 (1993); Lehrach et al., *Genome Analysis: Genetic and Physical Mapping*, 1, 39–81 (1990), Cold Spring Harbor Laboratory Press; Drmanac et al., *Nucl. Acids Res.*, 4691 (1986); Stevanovic et al., *Gene*, 79, 139 (1989); Panusku et al., *Mol. Biol. Evol.*, 1, 607 (1990); Nizetic et al., *Nucl. Acids Res.*, 19, 182 (1991); Drmanac et al., *J. Biomol. Struct. Dyn.*, 5, 1085 (1991); Hoheisel et al., *Mol. Gen.*, 4, 125–132 (1991); Strezoska et al., *Proc. Nat'l. Acad. Sci.* (USA), 88, 10089 (1991); Drmanac et al., *Nucl. Acids Res.*, 19, 5839 (1991); and Drmanac et al., *Int. J. Genome Res.*, 1, 59–79 (1992).

The term "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems described above.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1
Preparation of Sets of Probes

Two types of universal sets of probes may be prepared. The first is a complete set (or at least a noncomplementary subset) of relatively short probes, for example all 4096 (or about 2000 non-complementary) 6-mers, or all 16,384 (or about 8,000 non-complementary) 7-mers. Full noncomplementary subsets of 8-mers and longer probes are less convenient inasmuch as they include 32,000 or more probes.

A second type of probe set is selected as a small subset of probes still sufficient for reading every bp in any sequence with at least with one probe. For example, 12 of 16 dimers are sufficient. A small subset for 7-mers, 8-mer and 9-mers for sequencing double stranded DNA may be about 3000, 10,000 and 30,000 probes, respectively.

Sets of probes may also be selected to identify a target nucleic acid of known sequence, and/or to identify alleles or mutants of a target nucleic acid with a known sequence. Such a set of probes contains sufficient probes so that every nucleotide position of the target nucleic acid is read at least once. Alleles or mutants are identified by the loss of binding of one of the "positive" probes. The specific sequence of these alleles or mutants is then determined by interrogating the target nucleic acid with sets of probes that contain every possible nucleotide change and combination of changes at these probe positions.

Sets of probes may also be comprised of from 50 probes to a universal set of probes (all probes of a certain length), more preferably the set is comprised of 100–500 probes, and in a most preferred embodiment, the probe set contains 300 probes. In a preferred embodiment, the set of probes are 6–9 nucleotides in length, and are used to cluster cDNA clones into groups of similar or identical sequences, so that single representative clones may be selected from each group for sequencing.

Probes may be prepared using standard chemistry with one to three non-specified (mixed A,T,C and G) or universal (e.g. M base or inosine) bases at the ends. If radiolabelling is used, probes may have an OH group at the 5' end for kinasing by radiolabelled phosphorous groups. Alternatively, probes labelled with any compatible system, such as fluorescent dyes, may be employed. Other types of probes, such as PNA (Protein Nucleic Acids)or probes containing modified bases which change duplex stability also may be used.

Probes may be stored in bar-coded multiwell plates. For small numbers of probes, 96-well plates may be used; for 10,000 or more probes, storage in 384- or 864-well plates is preferred. Stacks of 5 to 50 plates are enough to store all probes. Approximately 5 pg of a probe may be sufficient for hybridization with one DNA sample. Thus, from a small synthesis of about 50 mg per probe, ten million samples may be analyzed. If each probe is used for every third sample, and if each sample is 1000 bp in length, then over 30 billion bases (10 human genomes) may be sequenced by a set of 5,000 probes.

EXAMPLE 2
Probes having Modified Oligonucleotides

Modified oligonucleotides may be introduced into hybridization probes and used under appropriate conditions therefor. For example, pyrimidines with a halogen at the $C^5$-position may be used to improve duplex stability by influencing base stacking. 2,6-diaminopurine may be used to provide a third hydrogen bond in base pairing with thymine, thereby thermally stabilizing DNA-duplexes. Using 2,5-diaminopurine may increase duplex stability to allow more stringent conditions for annealing, thereby improving the specificity of duplex formation, suppressing background problems and permitting the use of shorter oligomers.

The synthesis of the triphosphate versions of these modified nucleotides is disclosed by Hoheisel & Lehrach (1990).

One may also use the non-discriminatory base analogue, or universal base, as designed by Nichols et al. (1994). This new analogue, 1-(2-deoxy-D-ribfuranosyl)-3-nitropyrrole (designated M), was generated for use in oligonucleotide probes and primers for solving the design problems that arise as a result of the degeneracy of the genetic code, or when only fragmentary peptide sequence data are available. This analogue maximizes stacking while minimizing hydrogen-bonding interactions without sterically disrupting a DNA duplex.

The M nucleoside analogue was designed to maximize stacking interactions using aprotic polar substituents linked to heteroaromatic rings, enhancing intra- and inter-strand stacking interactions to lessen the role of hydrogen bonding in base-pairing specificity. Nichols et al. (1994) favored 3-nitropyrrole 2-deoxyribonucleoside because of its structural and electronic resemblance to p-nitroaniline, whose derivatives are among the smallest known intercalators of double-stranded DNA.

The dimethoxytrityl-protected phosphoramidite of nucleoside M is also available for incorporation into nucleotides used as primers for sequencing and polymerase chain reaction (PCR). Nichols et al. (1994) showed that a substantial number of nucleotides can be replaced by M without loss of primer specificity.

A unique property of M is its ability to replace long strings of contiguous nucleosides and still yield functional sequencing primers. Sequences with three, six and nine M substitutions have all been reported to give readable sequencing ladders, and PCR with three different M-containing primers all resulted in amplification of the correct product (Nichols et al., 1994).

The ability of 3-nitropyrrole-containing oligonucleotides to function as primers strongly suggests that a duplex structure must form with complementary strands. Optical thermal profiles obtained for the oligonucleotide pairs d(5-$C_2$-$T_5$X$T_5$$G_2$-3) and d(5-$C_2$$A_5$YA$_5$G2-3) (where X and Y can be A, C, G, T or M) were reported to fit the normal sigmoidal pattern observed for the DNA double-to single strand transition. The Tm values of the oligonucleotides containing X M base pairs (where X was A, C, G or T, and Y was M) were reported to all fall within a 3° C. range (Nichols et al., 1994).

EXAMPLE 3
Selection and Labeling of Probes

When an array of subarrays is produced, the sets of probes to be hybridized in each of the hybridization cycles on each of the subarrays is defined. For example, a set of 384 probes may be selected from the universal set, and 96 probings may be performed in each of 4 cycles. Probes selected to be hybridized in one cycle preferably have similar G+C contents.

Selected probes for each cycle are transferred to a 96-well plate and then are labelled by kinasing or by other labeling procedures if they are not labelled (e.g. with stable fluorescent dyes) before they are stored.

On the basis of the first round of hybridizations, a new set of probes may be defined for each of the subarrays for additional cycles. Some of the arrays may not be used in some of the cycles. For example, if only 8 of 64 patient samples exhibit a mutation and 8 probes are scored first for each mutation, then all 64 probes may be scored in one cycle and 32 subarrays are not used. These unused subarrays may then be treated with hybridization buffer to prevent drying of the filters.

Probes may be retrieved from the storing plates by any convenient approach, such as a single channel pipetting device, or a robotic station, such as a Beckman Biomek 1000 (Beckman Instruments, Fullerton, Calif.) or a Mega Two robot (Megamation, Lawrenceville, N.J.). A robotic station may be integrated with data analysis programs and probe managing programs. Outputs of these programs may be inputs for one or more robotic stations.

Probes may be retrieved one by one and added to subarrays covered by hybridization buffer. It is preferred that retrieved probes be placed in a new plate and labelled or mixed with hybridization buffer. The preferred method of retrieval is by accessing stored plates one by one and pipetting (or transferring by metal pins) a sufficient amount of each selected probe from each plate to specific wells in an intermediary plate. An array of individually addressable pipettes or pins may be used to speed up the retrieval process.

EXAMPLE 4
Preparation of Labeled Probes

The oligonucleotide probes may be prepared by automated synthesis, which is routine to those of skill in the art, for example, using and Applied Biosystems system. Alternatively, probes may be prepared using Genosys Biotechnologies Inc. Methods using stacks of porous Teflon wafers.

Oligonucleotide probes may be labeled with, for example, radioactive labels ($^{35}$S, $^{32}$P, $^{33}$P, and preferably, $^{33}$P) for arrays with 100–200 um or 100–400 um spots; non-radioactive isotopes (Jacobsen et al., 1990); or fluorophores (Brumbaugh et al., 1988). All such labeling methods are routine in the art, as exemplified by the relevant sections in Sambrook et al. (1989) and by further references such as Schubert et al. (1990), Murakami et al. (1991) and Cate et al. (1991), all articles being specifically incorporated herein by reference.

In regard to radiolabelling, the common methods are end-labeling using T4 polynucleotide kinase or high specific activity labeling using Klenow or even T7 polymerase. These are described as follows.

Synthetic oligonucleotides are synthesized without a phosphate group at their 5 termini and are therefore easily labeled by transfer of the -$^{32}$P or -$^{33}$P from [-$^{32}$P]ATP or [-$^{33}$P]ATP using the enzyme bacteriophage T4 polynucleotide kinase. If the reaction is carried out efficiently, the specificity activity of such probes can be as high as the specific activity of the [-$^{32}$P]ATP or [-$^{33}$P]ATP itself. The reaction described below is designed to label 10 pmoles of an oligonucleotide to high specific activity. Labeling of different amounts of oligonucleotide can easily be achieved by increasing or decreasing the size of the reaction, keeping the concentrations of all components constant.

A reaction mixture would be created using 1.0 ul of oligonucleotide (10 pmoles/ul); 2.0 ul of 10× bacteriophage T4 polynucleotide kinase buffer; 5.0 ul of [-$^{32}$P]ATP or [-$^{33}$P]ATP (sp. Act. 5000 Ci/mmole; 10 mCi/ml in aqueous solution) (10 pmoles); and 11.4 ul of water. Eight (8) units (~1 ul) of bacteriophage T4 polynucleotide kinase is added to the reaction mixture, and incubated for 45 minutes at 37° C. The reaction is heated for 10 minutes at 68° C. to inactivate the bacteriophage T4 polynucleotide kinase.

The efficiency of transfer of $^{32}P$ or $^{33}P$ to the oligonucleotide and its specific activity is then determined. If the specific activity of the probe is acceptable, it is purified. If the specific activity is too low, an additional 8 units of enzyme is added and incubated for a further 30 minutes at 37° C. before heating the reaction for 10 minutes at 68° C. to inactivate the enzyme.

Purification of radiolabeled oligonucleotides can be achieved by, e.g., precipitation with ethanol; precipitation with cetylpyridinium bromide; by chromatography through bio-gel P-60; or by chromatography on a Sep-Pak $C_{18}$ column, or by polyacrylamide gel electrophoresis.

Probes of higher specific activities can be obtained using the Klenow fragment of E. coli. DNA polymerase I to synthesize a strand of DNA complementary to the synthetic oligonucleotide. A short primer is hybridized to an oligonucleotide template whose sequence is the complement of the desired radiolabeled probe. The primer is then extended using the Klenow fragment of E. coli DNA polymerase I to incorporate [-$^{32}P$]dNTPs or [-$^{33}P$]dNTPs in a template-directed manner. After the reaction, the template and product are separated by denaturation followed by electrophoresis through a polyacrylamide gel under denaturing conditions. With this method, it is possible to generate oligonucleotide probes that contain several radioactive atoms per molecule of oligonucleotide.

To use this method, one would mix in a microfuge tube the calculated amounts of [a-32P]dNTPs or [a-33P]dNTPs necessary to achieve the desired specific activity and sufficient to allow complete synthesis of all template strands. Then add to the tube the appropriate amounts of primer and template DNAs, with the primer being in three- to tenfold molar excess over the template.

0.1 volume of 10×Klenow buffer would then be added and mixed well. 2–4 units of the Klenow fragment of E. coli DNA polymerase I would then be added per 5 ul of reaction volume, mixed and incubated for 2–3 hours at 4° C. If desired, the process of the reaction may be monitored by removing small (0.1 ul) aliquots and measuring the proportion of radioactivity that has become precipitable with 10% trichloroacetic acid (TCA).

The reaction would be diluted with an equal volume of gel-loading buffer, heated to 80° C. for 3 minutes, and then the entire sample loaded on a denaturing polyacrylamide gel. Following electrophoresis, the gel is autoradiographed, allowing the probe to be localized and removed from the gel. Various methods for fluorescent probe labeling are also available, e.g., Brumbaugh et al. (1988) describe the synthesis of fluorescently labeled primers. A deoxyuridine analog with a primary amine "linker arm" of 12 atoms attached at C-5 is synthesized. Synthesis of the analog consists of derivatizing 2-deoxyuridine through organometallic intermediates to give 5 (methyl propenoyl)-2-deoxyuridine. Reaction with dimethoxytrityl-chloride produces the corresponding 5-dimethoxytrityl adduct. The methyl ester is hydrolyzed, activated, and reacted with an appropriately monoacylated alkyl diamine. After purification, the resultant linker arm nucleosides are converted to nucleoside analogs suitable for chemical oligonucleotide synthesis.

Oligonucleotides would then be made that include one or two linker arm bases by using modified phosphoridite chemistry. To a solution of 50 nmol of the linker arm oligonucleotide in 25 ul of 500 mM sodium biocarbonate (pH 9.4) is added 20 ul of 300 mM FITC in dimethyl sulfoxide. The mixture is agitated at room temperature for 6 hrs. The oligonucleotide is separated from free FITC by elution form a 1×30 cm Sephadex G-25 column with 20 mM ammonium acetate (pH 6), combining fractions in the first Uv-absorbing peak.

In general, fluorescent labeling of an oligonucleotide at its 5'-end initially involved two steps. First, a N-protected aminoalkyl phosphoramidite derivative is added to the 5'-end of an oligonucleotide during automated nucleic acid synthesis. After removal of all protecting groups, the NHS ester of an appropriate fluorescent dye is coupled to the 5'-amino group overnight followed by purification of the labeled oligonucleotide from the excess of dye using reverse phase HPLC or PAGE.

Schubert et al. (1990) described the synthesis of a phosphoramidite that enables oligonucleotides labeled with fluorescein to be produced during automated DNA synthesis.

Murakami et al. also described the preparation of flourescein-labeled oligonucleotides.

Cate et al. (1991) describe the use of oligonucleotide probes directly conjugated to alkaline phosphatase in combination with a direct chemiluminescent substrate (AMPPD) to allow probe detection.

Labeled probes could readily be purchased form a variety of commercial sources, including GENSET, rather then synthesized.

Other labels include ligands which can serve as specific binding members to a labeled antibody, chemiluminescers, enzymes, antibodies which can serve as a specific binding pair member for a labeled ligand, and the like. A wide variety of labels have been employed in immunoassays which can readily be employed. Still other labels include antigens, groups with specific reactivity, and electrochemically detectable moeities.

In general, labeling of nucleic acids with electrophore mass labels ("EML") is described, for example, in Xu et al., J. Chromatography 764:95–102 (1997). Electrophores are compounds that can be detected with high sensitivity by electron capture mass spectrometry (EC-MS). EMLs can be attached to a probe using chemistry that is well known in the art for reversibly modifying a nucleotide (e.g., well known nucleotide synthesis chemistry teaches a variety of methods for attaching molecules to nucleotides as protecting groups). EMLs are detected using a variety of well known electron capture mass spectrometry devices (e.g., devices sold by Finnigan Corporation). Further, techniques that may be used in the detection of EMLs include, for example, fast atomic bombardment mass spectrometry (see, e.g., Koster et al., Biomedical Environ. Mass Spec. 14:111– 116 (1987)); plasma desorption mass spectrometry; electrospray/ionspray (see, e.g., Fenn et al., J. Phys. Chem. 88:4451–59 (1984), PCT Appln. No. WO 90/14148, Smith et al., Anal. Chem. 62:882–89 (1990)); and matrix-assisted laser desorption/ ionization (Hillenkamp, et al., "Matrix Assisted UV-Laser Desorption/Ionization: A New Approach to Mass Spectrometry of Large Biomolecules," *Biological Mass Spectrometry* (Burlingame and McCloskey, eds.), Elsevier Science Publishers, Amsterdam, pp. 49–60, 1990); Huth-Fehre et al., "Matrix Assisted Laser Desorption Mass Spectrometry of Oligodeoxythymidylic Acids," *Rapid Communications in Mass Spectrometry,* 6:209–13 (1992)).

In preferred embodiments, the EMLs are attached to a probe by a covalent bond that is light sensitive. The EML is released from the probe after hybridization with a target nucleic acid by a laser or other light source emitting the desired wavelength of light. The EML is then fed into a GC-MS (gas chromatograph-mass spectrometer) or other appropriate device, and identified by its mass.

EXAMPLE 5
Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45 u pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al. (1989) also used ISO-GRID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 uM/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula $B_xN_n$, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as $(N)_nB_x(N)_m$.

In another embodiment of the chips, the substrate which supports the array of oligonucleotide probes is partitioned into sections so that each probe in the array is separated from adjacent probes by a physical barrier which may be, for example, a hydrophobic material. In a preferred embodiment, the physical barrier has a width of from 300 $\mu$m to 30 $\mu$m, and the distance between the center of each physical barrier to the center of adjacent physical barriers is at least 325 $\mu$m.

In a preferred embodiment, a hydrophobic material is deposited onto the substrate to form barriers of the desired width using an ink-jet head, coupled to an appropriate robotic system. For example a microdrop dosing head, that has been adapted to apply a suspension or solution of a desired hydrophobic material (e.g., an oil based material that forms a barrier after the solvent has evaporated), may be coupled with an anorad gantry system and fitted to an appropriate housing and dispensing system so that a grid of the hydrophobic material may be applied onto the desired substrate forming a plurality of wells on the substrate. After the grid of hydrophobic material has been formed, different probes are spotted onto each well (or mixtures of probes may be applied to each well) using a robotic system similar to that used to form the grid, but that has been adapted to apply solutions or suspensions of probes. In one embodiment, the same robotic system is used to apply the hydrophobic grid and the probes. In this embodiment, the dispensing system is flushed after the hydrophobic grid is applied and then primed for delivery of probe.

EXAMPLE 6
Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

In general, oligonucleotides may be bound to a support through appropriate reactive groups. Such groups are well known in the art and include, for example, amino (—$NH_2$); hydroxyl (—OH); or carboxyl ($CO_2H$) groups. Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved by many methods, including, for example, using passive adsorption (Inouye & Hondo, 1990); using UV light (Nagata et al., 1985; Dahlen et al., 1987; Morriey & Collins, 1989); or by covalent binding of base modified DNA (Keller et al., 1988; 1989); or by formation of amide groups between the probe and the support (Wall et al., 1995; Chebab et al., 1992; and Zhang et al., 1991); all references being specifically incorporated herein.

Another strategy that may be employed is the use of the strong biotin-streptavidin interaction as a linker. For example, Broude et al. (1994) describe the use of Biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al. (1991); or linked to Teflon using the method of Duncan & Cavalier (1988); all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

Of course, one could easily purchase a DNA chip, such as one of the light-activated chips described above, from a commercial source. In this regard, one may contact Affymetrix of Santa Clara, Calif. 95051, and Beckman.

In a preferred embodiment, the probes of the invention include an informational portion (the portion which hybridizes to the target nucleic acid and gives sequence information) a reactive group to be attached to the substrate (solid support), and randomized positions, i.e., any of the four bases may be found at these positions. A preferred probe has the sequence 5'-(T)$_6$-(N)$_3$-(B)$_5$, where T=thymine (binds to solid support), N=A, C, G, or T (randomized positions), and B=the five information positions of the probe (informational portion). In a most preferred embodiment, the probe may be bound to the support and a spacer moiety is found at the end of the probe or internal to the probe and 5' of (N)$_3$. The spacers may be comprised of atoms capable of forming at least two covalent bonds such as carbon, silicon, oxygen, sulfur, phosphorous, and the like, or may be comprised of molecules capable of forming at least two covalent bonds such as sugar-phosphate groups, amino acids, peptides, nucleosides, nucleotides, sugars, carbohydrates, aromatic rings, hydrocarbon rings, linear and branched hydrocarbons, and the like.

EXAMPLE 7

Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including MRNA without any amplification steps. For example, Sambrook et al. (1989) describes three protocols for the isolation of high molecular weight DNA from mammalian cells (p. 9.14–9.23).

Target nucleic acid fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume. Target nucleic acids prepared by PCR may be directly applied to a substrate for Format I SBH without purification. Once the target nucleic acids are fixed to the substrate, the substrate may be washed or directly annealed with probes.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed). These advantages are also proposed to be of use when preparing DNA for sequencing by Format 3.

In a preferred embodiment, the "fragments" of the nucleic acid sample are prepared so that they cannot be ligated to each other. Such a pool of fragments may be obtained by treating the fragmented nucleic acids obtained by enzyme digestion or physical shearing, with a phosphatase (e.g., calf intestinal phosphatase). Alternatively, nonligatable fragments of the sample nucleic acid may be obtained by using random primers (e.g., $N_5$–$N_9$, where N=A, G, T, or C), which have no phosphate at their 5'-ends, in a Sanger-dideoxy sequencing reaction with the sample nucleic acid. This will produce fragments of DNA that have a complementary sequence to the target nucleic acid and that are terminated in a dideoxy residue and which cannot be ligated to other fragments.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip.

EXAMPLE 8
Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 $mm^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 $mm^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

EXAMPLE 9
Hybridization and Scoring Process

Labeled probes may be mixed with hybridization buffer and pipetted, preferably by multichannel pipettes, to the subarrays. To prevent mixing of the probes between subarrays (if there are no hydrophobic strips or physical barriers imprinted in the membrane), a corresponding plastic, metal or ceramic grid may be firmly pressed to the membrane. Also, the volume of the buffer may be reduced to about 1 ml or less per $mm^2$. The concentration of the probes and hybridization conditions used may be as described previously except that the washing buffer may be quickly poured over the array of subarrays to allow fast dilution of probes and thus prevent significant cross-hybridization. For the same reason, a minimal concentration of the probes may be used and hybridization time extended to the maximal practical level. For DNA detection and sequencing, knowledge of a "normal" sequence allows the use of the continuous stacking interaction phenomenon to increase the signal. In addition to the labelled probe, additional unlabelled probes which hybridize back to back with a labelled one may be added in the hybridization reaction. The amount of the hybrid may be increased several times. The probes may be connected by ligation. This approach may be important for resolving DNA regions forming "compressions".

In the case of radiolabelled probes, images of the filters may be obtained, preferably by phosphorstorage technology. Fluorescent labels may be scored by CCD cameras, confocal microscopy or otherwise. In order to properly scale and integrate data from different hybridization experiments, raw signals are normalized based on the amount of target in each dot. Differences in the amount of target DNA per dot may be corrected for by dividing signals of each probe by an average signal for all probes scored on one dot. The normalized signals may be scaled, usually from 1–100, to compare data from different experiments. Also, in each subarray, several control DNAs may be used to determine an average background signal in those samples which do not contain a full match target. For samples obtained from diploid (polyploid) scores, homozygotic controls may be used to allow recognition of heterozygotes in the samples.

EXAMPLE 10

Hybridization with Oligonucleotides

Oligonucleotides were either purchased from Genosys Inc., Houston, Tex. or made on an Applied Biosystems 381A DNA synthesizer. Most of the probes used were not purified by HPLC or gel electrophoresis. For example, probes were designed to have both a single perfectly complementary target in interferon, a M13 clone containing a 921 bp Eco RI-Bgl II human B1-interferon fragment (Ohno and Tangiuchi, Proc. Natl. Acad. Sci. 74: 4370–4374 (1981)], and at least one target with an end base mismatch in M13 vector itself.

End labeling of oligonucleotides was performed as described [Maniatis et al., *Molecular Cloning: A Laboratory Manual,* Cold Spring Harbor Laboratory Cold Spring Harbor, N.Y. (1982)] in 10 ml containing T4-polynucleotide kinase (5 units Amersham), $\gamma^{32P}$-ATP (3.3 pM, 10 mCi Amersham 3000 Ci/mM) and oligonucleotide (4 pM, 10 ng). Specific activities of the probes were 2.5–5×10 9 cpm/nM.

Single stranded DNA (2 to 4 ml in 0.5 NaOH, 1.5 M NaCl) was spotted on a Gene Screen membrane wetted with the same solution, the filters were neutralized in 0.05 M $Na_2HPO_4$ pH 6.5, baked in an oven at 80° C. for 60 min. and UV irradiated for 1 min. Then, the filters were incubated in hybridization solution (0.5 M $Na_2HPO_4$ pH 7.2, 7% sodium lauroyl sarcosine for 5 min at room temperature and placed on the surface of a plastic Petri dish. A drop of hybridization solution (10 ml, 0.5 M $Na_2HPO_4$ pH 7.2, 7% sodium lauroyl sarcosine) with a $^{32}P$ end-labeled oligomer probe at 4 nM concentration was placed over 1–6 dots per filter, overlaid with a square piece of polyethylene (approximately 1×1 cm.), and incubated in a moist chamber at the indicated temperatures for 3 hr. Hybridization was stopped by placing the filter in 6×SSC washing solution for 3×5 minute at 0° C. to remove unhybridized probe. The filter was either dried, or further washed for the indicated times and temperatures, and autoradiographed. For discrimination measurements, the dots were excised from the dried filters after autoradiography [a phosphoimager (Molecular Dynamics, Sunnyvale, Calif.) may be used] placed in liquid scintillation cocktail and counted. The uncorrected ratio of cpms for IF and M13 dots is given as D.

The conditions reported herein allow hybridization with very short oligonucleotides but ensure discriminations between matched and mismatched oligonucleotides that are complementary to and therefore bind to a target nucleic acid. Factors which influence the efficient detection of hybridization of specific short sequences based on the degree of discriminations (D) between a perfectly complementary target and an imperfectly complementary target with a single mismatch in the hybrid are defined. In experimental tests, dot blot hybridization of twenty-eight probes that were 6 to 8 nucleotides in length to two M13 clones or to model oligonucleotides bound to membrane filters was accomplished. The principles guiding the experimental procedures are given below.

Oligonucleotide hybridization to filter bound target nucleic acids only a few nucleotides longer than the probe in conditions of probe excess is a pseudo-first order reaction with respect to target concentration. This reaction is defined by:

$$S_t/S_o = e^{-k_h[OP]t}$$

Wherein $S_t$ and $S_o$ are target sequence concentrations at time t and to, respectively. (OP) is probe concentration and t is temperature. The rate constant for hybrid formation, $k_h$ increases only slightly in the 0° C. to 30° C. range (Porschke and Eigen, *J. Mol. Biol.* 62: 361 (1971); Craig et al., *J. Mol. Biol.* 62: 383 (1971)]. Hybrid melting is a first order reaction with respect to hybrid concentration (here replaced by mass due to filter bound state) as shown in:

$$H_t/H_o = e^{-k_m t}$$

In this equation, $H_t$ and $H_o$ are hybrid concentrations at times t and $t_o$, respectively; $k_m$ is a rate constant for hybrid melting which is dependent on temperature and salt concentration [Ikuta et al., *Nucl. Acids Res.* 15: 797 (1987); Porsclike and Eigen, *J. Mol. Biol.* 62: 361 (1971); Craig et al., J. Mol. Biol. 62: 303 (1971)]. During hybridization, which is a strand association process, the back, melting, or strand dissociation, reaction takes place as well. Thus, the amount of hybrid formed in time is result of forward and back reactions. The equilibrium may be moved towards hybrid formation by increasing probe concentration and/or decreasing temperature. However, during washing cycles in large volumes of buffer, the melting reaction is dominant and the back reaction hybridization is insignificant, since the probe is absent. This analysis indicates workable Short Oligonucleotide Hybridization (SOH) conditions call be varied for probe concentration or temperature.

D or discrimination is defined in equation four:

$$D = H_p(t_w)/H_i(t_w)$$

$H_p(t_w)$ and $H_i(t_w)$ are the amounts hybrids remaining after a washing time, $t_w$, for the identical amounts of perfectly and imperfectly complementary duplex, respectively. For a given temperature, the discrimination D changes with the 10 length of washing time and reaches the maximal value when $H_i=B$ which is equation five.

The background, B, represents the lowest hybridization signal detectable in the system. Since any further decrease of $H_i$ may not be examined, D increases upon continued washing. Washing past $t_w$ just decreases $H_p$ relative to B, and is seen as a decrease in D. The optimal washing time, $t_w$, for imperfect hybrids, from equation three and equation five is:

$$t_w = -\ln(B/H_i(t_0))/k_{m,i}$$

Since $H_p$ is being washed for the same $t_w$, combining equations, one obtains the optimal discrimination function:

$$D = e \ln(B/Hi(t0))km,p/km,i \times H_p(t_0)/B$$

The change of D as a function, of T is important because of the choice of an optimal washing temperature. It is obtained by substituting the Arhenius equation which is:

$$K = A e^{-Ea/RT}$$

into the previous equation to form the final equation:

$$D = H_p((t_0)/B \times (B/H_i(t_0))(Ap/Ai)e^{(E_{a,i}-E_{a,p})/RT};$$

Wherein B is less than $H_i(t_0)$.

Since the activation energy for perfect hybrids, $E_{a,p}$, and the activation energy for imperfect hybrids, $E_{a,i}$, can be either equal, or $E_{a,i}$ less than $E_{a,p}$ D is temperature independent, or decreases with increasing temperature, respectively. This result implies that the search for stringent temperature conditions for good discrimination in SOH is unjustified. By washing at lower temperatures, one obtains equal or better discrimination, but the time of washing exponentially increases with the decrease of temperature. Discrimination more strongly decreases with T, if $H_i(t_0)$ increases relative to $H_p$ ($t_0$).

D at lower temperatures depends to a higher degree on the $H_p$ ($t_0$)/B ratio than on the $H_p$ ($t_0$)/$H_i$ ($t_0$) ratio. This result indicates that it is better to obtain a sufficient quantity of $H_p$ in the hybridization regardless of the discrimination that can be achieved in this step. Better discrimination can then be obtained by washing, since the higher amounts of perfect hybrid allow more time for differential melting to show an effect. Similarly, using larger amounts of target nucleic acid a necessary discrimination can be obtained even with small differences between $K_{m,p}$ and $K_{m,i}$.

Extrapolated to a more complex situation than covered in this simple model, the result is that washing at lower temperatures is even more important for obtaining discrimination in the case of hybridization of a probe having many end-mismatches within a given nucleic acid target.

Using the described theoretical principles as a guide for experiments, reliable hybridizations have been obtained with probes six to eight nucleotides in length. All experiments were performed with a floating plastic sheet providing a film of hybridization solution above the filter. This procedure allows maximal reduction in the amount of probe, and thus reduced label costs in dot blot hybridizations. The high concentration of sodium lauroyl sarcosine instead of sodium lauroyl sulfate in the phosphate hybridization buffer allows dropping the reaction from room temperature down to 12° C. Similarly, the 4–6×SSC, 10% sodium lauroyl sarcosine buffer allows hybridization at temperatures as low as 2° C. The detergent in these buffers is for obtaining tolerable background with up to 40 nM concentrations of labelled probe. Preliminary characterization of the thermal stability of short oligonucleotide hybrids was determined on a prototype octamer with 50% G+C content, i.e. probe of sequence TGCTCATG. The theoretical expectation is that this probe is among the less stable octamers. Its transition enthalpy is similar to those of more stable heptamers or, even to probes 6 nucleotides in length (Bresslauer et al., *Proc. Natl. Acad. Sci.* U.S.A. 83: 3746 (1986)). Parameter $T_d$, the temperature at which 50% of the hybrid is melted in unit time of a minute is 18° C. The result shows that $T_d$ is 15° C. lower for the 8 bp hybrid than for an 11 bp duplex [Wallace et al., *Nucleic Acids Res.* 6: 3543 (1979)].

In addition to experiments with model oligonucleotides, an M13 vector was chosen as a system for a practical demonstration of short oligonucleotide hybridization. The main aim was to show useful end-mismatch discrimination with a target similar to the ones which will be used in various applications of the method of the invention. Oligonucleotide probes for the M13 model were chosen in such a way that the M13 vector itself contains the end mismatched base. Vector IF, an M13 recombinant containing a 921 bp human interferon gene insert, carries single perfectly matched target. Thus, IF has either the identical or a higher number of mismatched targets in comparison to the M13 vector itself.

Using low temperature conditions and dot blots, sufficient differences in hybridization signals were obtained between tie dot containing the perfect and the mismatched targets and the dot containing the mismatched targets only. This was true for the 6-mer oligonucleotides and was also true for the 7 and 8-mer oligonucleotides hybridized to the large IF-M13 pair of nucleic acids.

The hybridization signal depends on the amount of target available on the filter for reaction with the probe. A necessary control is to show that the difference in sign intensity is not a reflection of varying amounts of nucleic acid in the two dots. Hybridization with a probe that has the same number and kind of targets in both IF and M13 shows that there is an equal amount of DNA in the dots. Since the efficiency of hybrid formation increases with hybrid length, the signal for a duplex having six nucleotides was best detected with a high mass of oligonucleotide target bound to the filter. Due to their lower molecular weight, a larger number of oligonucleotide target molecules can be bound to a given surface area when compared to large molecules of nucleic acid that serves as target.

To measure the sensitivity of detection with unpurified DNA, various amounts of phage supernatants were spotted on the filter and hybridized with a $^{32}$P-labelled octamer. As little as 50 million unpurified phage containing no more than 0.5 ng of DNA gave a detectable signal indicating that sensitivity of the short oligonucleotide hybridization method is sufficient. Reaction time is short, adding to the practicality.

As mentioned in the theoretical section above, the equilibrium yield of hybrid depends oil probe concentration and/or temperature of reaction. For instance, the signal level for the same amount of target with 4 nM octamer at 13° C. is 3 times lower than with a probe concentration of 40 nM, and is decreased 4.5-times by raising the hybridization temperature to 25° C.

The utility of the low temperature wash for achieving maximal discrimination is demonstrated. To make the phenomenon visually obvious, 50 times more DNA was put in the M13 dot than in the IF dot using hybridization with a vector specific probe. In this way, the signal after the hybridization step with the actual probe was made stronger in the, mismatched that in the matched case. The $H_p/H_i$ ratio was 1:4. Inversion of signal intensities after prolonged washing at 7° C. was achieved without a massive loss of perfect hybrid, resulting in a ratio of 2:1. In contrast, it is impossible to achieve any discrimination at 25° C., since the matched target signal is already brought down to the background level with 2 minute washing; at the same time, the signal from the mismatched hybrid is still detectable. The loss of discrimination at 13° C. compared to 7° C. is not so great but is clearly visible. If one considers the 90 minute point at 7° C. and the 15 minute point at 13° C. when, the mismatched hybrid signal is near the background level, which represents optimal washing times for the respective conditions, it is obvious that the amount of several times greater at 7° C. than at 13° C. To illustrate this further, the time course of the change discrimination with washing of the same amount of starting hybrid at the two temperatures shows the higher maximal D at the lower temperature. These results confirm the trend in the change of D with temperature and the ratio of amounts of the two types of hybrid at the start of the washing step.

In order to show the general utility of the short oligonucleotide hybridization conditions, we have looked hybridization of 4 heptamers, 10 octamers and an additional 14 probes up to 12 nucleotides in length in our simple M13 system. These include-the nonamer GTTTTTTAA and octamer GGCAGGCG representing the two extremes of GC content. Although GC content and sequence are expected to influence the stability of short hybrids [Bresslauer et al., *Proc. Natl. Acad. Sci.* U.S.A. 83: 3746 (1986)], the low temperature short oligonucleotide conditions were applicable to all tested probes in achieving sufficient discrimination. Since the best discrimination value obtained with probes 13 nucleotides in length was 20, a several fold drop due to sequence variation is easily tolerated.

The M13 system has the advantage of showing the effects of target DNA complexity on the levels of discrimination. For two octamers having either none or five mismatched targets and differing in only one GC pair the observed discriminations were 18.3 and 1.7, respectively.

In order to show the utility of this method, three probes 8 nucleotides in length were tested on a collection of 51 plasmid DNA dots made from a library in Bluescript vector. One probe was present and specific for Bluescript vector but was absent in M13, while the other two probes had targets that were inserts of known sequence. This system allowed the use of hybridization negative or positive control DNAs with each probe. This probe sequence (CTCCCTTT) also had a complementary target in the interferon insert. Since the M13 dot is negative while the interferon insert in either M13 or Bluescript was positive, the hybridization is sequence specific. Similarly, probes that detect the target sequence in only one of 51 inserts, or in none of the examined inserts along with controls that confirm that hybridization would have occurred if the appropriate targets were present in the clones.

Thermal stability curves for very short oligonucleotide hybrids that are 6–8 nucleotides in length are at least 15° C. lower than for hybrids 11–12 nucleotides in length [Wallace et al., *Nucleic Acids Res.* 6: 3543–3557 (1979)]. However, performing the hybridization reaction at a low temperature and with a very practical 0.4–40 nM concentration of oligonucleotide probe allows the detection of complementary sequence in a known or unknown nucleic acid target. To determine an unknown nucleic acid sequence completely, an entire set containing 65,535 8-mer probes may be used. Sufficient amounts of nucleic acid for this purpose are present in convenient biological samples such as a few microliters of M13 culture, a plasmid prep from 10 ml of bacterial culture or a single colony of bacteria, or less than 1 ml of a standard PCR reaction.

Short oligonucleotides 6–10 nucleotides long give excellent discrimination. The relative decrease in hybrid stability with a single end mismatch is greater than for longer probes. Results with the octamer TGCTCATG support this conclusion. In the experiments, the target with a G/T end mismatch, hybridization to the target of this type of mismatch is the most stable of all other types of oligonucleotide. This discrimination achieved is the same as or greater than an internal G/T mismatch in a 19 base paired duplex greater than an internal G/T mismatch in a 19 paired duplex [Ikuta et al., Nucl. Acids res. 15: 797 (1987)]. Exploiting these discrimination properties using the described hybridization conditions for short oligonucleotide hybridization allows a very precise determination of oligonucleotide targets. In contrast to the ease of detecting discrimination between perfect and imperfect hybrids, a problem that may exist with using very short oligonucleotides is the preparation of sufficient amounts of hybrids. In practice, the need to discriminate $H_p$ and $H_i$ is aided by increasing the amount of DNA in the dot and/or the probe concentration, or by decreasing the hybridization temperature. However, higher probe concentrations usually increase background. Moreover, there are limits to the amounts of target nucleic acid that are practical to use. This problems was solved by the higher concentration of the detergent Sarcosyl which gave an effective background with 4 nM of probe. Further improvements may be effected either in the use of competitors for unspecific binding of probe to filter, or by changing the hybridization support material. Moreover, for probes having $E_a$ less than 45 Kcal/mol (e.g. for many heptamers and a majority of hexamers, modified oligonucleotides give a more stable hybrid [Asseline, et al., *Proc. Nat'l Acad. Sci.* 81: 3297 (1984)] than their unmodified counterparts. The hybridization conditions described in this invention for short oligonucleotide hybridization using low temperatures give better discriminating for all sequences and duplex hybrid inputs. The only price paid in achieving uniformity in hybridization conditions for different sequences is an increase in washing time from minutes to up to 24 hours depending on the sequence. Moreover, the washing time can be further reduced by decreasing the salt concentration.

Although there is excellent discrimination of one matched hybrid over a mismatched hybrids, in short oligonucleotide hybridization, signals from mismatched hybrids exist, with the majority of the mismatch hybrids resulting from end mismatch. This may limit insert sizes that may be effectively examined by a probe of a certain length.

The influence of sequence complexity on discrimination cannot be ignored. However, the complexity effects are more significant when defining sequence information by short oligonucleotide hybridization for specific, nonrandom sequences, and can be overcome by using an appropriate probe to target length ratio. The length ratio is chosen to make unlikely, on statistical grounds, the occurrence of specific sequences which have a number of end-mismatches which would be able to eliminate or falsely invert discrimination. Results suggest the use of oligonucleotides 6, 7, and 8 nucleotides in length on target nucleic acid inserts shorter than 0.6, 2.5, and 10 kb, respectively.

EXAMPLE 11

DNA Sequencing

An array of subarrays allows for efficient sequencing of a small set of samples arrayed in the form of replicated subarrays; For example, 64 samples may be arrayed on a 8×8 mm subarray and 16×24 subarrays may be replicated on a 15×23 cm membrane with 1 mm wide spacers between the subarrays. Several replica membranes may be made. For example, probes from a universal set of three thousand seventy-two 7-mers may be divided in thirty-two 96-well plates and labelled by kinasing. Four membranes may be processed in parallel during one hybridization cycle. On each membrane, 384 probes may be scored. All probes may be scored in two hybridization cycles. Hybridization intensities may be scored and the sequence assembled as described below.

If a single sample subarray or subarrays contains several unknowns, especially when similar samples are used, a smaller number of probes may be sufficient if they are intelligently selected on the basis of results of previously scored probes. For example, if probe AAAAAAA is not positive, there is a small chance that any of 8 overlapping probes are positive. If AAAAAAA is positive, then two probes are usually positive. The sequencing process in this case consists of first hybridizing a subset of minimally overlapped probes to define positive anchors and then to successively select probes which confirms one of the most likely hypotheses about the order of anchors and size and type of gaps between them. In this second phase, pools of 2–10 probes may be used where each probe is selected to be positive in only one DNA sample which is different from the samples expected to be positive with other probes from the pool.

The subarray approach allows efficient implementation of probe competition (overlapped probes) or probe cooperation (continuous stacking of probes) in solving branching problems. After hybridization of a universal set of probes the sequence assembly program determines candidate sequence subfragments (SFs). For the further assembly of SFs, additional information has to be provided (from overlapped sequences of DNA fragments, similar sequences, single pass gel sequences, or from other hybridization or restriction mapping data). Primers for single pass gel sequencing through the branch points are identified from the SBH sequence information or from known vector sequences, e.g., the flanking sequences to the vector insert site, and standard Sanger-sequencing reactions are performed on the sample DNA. The sequence obtained from this single pass gel sequencing is compared to the Sfs that read into and out of the branch points to identify the order of the Sfs. Further, singe pass gel sequencing may be combined with SBH to de novo sequence or re-sequence a nucleic acid.

Competitive hybridization and continuous stacking interactions can also be used to assemble Sfs. These approaches are of limited commercial value for sequencing of large numbers of samples by SBH wherein a labelled probe is applied to a sample affixed to an array if a uniform array is used. Fortunately, analysis of small numbers of samples using replica subarrays allows efficient implementation of both approaches. On each of the replica subarrays, one branching point may be tested for one or more DNA samples using pools of probes similarly as in solving mutated sequences in different samples spotted in the same subarray (see above).

If in each of 64 samples described in this example, there are about 100 branching points, and if 8 samples are analyzed in parallel in each subarray, then at least 800 subarray probings solve all branches. This means that for the 3072 basic probings an additional 800 probings (25%) are employed. More preferably, two probings are used for one branching point. If the subarrays are smaller, less additional probings are used. For example, if subarrays consist of 16 samples, 200 additional probings may be scored (6%). By using 7-mer probes ($N_{1-2}B_7N_{1-2}$) and competitive or collaborative branching solving approaches or both, fragments of about 1000 bp fragments may be assembled by about 4000 probings. Furthermore, using 8-mer probes ($NB_8N$) 4 kb or longer fragments may be assembled with 12,000 probings. Gapped probes, for example, $NB_4NB_3N$ or $NB_4NB_4N$ may be used to reduce the number of branching points.

EXAMPLE 12

DNA Analysis by Transient Attachment to Subarrays of Probes and Ligation of Labelled Probes Oligonucleotide probes having an informative length of four to 40 bases are synthesized by standard chemistry and stored in tubes or in multiwell plates. Specific sets of probes comprising one to 10,000 probes are arrayed by deposition or in situ synthesis on separate supports or distinct sections of a larger support. In the last case, sections or subarrays may be separated by physical or hydrophobic barriers. The probe arrays may be prepared by in situ synthesis. A sample DNA of appropriate size is hybridized with one or more specific arrays. Many samples may be interrogated as pools at the same subarrays or independently with different subarrays within one support. Simultaneously with the sample or subsequently, a single labelled probe or a pool of labelled probes is added on each of the subarrays. If attached and labelled probes hybridize back to back on the complementary target in the sample DNA they are ligated. Occurrence of ligation will be measured by detecting a label from the probe.

This procedure is a variant of the described DNA analysis process in which DNA samples are not permanently attached to the support. Transient attachment is provided by probes fixed to the support. In this case there is no need for a target DNA arraying process. In addition, ligation allows detection of longer oligonucleotide sequences by combining short labelled probes with short fixed probes.

The process has several unique features. Basically, the transient attachment of the target allows its reuse. After ligation occur the target may be released and the label will stay covalently attached to the support. This feature allows cycling the target and production of detectable signal with a small quantity of the target. Under optimal conditions, targets do not need to be amplified, e.g. natural sources of the DNA samples may be directly used for diagnostics and sequencing purposes. Targets may be released by cycling the temperature between efficient hybridization and efficient melting of duplexes. More preferably, there is no cycling. The temperature and concentrations of components may be defined to have an equilibrium between free targets and targets entered in hybrids at about 50:50% level. In this case there is a continuous production of ligated products. For different purposes different equilibrium ratios are optimal.

An electric field may be used to enhance target use. At the beginning, a horizontal field pulsing within each subarray may be employed to provide for faster target sorting. In this phase, the equilibrium is moved toward hybrid formation, and unlabelled probes may be used. After a target sorting phase, an appropriate washing (which may be helped by a vertical electric field for restricting movement of the samples) may be performed. Several cycles of discriminative hybrid melting, target harvesting by hybridization and ligation and removing of unused targets may be introduced to increase specificity. In the next step, labelled probes are added and vertical electrical pulses may be applied. By increasing temperature, an optimal free and hybridized target ratio may be achieved. The vertical electric field prevents diffusion of the sorted targets.

The subarrays of fixed probes and sets of labelled probes (specially designed or selected from a universal probe set) may be arranged in various ways to allow an efficient and flexible sequencing and diagnostics process. For example, if a short fragment (about 100–500 bp) of a bacterial genome is to be partially or completely sequenced, small arrays of probes (5–30 bases in length) designed on the bases of known sequence may be used. If interrogated with a different pool of 10 labelled probes per subarray, an array of 10 subarrays each having 10 probes, allows checking of 200 bases, assuming that only two bases connected by ligation are scored. Under the conditions where mismatches are discriminated throughout the hybrid, probes may be displaced by more than one base to cover the longer target with the same number of probes. By using long probes, the target may be interrogated directly without amplification or isolation from the rest of DNA in the sample. Also, several targets may be analyzed (screened for) in one sample simultaneously. If the obtained results indicate occurrence of a mutation (or a pathogen), additional pools of probes may be used to detect type of the mutation or subtype of pathogen. This is a desirable feature of the process which may be very cost effective in preventive diagnosis where only a small fraction of patients is expected to have an infection or mutation.

In the processes described in the examples, various detection methods may be used, for example, radiolabels, fluorescent labels, enzymes or antibodies (chemiluminescence), large molecules or particles detectable by light scattering or interferometric procedures.

EXAMPLE 13

Sequencing a Target Using Octamers and Nonamers

Data resulting from the hybridization of octamer and nonamer oligonucleotides shows that sequencing by hybridization provides an extremely high degree of accuracy. In this experiment, a known sequence was used to predict a series of contiguous overlapping component octamer and nonamer oligonucleotides.

In addition to the perfectly matching oligonucleotides, mismatch oligonucleotides, mismatch oligonucleotides wherein internal or end mismatches occur in the duplex formed by the oligonucleotide and the target were examined. In these analyses, the lowest practical temperature was used to maximize hybridization formation. Washes were accomplished at the same or lower temperatures to ensure maximal discrimination by utilizing the greater dissociation rate of mismatch versus matched oligonucleotide/target hybridization. These conditions are shown to be applicable to all sequences although the absolute hybridization yield is shown to be sequence dependent.

The least destabilizing mismatch that can be postulated is a simple end mismatch, so that the test of sequencing by hybridization is the ability to discriminate perfectly matched oligonucleotide/target duplexes from end-mismatched oligonucleotide/target duplexes.

The discriminative values for 102 of 105 hybridizing oligonucleotides in a dot blot format were greater than 2 allowing a highly accurate generation of the sequence. This system also allowed an analysis of the effect of sequence on hybridization formation and hybridization instability.

One hundred base pairs of a known portion of a human-interferon genes prepared by PCR, i.e. a 100 bp target sequence, was generated with data resulting from the hybridization of 105 oligonucleotides probes of known sequence to the target nucleic acid. The oligonucleotide probes used included 72 octamer and 21 nonamer oligonucleotides whose sequence was perfectly complementary to the target. The set of 93 probes provided consecutive overlapping frames of the target sequence e displaced by one or two bases.

To evaluate the effect of mismatches, hybridization was examined for 12 additional probes that contained at least one end mismatch when hybridized to the 100 bp test target sequence. Also tested was the hybridization of twelve probes with target end-mismatched to four other control nucleic acid sequences chosen so that the 12 oligonucleotides formed perfectly matched duplex hybrids with the four control DNAs. Thus, the hybridization of internal mismatched, end-mismatched and perfectly matched duplex pairs of oligonucleotide and target were evaluated for each oligonucleotide used in the experiment. The effect of absolute DNA target concentration on the hybridization with the test octamer and nonamer oligonucleotides was determined by defining target DNA concentration by detecting hybridization of a different oligonucleotide probe to a single occurrence non-target site within the co-amplified plasmid DNA.

The results of this experiment showed that all oligonucleotides containing perfect matching complementary sequence to the target or control DNA hybridized more strongly than those oligonucleotides having mismatches. To come to this conclusion, we examined $H_p$ and D values for each probe. $H_p$ defines the amount of hybrid duplex formed between a test target and an oligonucleotide probe. By assigning values of between 0 and 10 to the hybridization obtained for the 105 probes, it was apparent that 68.5% of the 105 probes had an $H_p$ greater than 2.

Discrimination (D) values were obtained where D was defined as the ratio of signal intensities between 1) the dot containing a perfect matched duplex formed between test oligonucleotide and target or control nucleic acid and 2) the dot containing a mismatch duplex formed between the same oligonucleotide and a different site within the target or control nucleic acid. Variations in the value of D result from either 1) perturbations in the hybridization efficiency which allows visualization of signal over background, or 2) the type of mismatch found between the test oligonucleotide and the target. The D values obtained in this experiment were between 2 and 40 for 102 of the 105 oligonucleotide probes examined. Calculations of D for the group of 102 oligonucleotides as a whole showed the average D was 10.6.

There were 20 cases where oligonucleotide/target duplexes exhibited an end-mismatch. In five of these, D was greater than 10. The large D value in these cases is most likely due to hybridization destabilization caused by other than the most stable (G/T and G/A) end mismatches. The other possibility is there was an error in the sequence of either the oligonucleotides or the target.

Error in the target for probes with low $H_p$ was excluded as a possibility because such an error would have affected the hybridization of each of the other eight overlapping oligonucleotides. There was no apparent instability due to sequence mismatch for the other overlapping oligonucleotides, indicating the target sequence was correct. Error in the oligonucleotide sequence was excluded as a possibility after the hybridization of seven newly synthesized oligonucleotides was reexamined. Only 1 of the seven oligonucleotides resulted in a better D value. Low hybrid formation values may result from hybrid instability or from an inability to form hybrid duplex. An inability to form hybrid duplexes would result from either 1) self complementarity of the chosen probe or 2) target/target self hybridization. Oligonucleotide/oligonucleotide duplex formation may be favored over oligonucleotide/target hybrid duplex formation if the probe was self-complementary. Similarly, target/target association may be favored if the target was self-complementary or may form internal palindromes. In evaluating these possibilities, it was apparent from probe analysis that the questionable probes did not form hybrids with themselves. Moreover, in examining the contribution of target/target hybridization, it was determined that one of the questionable oligonucleotide probes hybridized inefficiently with two different DNAs containing the same target. The low probability that two different DNAs have a self-complementary region for the same target sequence leads to the conclusion that target/target hybridization did not contribute to low hybridization formation. Thus, these results indicate that hybrid instability and not the inability to form hybrids was the cause of the low hybrid formation observed for specific oligonucleotides. The results also indicate that low hybrid formation is due to the specific sequences of certain oligonucleotides. Moreover, the results indicate that reliable results may be obtained to generate sequences if octamer and nonamer oligonucleotides are used.

These results show that using the methods described long sequences of any specific target nucleic acid may be generated by maximal and unique overlap of constituent oligonucleotides. Such sequencing methods are dependent on the content of the individual component oligomers regardless of their frequency and their position.

The sequence which is generated using the algorithm described below is of high fidelity. The algorithm tolerates false positive signals from the hybridization dots as is indicated from the fact the sequence generated from the 105 hybridization values, which included four less reliable values, was correct. This fidelity in sequencing by hybridization is due to the "all or none" kinetics of short oligonucleotide hybridization and the difference in duplex stability that exists between perfectly matched duplexes and mismatched duplexes. The ratio of duplex stability of matched and end-mismatched duplexes increases with decreasing duplex length. Moreover, binding energy decreases with decreasing duplex length resulting in a lower hybridization efficiency. However, the results provided show that octamer hybridization allows the balancing of the factors affecting duplex stability and discrimination to produce a highly accurate method of sequencing by hybridization. Results presented in other examples show that oligonucleotides that are 6, 7, or 8 nucleotides can be effectively used to generate reliable sequence on targets that are 0.5 kb (for hexamers) 2 kb (for septamers) and 6 kb (for octamers). The sequence of long fragments may be overlapped to generate a complete genome sequence.

EXAMPLE 14

Analyzing the Data Obtained

Image files are analyzed by an image analysis program, like DOTS program (Drmanac et al., 1993), and scaled and evaluated by statistical functions included, e.g., in SCORES program (Drmanac et al. 1994). From the distribution of the signals an optimal threshold is determined for transforming signal into +/- output. From the position of the label detected, F+P nucleotide sequences from the fragments would be determined by combining the known sequences of the immobilized and labeled probes corresponding to the labeled positions. The complete nucleic acid sequence or sequence subfragments of the original molecule, such as a human chromosome, would then be assembled from the overlapping F+P sequence determined by computational deduction.

One option is to transform hybridization signals e.g., scores, into +/- output during the sequence assembly process. In this case, assembly will start with a F+P sequence with a very high score, for example F+P sequence AAAAAATTTTT (SEQ ID NO: 1). Scores of all four possible overlapping probes AAAAATTTTTA (SEQ ID NO: 2), AAAAATTTTTT (SEQ ID NO: 3), AAAAATTTTTC (SEQ ID NO: 4) and AAAAATTTTTG (SEQ ID NO: 5) and three additional probes that are different at the beginning (TAAAAATTTTT (SEQ ID NO: 6); CAAAAATTTTT (SEQ ID NO: 7); GAAAAATTTTT (SEQ ID NO: 8), are compared and three outcomes defined: (i) only the starting probe and only one of the four overlapping proves have scores that are significantly positive relatively to the other six probes, in this case the AAAAAATTTTT (SEQ ID NO: 1) sequence will be extended for one nucleotide to the right; (ii) no one probe except the starting probe has a significantly positive score, assembly will stop, e.g., the AAAAAATTTTT (SEQ ID NO: 9) sequence is at the end of the DNA molecule that is sequenced; (iii) more than one significantly positive probe among the overlapped and/or other three probes is found; assembly is stopped because of the error or branching (Drmanac et al., 1989).

The processes of computational deduction would employ computer programs using existing algorithms (see, e.g., Pevzner, 1989; Drmanac et al., 1991; Labat and Drmanac, 1993; each incorporated herein by reference).

If, in addition to F+P, F(space 1)P, F(space 2)P, F(space 3)P or F(space 4)P are determined, algorithms will be used to match all data sets to correct potential errors or to solve the situation where there is a branching problem (see, e.g., Drmanac et al., 1989; Bains et al., 1988; each incorporated herein by reference).

EXAMPLE 15

Conducting Sequencing by Two Step Hybridization

Following the certain examples to describe the execution of the sequencing methodology contemplated by the inventor. First, the whole chip would be hybridized with mixture of DNA as complex as 100 million of bp (one human chromosome). Guidelines for conducting hybridization can be found in papers such as Drmanac et al. (1990); Khrapko et al. (1991); and Broude et al. (1994). These articles teach the ranges of hybridization temperatures, buffers and washing steps that are appropriate for use in the initial steps of Format 3 SBH.

The present inventor particularly contemplates that hybridization is to be carried out for up to several hours in high salt concentrations at a low temperature (−2° C. to 5° C.) because of a relatively low concentration of target DNA that can be provided. For this purpose, SSC buffer is used instead of sodium phosphate buffer (Drmanac et al, 1990), which precipitates at 10° C. Washing does not have to be extensive (a few minutes) because of the second step, and can be completely eliminated when the hybridization cycling is used for the sequencing of highly complex DNA samples. The same buffer is used for hybridization and washing steps to be able to continue with the second hybridization step with labeled probes.

After proper washing using a simple robotic device on each array, e.g., a 8×8 mm array, one labeled, probe, e.g., a 6-mer, would be added. A 96-tip or 96-pin device would be used, performing this in 42 operations. Again, a range of discriminatory conditions could be employed, as previously described in the scientific literature.

The present inventor particularly contemplates the use of the following conditions. First, after adding labeled probes and incubating for several minutes only (because of the high concentration of added oligonucleotides) at a low temperature (0–5° C.), the temperature is increased to 3–10° C., depending on F+P length, and the washing buffer is added. At this time, the washing buffer used is one compatible with any ligation reaction (e.g., 100 mM salt concentration range). After adding ligase, the temperate is increased again to 15–37° C. to allow fast ligation (less than 30 min) and further discrimination of full match and mismatch hybrids.

The use of cationic detergents is also contemplated for use in Format 3 SBH, as described by Pontius & Berg (1991, incorporated herein by reference). These authors describe the use of two simple cationic detergents, dodecy- and cetyltrimethylammonium bromide (DTAB and CTAB) in DNA renaturation.

DTAB and CTAB are variants of the quaternary amine tetramethylammonium bromide (TMAB) in which one of the methyl groups is replaced by either a 12-carbon (DTAB) or a 16-carbon (CTAB) alkyl group. TMAB is the bromide salt of the tetramethylammonium ion, a reagent used in nucleic acid renaturation experiments to decrease the G-C content bias of the melting temperature. DTAB and CTAB are similar in structure to sodium dodecyl sulfate (SDS), with the replacement of the negatively charged sulfate of SDS by a positively charged quaternary amine. While SDS is commonly used in hybridization buffers to reduce non-specific binding and inhibit nucleases, it does not greatly affect the rate of renaturation.

When using a ligation process, the enzyme could be added with the labeled probes or after the proper washing step to reduce the background. Although not previously proposed for use in any SBH method, ligase technology is well established within the field of molecular biology. For example, Hood and colleagues described a ligase-mediated gene detection technique (Landegren et al., 1988), the methodology of which can be readily adapted for use in Format 3 SBH. Wu & Wallace also describe the use of bacteriophage T4 DNA ligase to join two adjacent, short synthetic oligonucleotides. Their oligo ligation reactions were carried out in 50 mM Tris HCl pH 7.6, 10 mM $MgCl_2$, 1 mM ATP, 1 mM DTT, and 5% PEG. Ligation reactions were heated to 100° C. for 5–10 min followed by cooling to 0° C. prior to the addition of T4 DNA ligase (1 unit; Bethesda Research Laboratory). Most ligation reactions were carried out at 30° C. and terminated by heating to 100° C. for 5 min.

Final washing appropriate for discriminating detection of hybridized adjacent, or ligated, oligonucleotides of length (F+P), is then performed. This washing step is done in water for several minutes at 40–60° C. to wash out all the non-ligated labeled probes, and all other compounds, to maximally reduce background. Because of the covalently bound labeled oligonucleotides, detection is simplified (it does not have time and low temperature constrains).

Depending on the label used, imaging of the chips is done with different apparati. For radioactive labels, phosphor storage screen technology and PhosphorImager as a scanner may be used (Molecular Dynamics, Sunnyvale, Calif.). Chips are put in a cassette and covered by a phosphorous screen. After 1–4 hours of exposure, the screen is scanned and the image file stored at a computer hard disc. For the detection of fluorescent labels, CCD cameras and epifluorescent or confocal microscopy are used. For the chips generated directly on the pixels of a CCD camera, detection can be performed as described by Eggers et al. (1994, incorporated herein by reference).

Charge-coupled device (CCD) detectors serve as active solid supports that quantitatively detect and image the distribution of labeled target molecules in probe-based assays. These devices use the inherent characteristics of microelectronics that accommodate highly parallel assays, ultrasensitive detection, high throughput, integrated data acquisition and computation. Eggers et al. (1994) describe CCDs for use with probe-based assays, such as Format 3 SBH of the present invention, that allow quantitative assessment within seconds due to the high sensitivity and direct coupling employed.

The integrated CCD detection approach enables the detection of molecular binding events on chips. The detector rapidly generates a two-dimensional pattern that uniquely characterizes the sample. In the specific operation of the CCD-based molecular detector, distinct biological probes are immobilized directly on the pixels of a CCD or can be attached to a disposable cover slip placed on the CCD surface. The sample molecules can be labeled with radioisotope, chemiluminescent or fluorescent tags.

Upon exposure of the sample to the CCD-based probe array, photons or radioisotope decay products are emitted at the pixel locations where the sample has bound, in the case of Format 3, to two complementary probes. In turn, electron-hole pairs are generated in the silicon when the charged particles, or radiation from the labeled sample, are incident on the CCD gates. Electrons are then collected beneath adjacent CCD gates and sequentially read out on a display module. The number of photoelectrons generated at each pixel is directly proportional to the number of molecular binding events in such proximity. Consequently, molecular binding can be quantitatively determined (Eggers et al., 1994).

By placing the imaging array in proximity to the sample, the collection efficiency is improved by a factor of at least 10 over lens-based techniques such as those found in conventional CCD cameras. That is, the sample (emitter) is in near contact with the detector (imaging array), and this eliminates conventional imaging optics such as lenses and mirrors.

When radioisotopes are attached as reporter groups to the target molecules, energetic particles are detected. Several reporter groups that emit particles of varying energies have been successfully utilized with the micro-fabricated detectors, including $^{32}P$, $^{33}P$, $^{35}S$, $^{14}C$ and $^{125}L$. The higher energy particles, such as from $^{32}P$, provide the highest molecular detection sensitivity, whereas the lower energy particles, such as from $^{35}S$, provide better resolution. Hence the choice of the radioisotope reporter can be tailored as required. Once the particular radioisotope label is selected, the detection performance can be predicted by calculating the signal-to-noise ration (SNR), as described by Eggers et al. (1994).

An alternative luminescent detection procedure involves the use of fluorescent or chemiluminescent reporter groups attached to the target molecules. The fluorescent labels can be attached covalently or through interaction. Fluorescent dyes, such as ethidium bromide, with intense absorption bands in the near UV (300–350 nm) range and principal emission bands in the visible (500–650 nm) range, are most suited for the CCD devices employed since the quantum efficiency is several orders of magnitude lower at the excitation wavelength then at the fluorescent signal wavelength.

From the perspective of detecting luminescence, the polysilicon CCD gates have the built-in capacity to filter away the contribution of incident light in the UV range, yet are very sensitive to the visible luminescence generated by the fluorescent reporter groups. Such inherently large discrimination against UV excitation enables large SNRs (greater than 100) to be achieved by the CCDs as formulated in the incorporated paper by Eggers et al. (1994).

For probe immobilization on the detector, hybridization matrices may be produced on inexpensive $SiO_2$ wafers, which are subsequently placed on the surface of the CCD following hybridization and drying. This format is economically efficient since the hybridization of the DNA is conducted on inexpensive disposable $SiO_2$ wafers, thus allowing reuse of the more expensive CCD detector. Alternatively, the probes can be immobilized directly on the CCD to create a dedicated probe matrix.

To immobilize probes upon the $SiO_2$ coating, a uniform epoxide layer is linked to the film surface, employing an epoxy-silane reagent and standard $SiO_2$ modification chemistry. Amine-modified oligonucleotide probes are then linked to the $SiO_2$ surface by means of secondary amine formation with the epoxide ring. The resulting linkage provides 17 rotatable bonds of separation between the 3 base of the oligonucleotide and the $SiO_2$ surface. To ensure complete amine deprotonation and to minimize secondary structure formation during coupling, the reaction is performed in 0.1 M KOH and incubated at 37° C. for 6 hours.

In Format 3 SBH in general, signals are scored per each of billion points. It would not be necessary to hybridize all arrays, e.g., 4000 5×5 mm, at a time and the successive use of smaller number of arrays is possible.

Cycling hybridizations are one possible method for increasing the hybridization signal. In one cycle, most of the fixed probes will hybridize with DNA fragments with tail sequences non-complementary for labeled probes. By increasing the temperature, those hybrids will be melted. In the next cycle, some of them (~0.1%) will hybridize with an appropriate DNA fragment and additional labeled probes will be ligated. In this case, there occurs a discriminative melting of DNA hybrids with mismatches for both probe sets simultaneously.

In the cycle hybridization, all components are added before the cycling starts, at the 37° C. for T4, or a higher temperature for a thermostable ligase. Then the temperature is decreased to 15–37° C. and the chip is incubated for up to 10 minutes, and then the temperature is increased to 37° C. or higher for a few minutes and then again reduced. Cycles can be repeated up to 10 times. In one variant, an optimal higher temperature (10–50° C.) can be used without cycling and longer ligation reaction can be performed (1–3 hours).

The procedure described herein allows complex chip manufacturing using standard synthesis and precise spotting of oligonucleotides because a relatively small number of oligonucleotides are necessary. For example, if all 7-mer oligos are synthesized (16384 probes), lists of 256 million 14-mers can be determined.

One important variant of the invented method is to use more than one differently labeled probe per base array. This can be executed with two purposes in mind; multiplexing to reduce number of separately hybridized arrays; or to determine a list of even longer oligosequences such as 3×6 or 3×7. In this case, if two labels are used, the specificity of the 3 consecutive oligonucleotides can be almost absolute because positive sites must have enough signals of both labels.

A further and additional variant is to use chips containing BxNy probes with y being from 1 to 4. Those chips allow sequence reading in different frames. This can also be achieved by using appropriate sets of labeled probes or both F and P probes could have some unspecified end positions (i.e., some element of terminal degeneracy). Universal bases may also be employed as part of a linker to join the probes of defmed sequence to the solid support. This makes the probe more available to hybridization and makes the construct more stable. If a probe has 5 bases, one may, e.g., use 3 universal bases as a linker.

EXAMPLE 16
Determining Sequence from Hybridization Data

Sequence assembly may be interrupted where ever a given overlapping (N-1) mer is duplicated two or more times. Then either of the two N-mers differing in the last nucleotide may be used in extending the sequence. This branching point limits unambiguous assembly of sequence.

Reassembling the sequence of known oligonucleotides that hybridize to the target nucleic acid to generate the complete sequence of the target nucleic acid may not be accomplished in some cases. This is because some information may be lost if the target nucleic acid is not in fragments of appropriate size in relation to the size of oligonucleotide that is used for hybridizing. The quantity of information lost is proportional to the length of a target being sequenced. However, if sufficiently short targets are used, their sequence msy be unambiguously determined.

The probable frequency of duplicated sequences that would interfere with sequence assembly which is distributed along a certain length of DNA may be calculated. This derivation requires the introduction of the definition of a parameter having to do with sequence organization: the sequence subfragment (SF). A sequence subfragment results if any part of the sequence of a target nucleic acid starts and ends with an (N-1)mer that is repeated two or more times within the target sequence. Thus, subfragments are sequences generated between two points of branching in the process of assembly of the sequences in the method of the invention. The sum of all subfragrnents is longer than the actual target nucleic acid because of overlapping short ends.

Generally, subfragments may not be assembled in a linear order without additional information since they have shared (N-1)mers at their ends and starts. Different numbers of subfragments are obtained for each nucleic acid target depending on the number of its repeated (N-1) mers. The number depends on the value of N-1 and the length of the target.

Probability calculations can estimate the interrelationship of the two factors. If the ordering of positive N-mers is accomplished by using overlapping sequences of length N-1 or at an average distance of $A_o$, the N-1 of a fragment Lf bases long is given by equation one:

$$N_{sf} = 1 + A_o \times K \times P\ (K; L_f)$$

Where K greater than or=2, and $P\ (K, L_f)$ represents the probability of an N-mer occurring K-times on a fragment $L_f$ base long. Also, a computer program that is able to form subfragments from the content of N-mers for any given sequence is described below in Example 18.

The number of subfragments increases with the increase of lengths of fragments for a given length of probe. Obtained subfragments may not be uniquely ordered among themselves. Although not complete, this information is very useful for comparative sequence analysis and the recognition of functional sequence characteristics. This type of information may be called partial sequence. Another way of obtaining partial sequence is the use of only a subset of oligonucleotide probes of a given length.

There may be relatively good agreement between predicted sequence according to theory and a computer simulation for a random DNA sequence. For instance, for N-1=7, [using an 8-mer or groups of sixteen 10-mers of type 5' (A,T,C,G) $B_8$ (A,T,C,G) 3'] a target nucleic acid of 200 bases will have an average of three subfragments. However, because of the dispersion around the mean, a library of target nucleic acid should have inserts of 500 bp so that less than 1 in 2000 targets have more than three subfragments. Thus, in an ideal case of sequence determination of a long nucleic acid of random sequence, a representative library with sufficiently short inserts of target nucleic acid may be used. For such inserts, it is possible to reconstruct the individual target by the method of the invention. The entire sequence of a large nucleic acid is then obtained by overlapping of the defined individual insert sequences.

To reduce the need for very short fragments, e.g. 50 bases for 8-mer probes. The information contained in the overlapped fragments present in every random DNA fragmentation process like cloning, or random PCR is used. It is also possible to use pools of short physical nucleic acid fragments. Using 8-mers or 11-mers like 5' (A, T, C, G) $N_8$ (A, T, C ,G )3' for sequencing 1 megabase, instead of needing 20,000 50 bp fragments only 2,100 samples are sufficient. This number consists of 700 random 7 kb clones (basic library), 1250 pools of 20 clones of 500 bp (subfragments ordering library) and 150 clones from jumping (or similar) library. The developed algorithm (see Example 18) regenerates sequence using hybridization data of these described samples.

EXAMPLE 17
Algorithm

This example describes an algorithm for generation of a long sequence written in a four letter alphabet from constituent k-tuple words in a minimal number of separate, randomly defined fragments of a starting nucleic acid sequence where K is the length of an oligonucleotide probe. The algorithm is primarily intended for use in the sequencing by hybridization (SBH) process. The algorithm is based on subfragments (SF), informative fragments (IF) and the possibility of using pools of physical nucleic sequences for defining informative fragments.

As described, subfragments may be caused by branch points in the assembly process resulting from the repetition of a K–1 oligomer sequence in a target nucleic acid. Subfragments are sequence fragments found between any two repetitive words of the length K–1 that occur in a sequence. Multiple occurrences of K–1 words are the cause of interruption of ordering the overlap of K-words in the process of sequence generation. Interruption leads to a sequence remaining in the form of subfragments. Thus, the unambiguous segments between branching points whose order is not uniquely determined are called sequence subfragments.

Informative fragments are defined as fragments of a sequence that are determined by the nearest ends of overlapped physical sequence fragments.

A certain number of physical fragments may be pooled without losing the possibility of defining informative fragments. The total length of randomly pooled fragments depends on the length of k-tuples that are used in the sequencing process.

The algorithm consists of two main units. The first part is used for generation of subfragments from the set of k-tuples contained in a sequence. Subfragments may be generated within the coding region of physical nucleic acid sequence of certain sizes, or within the informative fragments defined within long nucleic acid sequences. Both types of fragments are members of the basic library. This algorithm does not describe the determination of the content of the k-tuples of the informative fragments of the basic library, i.e. the step of preparation of informative fragments to be used in the sequence generation process.

The second part of the algorithm determines the linear order of obtained subfragments with the purpose of regenerating the complete sequence of the nucleic acid fragments of the basic library. For this purpose a second, ordering library is used, made of randomly pooled fragments of the starting sequence. The algorithm does not include the step of combining sequences of basic fragments to regenerate an entire, megabase plus sequence. This may be accomplished using the link-up of fragments of the basic library which is a prerequisite for informative fragment generation. Alternatively, it may be accomplished after generation of sequences of fragments of the basic library by this algorithm, using search for their overlap, based on the presence of common end-sequences.

The algorithm requires neither knowledge of the number of appearances of a given k-tuple in a nucleic acid sequence of the basic and ordering libraries, nor does it require the information of which k-tuple words are present on the ends of a fragment. The algorithm operates with the mixed content of k-tuples of various length. The concept of the algorithm enables operations with the k-tuple sets that contain false positive and false negative k- tuples. Only in specific cases does the content of the false k-tuples primarily influence the completeness and correctness of the generated sequence. The algorithm may be used for optimization of parameters in simulation experiments, as well as for sequence generation in the actual SBH experiments e.g. generation of the genomic DNA sequence. In optimization of parameters, the choice of the oligonucleotide probes (k-tuples) for practical and convenient fragments and/or the choice of the optimal lengths and the number of fragments for the defined probes are especially important.

This part of the algorithm has a central role in the process of the generation of the sequence from the content of k-tuples. It is based on the unique ordering of k-tuples by means of maximal overlap. The main obstacles in sequence generation are specific repeated sequences and false positive and/or negative k-tuples. The aim of this part of the algorithm is to obtain the minimal number of the longest possible subfragments, with correct sequence. This part of the algorithm consists of one basic, and several control steps. A two-stage process is necessary since certain information can be used only after generation of all primary subfragments.

The main problem of sequence generation is obtaining a repeated sequence from word contents that by definition do not carry information on the number of occurrences of the particular k-tuples. The concept of the entire algorithm depends on the basis on which this problem is solved. In principle, there are two opposite approaches: 1) repeated sequences may be obtained at the beginning, in the process of generation of pSFs, or 2) repeated sequences can be obtained later, in the process of the final ordering of the subfragments. In the first case, pSFs contain an excess of sequences and in the second case, they contain a deficit of sequences. The first approach requires elimination of the excess sequences generated, and the second requires permitting multiple use of some of the subfragments in the process of the final assembling of the sequence.

The difference in the two approaches in the degree of strictness of the rule of unique overlap of k-tuples. The less severe rule is: k-tuple X is unambiguously maximally overlapped with k-tuple Y if and only if, the rightmost k–1 end of k-tuple X is present only on the leftmost end of k-tuple Y. This rule allows the generation of repetitive sequences and the formation of surplus sequences.

A stricter rule which is used in the second approach has an addition caveat: k-tuple X is unambiguously maximally overlapped with k-tuple Y if and only if, the rightmost K–1 end of k-tuple X is present only on the leftmost end of k-tuple Y and if the leftmost K–1 end of k-tuple Y is not present on the rightmost end of any other k-tuple. The algorithm based on the stricter rule is simpler, and is described herein.

The process of elongation of a given subfragment is stopped when the right k–1 end of the last k-tuple included is not present on the left end of any k-tuple or is present on two or more k-tuples. If it is present on only one k-tuple the second part of the rule is tested. If in addition there is a k-tuple which differs from the previously included one, the assembly of the given subfragment is terminated only on the first leftmost position. If this additional k-tuple does not exist, the conditions are met for unique k–1 overlap and a given subfragment is extended to the right by one element.

Beside the basic rule, a supplementary one is used to allow the usage of k-tuples of different lengths. The maximal overlap is the length of k–1 of the shorter k-tuple of the overlapping pair. Generation of the pSFs is performed starting from the first k-tuple from the file in which k-tuples are displayed randomly and independently from their order in a nucleic acid sequence. Thus, the first k-tuple in the file is not necessarily on the beginning of the sequence, nor on the start of the particular subfragment. The process of subfragment generation is performed by ordering the k-tuples by means of unique overlap, which is defined by the described rule. Each used k-tuple is erased from the file. At the point when there are no further k-tuples unambiguously overlapping with the last one included, the building of subfragment is terminated and the buildup of another pSF is started. Since generation of a majority of subfragments does not begin from their actual starts, the formed pSF are added to the k-tuple file and are considered as a longer k-tuple.

Another possibility is to form subfragments going in both directions from the starting k-tuple. The process ends when further overlap, i.e. the extension of any of the subfragments, is not possible.

The pSFs can be divided in three groups: 1) Subfragments of the maximal length and correct sequence in cases of exact k-tuple set; 2) short subfragments, formed due to the used of the maximal and unambiguous overlap rule on the incomplete set, and/or the set with some false positive k-tuples; and 3) pSFs of an incorrect sequence. The incompleteness of the set in 2) is caused by false negative results of a hybridization experiment, as well as by using an incorrect set of k-tuples. These are formed due to the false positive and false negative k-tuples and can be: a) misconnected subfragments; b) subfragments with the wrong end; and c) false positive k-tuples which appears as false minimal subfragments.

Considering false positive k-tuples, there is the possibility for the presence of a k-tuple containing more than one wrong base or containing one wrong base somewhere in the middle, as well as the possibility for a k-tuple with a wrong base on the end. Generation of short, erroneous or misconnected subfragments is caused by the latter k-tuples. The k-tuples of the former two kinds represent wrong pSFs with length equal to k-tuple length.

In the case of one false negative k-tuple, pSFs are generated because of the impossibility of maximal overlapping. In the case of the presence of one false positive k-tuple with the wrong base on its leftmost or rightmost end, pSFs are generated because of the impossibility of unambiguous overlapping. When both false positive and false negative k-tuples with a common k−1 sequence are present in the file, pSFs are generated, and one of these pSFs contains the wrong k-tuple at the relevant end.

The process of correcting subfragments with errors in sequence and the linking of unambiguously connected pSF is performed after subfragment generation and in the process of subfragment ordering. The first step which consists of cutting the misconnected pSFs and obtaining the final subfragments by unambiguous connection of pSFs is described below.

There are two approaches for the formation of misconnected subfragments. In the first a mistake occurs when an erroneous k-tuple appears on the points of assembly of the repeated sequences of lengths k−1. In the second, the repeated sequences are shorter than k−1. These situations can occur in two variants each. In the first variant, one of the repeated sequences represents the end of a fragment. In the second variant, the repeated sequence occurs at any position within the fragment. For the first possibility, the absence of some k-tuples from the file (false negatives) is required to generate a misconnection. The second possibility requires the presence of both false negative and false positive k-tuples in the file. Considering the repetitions of k−1 sequence, the lack of only one k-tuple is sufficient when either end is repeated internally. The lack of two is needed for strictly internal repetition. The reason is that the end of a sequence can be considered informatically as an endless linear array of false negative k-tuples. From the "smaller than k−1 case", only the repeated sequence of the length of k−2, which requires two or three specific erroneous k-tuples, will be considered. It is very likely that these will be the only cases which will be detected in a real experiment, the others being much less frequent.

Recognition of the misconnected subfragments is more strictly defined when a repeated sequence does not appear at the end of the fragment. In this situation, one can detect further two subfragments, one of which contains on its leftmost, and the other on its rightmost end k−2 sequences which are also present in the misconnected subfragment. When the repeated sequence is on the end of the fragment, there is only one subfragment which contains k−2 sequence causing the mistake in subfragment formation on its leftmost or rightmost end.

The removal of misconnected subframents by their cutting is performed according to the common rule: If the leftmost or rightmost sequence of the length of k−2 of any subfragments is present in any other subfragment, the subfragment is to be cut into two subfragments, each of them containing k−2 sequence. This rule does not cover rarer situations of a repeated end when there are more than one false negative k-tuple on the point of repeated k−1 sequence. Misconnected subfragments of this kind can be recognized by using the information from the overlapped fragments, or informative fragments of both the basic and ordering libraries. In addition, the misconnected subfragment will remain when two or more false negative k-tuples occur on both positions which contain the identical k−1 sequence. This is a very rare situation since it requires at least 4 specific false k-tuples. An additional rule can be introduced to cut these subfragments on sequences of length k if the given sequence can be obtained by combination of sequences shorter than k−2 from the end of one subfragment and the start of another.

By strict application of the described rule, some completeness is lost to ensure the accuracy of the output. Some of the subfragments will be cut although they are not misconnected since they fit into the pattern of a misconnected subfragment. There are several situations of this kind. For example, a fragment, beside at least two identical k−1 sequences, contains any k−2 sequence from k−1 or a fragment contains k−2 sequence repeated at least twice and at least one false negative k-tuple containing given k−2 sequence in the middle, etc.

The aim of this part of the algorithm is to reduce the number of pSFs to a minimal number of longer subfragments with correct sequence. The generation of unique longer subfragments or a complete sequence is possible in two situations. The first situation concerns the specific order of repeated k−1 words. There are cases in which some or all maximally extended pSFs (the first group of pSFs) can be uniquely ordered. For example, in fragment S-R1-a-R2-b-R1-c-R2-E where S and E are the start and end of a fragment, a, b, and c are different sequences specific to respective subfragments and R1 and R2 are two k−1 sequences that are tandemly repeated, five subfragments are generated (S-R1, R1-a-R2, R2-b-R1, R1-c-R2, and R-E). They may be ordered in two ways; the original sequence above or S-R1-c-R-b-R1-a-R-E. In contrast, in a fragment with the same number and types of repeated sequences but ordered differently, i.e. S-R1-a-R1-b-R-c-R-E, there is no other sequence which includes all subfragments. Examples of this type can be recognized only after the process of generation of pSFs. They represent the necessity for two steps in the process of pSF generation. The second situation of generation of false short subfragments on positions of nonrepeated k−1 sequences when the files contain false negative and/or positive k-tuples is more important.

The solution for both pSF groups consists of two parts. First, the false positive k-tuples appearing as the nonexisting minimal subfragments are eliminated. All k-tuple subfragments of length k which do not have an overlap on either end, of the length of longer than k-a on one end and longer than k-b on the other end, are eliminated to enable formation of the maximal number of connections. In our experiments, the values for a and b of 2 and 3, respectively, appeared to be adequate to eliminate a sufficient number of false positive k-tuples.

The merging of subfragments that can be uniquely connected is accomplished in the second step. The rule for connection is: two subfragments may be unambiguously connected if, and only if, the overlapping sequence at the relevant end or start of two subfragments is not present at the start and/or end of any other subfragment.

The exception is if one subfragment from the considered pair has the identical beginning and end. In that case connection is permitted, even if there is another subfragment with the same end present in the file. The main problem here is the precise definition of overlapping sequence. The connection is not permitted if the overlapping sequence unique for only one pair of subfragments is shorter than k−2, of it is k−2 or longer but an additional subfragment exists with the overlapping sequence of any length longer than k−4. Also, both the canonical ends of pSFs and the ends after omitting one (or few) last bases are considered as the overlapping sequences.

After this step some false positive k-tuples (as minimal subfragments) and some subfragments with a wrong end may survive. In addition, in very rare occasions where a certain number of some specific false k-tuples are simultaneously present, an erroneous connection may take place. These cases will be detected and solved in the subfragment ordering process, and in the additional control steps along with the handling of uncut "misconnected" subfragments.

The short subfragments that are obtained are of two kinds. In the common case, these subfragments may be unambiguously connected among themselves because of the distribution of repeated k−1 sequences. This may be done after the process of generation of pSFs and is a good example of the necessity for two steps in the process of pSF generation. In the case of using the file containing false positive and/or false negative k-tuples, short pSFs are obtained on the sites of nonrepeated k−1 sequences. Considering false positive k-tuples, a k-tuple may contain more than one wrong base (or containing one wrong base somewhere in the middle), as well as k-tuple on the end. Generation of short and erroneous (or misconnected) subfragments is caused by the latter k-tuples. The k-tuples of the former kind represent wrong pSFs with length equal to k-tuple length.

The aim of merging pSF part of the algorithm is the reduction of the number of pSFs to the minimal number of longer subfragments with the correct sequence. All k-tuple subfragments that do not have an overlap on either end, of the length of longer than k−a on one, and longer than k−b on the other end, are eliminated to enable the maximal number of connections. In this way, the majority of false positive k-tuples are discarded. The rule for connection is: two subfragments can be unambiguously connected if, and only if the overlapping sequence of the relevant end or start of two subfragments is not present on the start and/or end of any other subfragment. The exception is a subfragment with the identical beginning and end. In that case connection is permitted, provided that there is another subfragment with the same end present in the file. The main problem here is of precise definition of overlapping sequence. The presence of at least two specific false negative k-tuples on the points of repetition of k−1 or k−2 sequences, as well as combining of the false positive and false negative k-tuples may destroy or "mask" some overlapping sequences and can produce an unambiguous, but wrong connection of pSFs. To prevent this, completeness must be sacrificed on account of exactness: the connection is not permitted on the end-sequences shorter than k−2, and in the presence of an extra overlapping sequence longer than k4. The overlapping sequences are defined from the end of the pSFs, or omitting one, or few last bases.

In the very rare situations, with the presence of a certain number of some specific false positive and false negative k-tuples, some subfragments with the wrong end can survive, some false positive k-tuples (as minimal subfragments) can remain, or the erroneous connection can take place. These cases are detected and solved in the subfragments ordering process, and in the additional control steps along with the handling of uncut, misconnected subfragments.

The process of ordering of subfragments is similar to the process of their generation. If one considers subfragments as longer k-tuples, ordering is performed by their unambiguous connection via overlapping ends. The informational basis for unambiguous connection is the division of subfragments generated in fragments of the basic library into groups representing segments of those fragments. The method is analogous to the biochemical solution of this problem based on hybridization with longer oligonucleotides with relevant connecting sequence. The connecting sequences are generated as subfragments using the k-tuple sets of the appropriate segments of basic library fragments. Relevant segments are defined by the fragments of the ordering library that overlap with the respective fragments of the basic library. The shortest segments are informative fragments of the ordering library. The longer ones are several neighboring informative fragments or total overlapping portions of fragments corresponding of the ordering and basic libraries. In order to decrease the number of separate samples, fragments of the ordering library are randomly pooled, and the unique k-tuple content is determined.

By using the large number of fragments in the ordering library very short segments are generated, thus reducing the chance of the multiple appearance of the k−1 sequences which are the reasons for generation of the subfragments. Furthermore, longer segments, consisting of the various regions of the given fragment of the basic library, do not contain some of the repeated k−1 sequences. In every segment a connecting sequence (a connecting subfragment) is generated for a certain pair of the subfragments from the given fragment. The process of ordering consists of three steps: (1) generation of the k-tuple contents of each segment; (2) generation of subfragments in each segment; and (3) connection of the subfragments of the segments. Primary segments are defined as significant intersections and differences of k-tuple contents of a given fragment of the basic library with the k-tuple contents of the pools of the ordering library. Secondary (shorter) segments are defined as intersections and differences of the k-tuple contents of the primary segments.

There is a problem of accumulating both false positive and negative k-tuples in both the differences and intersections. The false negative k-tuples from starting sequences accumulate in the intersections (overlapping parts), as well as false positive k-tuples occurring randomly in both sequences, but not in the relevant overlapping region. On the other hand, the majority of false positives from either of the starting sequences is not taken up into intersections. This is an example of the reduction of experimental errors from individual fragments by using information from fragments overlapping with them. The false k-tuples accumulate in the differences for another reason. The set of false negatives from the original sequences are enlarged for false positives from intersections and the set of false positives for those k-tuples which are not included in the intersection by error, i.e. are false negative in the intersection. If the starting sequences contain 10% false negative data, the primary and secondary intersections will contain 19% and 28% false negative k-tuples, respectively. On the other hand, a mathematical expectation of 77 false positives may be predicted if the basic fragment and the pools have lengths of 500 bp and 10,000 bp, respectively. However, there is a possibility of recovering most of the "lost" k-tuples and of eliminating most of the false positive k-tuples.

First, one has to determine a basic content of the k-tuples for a given segment as the intersection of a given pair of the k-tuple contents. This is followed by including all k-tuples of the starting k-tuple contents in the intersection, which contain at one end k−1 and at the other end k−+sequences which occur at the ends of two k-tuples of the basic set. This is done before generation of the differences thus preventing the accumulation of false positives in that process. Following that, the same type of enlargement of k-tuple set is applied to differences with the distinction that the borrowing is from the intersections. All borrowed k-tuples are eliminated from the intersection files as false positives.

The intersection, i.e. a set of common k-tuples, is defined for each pair (a basic fragment)×(a pool of ordering library). If the number of k-tuples in the set is significant it is enlarged with the false negatives according to the described rule. The primary difference set is obtained by subtracting from a given basic fragment the obtained intersection set. The false negative k-tuples are appended to the difference set by borrowing from the intersection set according to the described rule and, at the same time, removed from the intersection set as false positive k-tuples. When the basic fragment is longer than the pooled fragments, this difference can represent the two separate segments which somewhat reduces its utility in further steps. The primary segments are all generated intersections and differences of pairs (a basic fragment)×(a pool of ordering library) containing the significant number of k-tuples. K-tuple sets of secondary segments are obtained by comparison of k-tuple sets of all possible pairs of primary segments. The two differences are defined from each pair which produces the intersection with the significant number of k-tuples. The majority of available information from overlapped fragments is recovered in this step so that there is little to be gained from the third round of forming intersections and differences.

(2) Generation of the subfragments of the segments is performed identically as described for the fragments of the basic library.

(3) The method of connection of subfragments consists of sequentially determining the correctly linked pairs of subfragments among the subfragments from a given basic library fragment which have some overlapped ends. In the case of 4 relevant subfragments, two of which contain the same beginning and two having the same end, there are 4 different pairs of subfragments that can be connected. In general 2 are correct and 2 are wrong. To find correct ones, the presence of the connecting sequences of each pair is tested in the subfragments generated from all primary and secondary segments for a given basic fragment. The length and the position of the connecting sequence are chosen to avoid interference with sequences which occur by chance. They are k+2 or longer, and include at least one element 2 beside overlapping sequence in both subfragments of a given pair. The connection is permitted only if the two connecting sequences are found and the remaining two do not exist. The two linked subfragments replace former subfragments in the file and the process is cyclically repeated.

Repeated sequences are generated in this step. This means that some subfragments are included in linked subfragments more than once. They will be recognized by finding the relevant connecting sequence which engages one subfragment in connection with two different subfragments.

The recognition of misconnected subfragments generated in the processes of building pSFs and merging pSFs into longer subfragments is based on testing whether the sequences of subfragments from a given basic fragment exist in the sequences of subfragments generated in the segments for the fragment. The sequences from an incorrectly connected position will not be found indicating the misconnected subfragments.

Beside the described three steps in ordering of subfragments some additional control steps or steps applicable to specific sequences will be necessary for the generation of more complete sequence without mistakes.

The determination of which subfragment belongs to which segment is performed b comparison of contents of k-tuples in segments and subfragments. Because of the errors in the k-tuple contents (due to the primary error in pools and statistical errors due to the frequency of occurrences of k-tuples) the exact partitioning of subfragments is impossible. Thus, instead of "all or none" partition, the chance of coming from the given segment (P(sf,s)) is determined for each subfragment. This possibility is the function of the lengths of k-tuples, the lengths of subfragments, the lengths of fragments of ordering library, the size of the pool, and of the percentage of false k-tuples in the file:

$$P(sf,s)=(Ck-F)/Lsf,$$

where Lsf is the length of subfragment, Ck is the number of common k-tuples for a given subfragment/segment pair, and F is the parameter that includes relations between lengths of k-tuples, fragments of basic library, the size of the pool, and the error percentage.

Subfragments attributed to a particular segment are treated as redundant short pSFs and are submitted to a process of unambiguous connection. The definition of unambiguous connection is slightly different in this case, since it is based on a probability that subfragments with overlapping end(s) belong to the segment considered. Besides, the accuracy of unambiguous connection is controlled by following the connection of these subfragments in other segments. After the connection in different segments, all of the obtained subfragments are merged together, shorter subfragments included within longer ones are eliminated, and the remaining ones are submitted to the ordinary connecting process. If the sequence is not regenerated completely, the process of partition and connection of subfragments is repeated with the same or less severe criterions of probability of belonging to the particular segment, followed by unambiguous connection.

Using severe criteria for defining unambiguous overlap, some information is not used. Instead of a complete sequence, several subfragments that define a number of possibilities for a given fragment are obtained. Using less severe criteria an accurate and complete sequence is generated. In a certain number of situations, e.g. an erroneous connection, it is possible to generate a complete, but an incorrect sequence, or to generate "monster" subfragments with no connection among them. Thus, for each fragment of the basic library one obtains: a) several possible solutions where one is correct and b) the most probable correct solution. Also, in a very small number of cases, due to the mistake in the subfragment generation process or due to the specific ratio of the probabilities of belonging, no unambiguous solution is generated or one, the most probable solution. These cases remain as incomplete sequences, or the unambiguous solution is obtained by comparing these data with other, overlapped fragments of basic library.

The described algorithm was tested on a randomly generated, 50 kb sequence, containing 40% GC to simulate the GC content of the human genome. In the middle part of this sequence were inserted various All, and some other repetitive sequences, of a total length of about 4 kb. To simulate an in vitro SBH experiment, the following operations were performed to prepare appropriate data.

Positions of sixty 5 kb overlapping "clones" were randomly defined, to simulate preparation of a basic library:

Positions of one thousand 500 bp "clones" were randomly determined to simulate making the ordering library. These fragments were extracted from the sequence. Random pools of 20 fragments were made, and k-tuple sets of pools were determined and stored on the hard disk. These data are used in the subfragment ordering phase: For the same density of clones 4 million clones in basic library and 3 million clones in ordering library are used for the entire human genome. The total number of 7 million clones is several fold smaller than the number of clones a few kb long for random cloning of almost all of genomic DNA and sequencing by a gel-based method.

From the data on the starts and ends of 5 kb fragments, 117 "informative fragments" were determined to be in the sequence. This was followed by determination of sets of overlapping k-tuples of which the single "informative fragment" consist. Only the subset of k-tuples matching a predetermined list were used. The list contained 65% 8-mers, 30% 9-mers, and 5% 10–12-mers. Processes of generation and the ordering of subfragments were performed on these data.

The testing of the algorithm was performed on the simulated data in two experiments. The sequence of 50 informative fragments was regenerated with the 100% correct data set (over 20,000 bp), and 26 informative fragments (about 10,000 bp) with 10% false k-tuples (5% positive and 5% negative ones).

In the first experiment, all subfragments were correct and in only one out of 50 informative fragments the sequence was not completely regenerated but remained in the form of 5 subfragments. The analysis of positions of overlapped fragments of ordering library has shown that they lack the information for the unique ordering of the 5 subfragments. The subfragments may be connected in two ways based on overlapping ends, 1-2-3-4-5 and 1-4-3-2-5. The only difference is the exchange of positions of subfragments 2 and 4. Since subfragments 2, 3, and 4 are relatively short (total of about 100 bp), the relatively greater chance existed, and occurred in this case, that none of the fragments of ordering library started or ended in the subfragment 3 region.

To simulate real sequencing, some false ("hybridization") data was included as input in a number of experiments. In oligomer hybridization experiments, under proposed conditions, the only situation producing unreliable data is the end mismatch versus full match hybridization. Therefore, in simulation only those k-tuples differing in a single element on either end from the real one were considered to be false positives. These "false" sets are made as follows. On the original set of a k-tuples of the informative fragment, a subset of 5% false positive k-tuples are added. False positive k-tuples are made by randomly picking a k-tuple from the set, copying it and altering a nucleotide on its beginning or end. This is followed by subtraction of a subset of 5% randomly chosen k-tuples. In this way the statistically expected number of the most complicated cases is generated in which the correct k-tuple is replaced with a k-tuple with the wrong base on the end.

Production of k-tuple sets as described leads to up to 10% of false data. This value varies from case to case, due to the randomness of choice of k-tuples to be copied, altered, and erased. Nevertheless, this percentage 3–4 times exceeds the amount of unreliable data in real hybridization experiments. The introduced error of 10% leads to the two fold increase in the number of subfragments both in fragments of basic library (basic library informative fragments) and in segments. About 10% of the final subfragments have a wrong base at the end as expected for the k-tuple set which contains false positives (see generation of primary subfragments). Neither the cases of misconnection of subfragments nor subfragments with the wrong sequence were observed. In 4 informative fragments out of 26 examined in the ordering process the complete sequence was not regenerated. In all 4 cases the sequence was obtained in the form of several longer subfragments and several shorter subfragments contained in the same segment. This result shows that the algorithmic principles allow working with a large percentage of false data.

The success of the generation of the sequence from its k-tuple content may be described in terms of completeness and accuracy. In the process of generation, two particular situations can be defined: 1) Some part of the information is missing in the generated sequence, but one knows where the ambiguities are and to which type they belong, and 2) the regenerated sequence that is obtained does not match the sequence from which the k-tuple content is generated, but the mistake can not be detected. Assuming the algorithm is developed to its theoretical limits, as in the use of the exact k-tuple sets, only the first situation can take place. There the incompleteness results in a certain number of subfragments that may not be ordered unambiguously and the problem of determination of the exact length of monotonous sequences, i.e. the number of perfect tandem repeats.

With false k-tuples, incorrect sequence may be generated. The reason for mistakes does not lie in the shortcomings of the algorithm, but in the fact that a given content of k-tuples unambiguously represents the sequence that differs from the original one. One may define three classes of error, depending on the kind of the false k-tuples present in the file. False negative k-tuples (which are not accompanied with the false positives) produce "deletions". False positive k-tuples are producing "elongations (unequal crossing over)". False positives accompanied with false negatives are the reason for generation of "insertions", alone or combined with "deletions". The deletions are produced when all of the k-tuples (or their majority) between two possible starts of the subfragments are false negatives. Since every position in the sequence is defined by k k-tuples, the occurrence of the deletions in a common case requires k consecutive false negatives. (With 10% of the false negatives and k=8, this situation takes place after every 108 elements). This situation is extremely infrequent even in mammalian genome sequencing using random libraries containing ten genome equivalents.

Elongation of the end of the sequence caused by false positive k-tuples is the special case of "insertions", since the end of the sequence can be considered as the endless linear array of false negative k-tuples. One may consider a group of false positive k-tuples producing subfragments longer than one k-tuple. Situations of this kind may be detected if subfragments are generated in overlapped fragments, like random physical fragments of the ordering library. An insertion, or insertion in place of a deletion, can arise as a result of specific combinations of false positive and false negative k-tuples. In the first case, the number of consecutive false negatives is smaller than k. Both cases require several overlapping false positive k-tuples. The insertions and deletions are mostly theoretical possibilities without sizable practical repercussions since the requirements in the number and specificity of false k-tuples are simply too high.

In every other situation of not meeting the theoretical requirement of the minimal number an the kind of the false positive and/or negatives, mistakes in the k-tuples content may produce only the lesser completeness of a generated sequence.

SBH, a sample nucleic acid is sequenced by exposing the sample to a support-bound probe of known sequence and a labeled probe or probes in solution. Wherever the probes ligase is introduced into the mixture of probes and sample, such that, wherever a support has a bound probe and a labeled probe hybridized back to back along the sample, the two probes will be chemically linked by the action of the ligase. After washing, only chemically linked support-bound and labeled probes are detected by the presence of the labeled probe. By knowing the identity of the support-bound probe at a particular location in an array, and the identity of the labeled probe, a portion of the sequence of the sample may be determined by the presence of a label at a point in an array on a Format with a sample of three substrate. And not chances not working are maximally overlapping sequences of all of the ligated probe pairs, the sequence of the sample may be reconstructed. Not of the sample to be sequenced may be a nucleic acid fragment or oligonucleotide of ten base pairs ("bp"). The sample is preferably four to one thousand bases in length.

The length of the probe is a fragment less than ten bases in length, and, preferably, is between four and nine bases in length. In this way, arrays of support-bound probes may include all oligonucleotides of a given length or may include only oligonucleotides selected for a particular test. Where all oligonucleotides of a given length are used, the number of central oligonucleotides may be calculated by $4^N$ where N is the length of the probe.

EXAMPLE 18
Re-Using Sequencing Chips

When ligation is employed in the sequencing process, then the ordinary oligonucleotide chip cannot be immediately reused. The inventor contemplates that this may be overcome in various ways.

One may employ ribonucleotides for the second probe, probe P, so that this probe may subsequently be removed by RNAse treatment. RNAse treatment may utilize RNAse A an endoribonuclease that specifically attacks single-stranded RNA 3 to pyrimidine residues and cleaves the phosphate linkage to the adjacent nucleotide. The end products are pyrimidine 3 phosphates and oligonucleotides with terminal pyrimidine 3 phosphates. RNAse A works in the absence of cofactors and divalent cations.

To utilize an RNAse, one would generally incubate the chip in any appropriate RNAse-containing buffer, as described by Sambrook et al. (1989; incorporated herein by reference). The use of 30–50 ul of RNAse-containing buffer per 8×8 mm or 9×9 mm array at 37° C. for between 10 and 60 minutes is appropriate. One would then wash with hybridization buffer.

Although not widely applicable, one could also use the uracil base, as described by Craig et al. (1989), incorporated herein by reference, in specific embodiments. Destruction of the ligated probe combination, to yield a re-usable chip, would be achieved by digestion with the *E. Coli* repair enzyme, uracil-DNA glycosylase which removes uracil from DNA.

One could also generate a specifically cleavable bond between the probes and then cleave the bond after detection. For example, this may be achieved by chemical ligation as described by Shabarova et al., (1991) and Dolinnaya et al., (1988), both references being specifically incorporated herein by reference.

Shabarova et al. (1991) describe the condensation of oligodeoxyribonucleotides with cyanogen bromide as a condensing agent. In their one step chemical ligation reaction, the oligonucleotides are heated to 97° C., slowly cooled to 0° C., then 1 ul 10 mM BrCN in acetonitrile is added.

Dolinnaya et al. (1988) show how to incorporate phosphoramidiate and pyrophosphate internucleotide bonds in DNA duplexes. They also use a chemical ligation method for modification of the sugar phosphate backbone of DNA, with a water-soluble carbodiimide (CDI) as a coupling agent. The selective cleavage of a phosphoamide bond involves contact with 15% $CH_3COOH$ for 5 min at 95° C. The selective cleavage of a pyrophosphate bond involves contact with a pyridine-water mixture (9:1) and freshly distilled $(CF_3CO)_2O$.

EXAMPLE 19
Diagnostics—Scoring Known Mutations or Full Gene Resequencing

In a simple case, the goal may be to discover whether selected, known mutations occur in a DNA segment. Less than 12 probes may suffice for this purpose, for example, 5 probes positive for one allele, 5 positive for the other, and 2 negative for both. Because of the small number of probes to be scored per sample, large numbers of samples may be analyzed in parallel. For example, with 12 probes in 3 hybridization cycles, 96 different genomic loci or gene segments from 64 patient may be analyzed on one 6×9 in membrane containing 12×24 subarrays each with 64 dots representing the same DNA segment from 64 patients. In this example, samples may be prepared in sixty-four 96-well plates. Each plate may represent one patient, and each well may represent one of the DNA segments to be analyzed. The samples from 64 plates may be spotted in four replicas as four quarters of the same membrane.

A set of 12 probes may be selected by single channel pipetting or by a single pin transferring device (or by an array of individually-controlled pipets or pins) for each of the 96 segments, and the selected probes may be arrayed in twelve 96-well plates. Probes may be labelled, if they are not prelabelled, and then probes from four plates may be mixed with hybridization buffer and added to the subarrays preferentially by a 96-channel pipeting device. After one hybridization cycle it is possible to strip off previously-applied probes by incubating the membrane at 37° to 55° C. in the preferably undiluted hybridization or washing buffer.

The likelihood that probes positive for one allele are positive and probes positive for the other allele are negative may be used to determine which of the two alleles is present. In this redundant scoring scheme, some level (about 10%) of errors in hybridization of each probe may be tolerated.

An incomplete set of probes may be used for scoring most of the alleles, especially if the smaller redundancy is sufficient, e.g. one or two probes which prove the presence or absence in a sample of one of the two alleles. For example, with a set of four thousand 8-mers there is a 91% chance of finding at least one positive probe for one of the two alleles for a randomly selected locus. The incomplete set of probes may be optimized to reflect G+C content and other biases in the analyzed samples.

For fall gene sequencing, genes may be amplified in an appropriate number of segments. For each segment, a set of probes (about one probe per 2–4 bases) may be selected and hybridized. These probes may identify whether there is a mutation anywhere in the analyzed segments. Segments (i.e., subarrays which contain these segments) where one or more mutated sites are detected may be hybridized with additional probes to find the exact sequence at the mutated sites. If a DNA sample is tested by every second 6-mer, and a mutation is localized at the position that is surrounded by positively hybridized probes TGCAAA and TATTCC and covered by three negative probes: CAAAAC, AAACTA and ACTATT, the mutated nucleotides must be A and/or C occurring in the normal sequence at that position. They may be changed by a single base mutation, or by a one or two nucleotide deletion and/or insertion between bases AA, AC or CT.

One approach is to select a probe that extends the positively hybridized probe TGCAAA for one nucleotide to the right, and which extends the probe TATTCC one nucleotide to the left. With these 8 probes (GCAAAA, GCAAAT, GCAAAC, GCAAAG and ATATTC, TTATTC, CTATTC, GTATTC) two questionable nucleotides are determined.

The most likely hypothesis about the mutation may be determined. For example, A is found to be mutated to G. There are two solutions satisfied by these results. Either replacement of A with G is the only change or there is in addition to that change an insertion of some number of bases between newly determined G and the following C. If the result with bridging probes is negative these options may then be checked first by at least one bridging probe comprising the mutated position (AAGCTA) and with an additional 8 probes: CAAAGA, CAAAGT, CAAAGC, CAAAGG and ACTATT, TCTATT, CCTATT, GCTATT, I. There are many other ways to select mutation-solving probes.

In the case of diploid, particular comparisons of scores for the test samples and homozygotic control may be performed to identify heterozygotes (see above). A few consecutive probes are expected to have roughly twice smaller signals if the segment covered by these probes is mutated on one of the two chromosomes.

EXAMPLE 20

Identification of Genes (Mutations) Responsible for Genetic Disorders and Other Traits Using universal sets of longer probes (8-mers or 9-mers) on immobilized arrays of samples, DNA fragments as long as 5–20 kb may be sequenced without subcloning. Furthermore, the speed of sequencing readily may be about 10 million bp/day/hybridization instrument. This performance allows for resequencing a large fraction of human genes or the human genome repeatedly from scientifically or medically interesting individuals. To resequence 50% of the human genes, about 100 million bp is checked. That may be done in a relatively short period of time at an affordable cost.

This enormous resequencing capability may be used in several ways to identify mutations and/or genes that encode for disorders or any other traits. Basically, mRNAs (which may be converted into cDNAs) from particular tissues or genomic DNA of patients with particular disorders may be used as starting materials. From both sources of DNA, separate genes or genomic fragments of appropriate length may be prepared either by cloning procedures or by in vitro amplification procedures (for example by PCR). If cloning is used, the minimal set of clones to be analyzed may be selected from the libraries before sequencing. That may be done efficiently by hybridization of a small number of probes, especially if a small number of clones longer than 5 kb is to be sorted. Cloning may increase the amount of hybridization data about two times, but does not require tens of thousands of PCR primers.

In one variant of the procedure, gene or genomic fragments may be prepared by restriction cutting with enzymes like Hga I which cuts DNA in following way: GACGC(N5')/ CTGCG(N10'). Protruding ends of five bases are different for different fragments. One enzyme produces appropriate fragments for a certain number of genes. By cutting cDNA or genomic DNA with several enzymes in separate reactions, every gene of interest may be excised appropriately. In one approach, the cut DNA is fractionated by size. DNA fragments prepared in this way (and optionally treated with Exonuclease III which individually removes nucleotides from the 3' end and increases length and specificity of the ends) may be dispensed in the tubes or in multiwell plates. From a relatively small set of DNA adapters with a common portion and a variable protruding end of appropriate length, a pair of adapters may be selected for every gene fragment that needs to be amplified. These adapters are ligated and then PCR is performed by universal primers. From 1000 adapters, a million pairs may be generated, thus a million different fragments may be specifically amplified in the identical conditions with a universal pair of primers complementary to the common end of the adapters.

If a DNA difference is found to be repeated in several patients, and that sequence change is nonsense or can change function of the corresponding protein, then the mutated gene may be responsible for the disorder. By analyzing a significant number of individuals with particular traits, functional allelic variations of particular genes could be associated by specific traits.

This approach may be used to eliminate the need for very expensive genetic mapping on extensive pedigrees and has special value when there is no such genetic data or material.

EXAMPLE 21

Scoring Single Nucleotide Polymorphisms in Genetic Mapping

Techniques disclosed in this application are appropriate for an efficient identification of genomic fragments with single nucleotide polymorphisms (SNUPs). In 10 individuals by applying the described sequencing process on a large number of genomic fragments of known sequence that may be amplified by cloning or by in vitro amplification, a sufficient number of DNA segments with SNUPs may be identified. The polymorphic fragments are further used as SNUP markers. These markers are either mapped previously (for example they represent mapped STSs) or they may be mapped through the screening procedure described below.

SNUPs may be scored in every individual from relevant families or populations by amplifying markers and arraying them in the form of the array of subarrays. Subarrays contain the same marker amplified from the analyzed individuals. For each marker, as in the diagnostics of known mutations, a set of 6 or less probes positive for one allele and 6 or less probes positive for the other allele may be selected and scored. From the significant association of one or a group of the markers with the disorder, chromosomal position of the responsible gene(s) may be determined. Because of the high throughput and low cost, thousands of markers may be scored for thousands of individuals. This amount of data allows localization of a gene at a resolution level of less than one million bp as well as localization of genes involved in polygenic diseases. Localized genes may be identified by sequencing particular regions from relevant normal and affected individuals to score a mutation(s).

PCR is preferred for amplification of markers from genomic DNA. Each of the markers require a specific pair of primers. The existing markers may be convertible or new markers may be defined which may be prepared by cutting genomic DNA by Hga I type restriction enzymes, and by ligation with a pair of adapters.

SNUP markers can be amplified or spotted as pools to reduce the number of independent amplification reactions. In this case, more probes are scored per one sample. When 4 markers are pooled and spotted on 12 replica membranes, then 48 probes (12 per marker) may be scored in 4 cycles.

EXAMPLE 22

Detection and Verification of Identity of DNA Fragments

DNA fragments generated by restriction cutting, cloning or in vitro amplification (e.g. PCR) frequently may be identified in a experiment. Identification may be performed by verifing the presence of a DNA band of specific size on gel electrophoresis. Alternatively, a specific oligonucleotide may be prepared and used to verify a DNA sample in question by hybridization. The procedure developed here allows for more efficient identification of a large number of samples without preparing a specific oligonucleotide for each fragment. A set of positive and negative probes may be selected from the universal set for each fragment on the basis of the known sequences. Probes that are selected to be positive usually are able to form one or a few overlapping groups and negative probes are spread over the whole insert.

This technology may be used for identification of STSs in the process of their mapping on the YAC clones. Each of the STSs may be tested on about 100 YAC clones or pools of YAC clones. DNAs from these 100 reactions possibly are spotted in one subarray. Different STSs may represent consecutive subarrays. In several hybridization cycles, a signature may be generated for each of the DNA samples, which signature proves or disproves existence of the particular STS in the given YAC clone with necessary confidence.

To reduce the number of independent PCR reactions or the number of independent samples for spotting, several STSs may be amplified simultaneously in a reaction or PCR samples may be mixed, respectively. In this case more probes have to be scored per one dot. The pooling of STSs is independent of pooling YACs and may be used on single YACs or pools of YACs. This scheme is especially attractive when several probes labelled with different colors are hybridized together.

In addition to confirmation of the existence of a DNA fragment in a sample, the amount of DNA may be estimated using intensities of the hybridization of several separate probes or one or more pools of probes. By comparing obtained intensities with intensities for control samples having a known amount of DNA, the quantity of DNA in all spotted samples is determined simultaneously. Because only a few probes are necessary for identification of a DNA fragment, and there are N possible probes that may be used for DNA N bases long, this application does not require a large set of probes to be sufficient for identification of any DNA segment. From one thousand 8-mers, on average about 30 full matching probes may be selected for a 1000 bp fragment.

EXAMPLE 23

Identification of Infectious Disease Organisms and Their Variants

DNA-based tests for the detection of viral, bacterial, fungal and other parasitic organisms in patients are usually more reliable and less expensive than alternatives. The major advantage of DNA tests is to be able to identify specific strains and mutants, and eventually be able to apply more effective treatment. Two applications are described below.

The presence of 12 known antibiotic resistance genes in bacterial infections may be tested by amplifying these genes. The amplified products from 128 patients may be spotted in two subarrays and 24 subarrays for 12 genes may then be repeated four times on a 8×12 cm membrane. For each gene, 12 probes may be selected for positive and negative scoring. Hybridizations may be performed in 3 cycles. For these tests, a much smaller set of probes is most likely to be universal. For example, from a set of one thousand 8-mers, on average 30 probes are positive in 1000 bp fragments, and 10 positive probes are usually sufficient for a highly reliable identification. As described in Example 9, several genes may be amplified and/or spotted together and the amount of the given DNA may be determined. The amount of amplified gene may be used as an indicator of the level of infection.

Another example involves possible sequencing of one gene or the whole genome of an HIV virus. Because of rapid diversification, the virus poses many difficulties for selection of an optimal therapy. DNA fragments may be amplified from isolated viruses from up to 64 patients and resequenced by the described procedure. On the basis of the obtained sequence the optimal therapy may be selected. If there is a mixture of two virus types of which one has the basic sequence (similar to the case of heterozygotes), the mutant may be identified by quantitative comparisons of its hybridization scores with scores of other samples, especially control samples containing the basic virus type only. Scores twice as small may be obtained for three to four probes that cover the site mutated in one of the two virus types present in the sample (see above).

EXAMPLE 24

Forensic and Parental Identification

Sequence polymorphisms make an individual genomic DNA unique. This permits analysis of blood or other body fluids or tissues from a crime scene and comparison with samples from criminal suspects. A sufficient number of polymorphic sites are scored to produce a unique signature of a sample. SBH may easily score single nucleotide polymorphisms to produce such signatures.

A set of DNA fragments (10–1000) may be amplified from samples and suspects. DNAs from samples and suspects representing one fragment are spotted in one or several subarrays and each subarray may be replicated 4 times. In three cycles, 12 probes may determine the presence of allele A or B in each of the samples, including suspects, for each DNA locus. Matching the patterns of samples and suspects may lead to discovery of the suspect responsible for the crime.

The same procedure may be applicable to prove or disprove the identity of parents of a child. DNA may be prepared and polymorphic loci amplified from the child and adults; patterns of A or B alleles may be determined by hybridization for each. Comparisons of the obtained patterns, along with positive and negative controls, aide in the determination of familial relationships. In this case, only a significant portion of the alleles need match with one parent for identification. Large numbers of scored loci allow for the avoidance of statistical errors in the procedure or of masking effects of de novo mutations.

EXAMPLE 25
Assessing Genetic Diversity of Populations or Species and Biological Diversity of Ecological Niches Measuring the frequency of allelic variations on a significant number of loci (for example, several genes or entire mitochondrial DNA) permits development of different types of conclusions, such as conclusions regarding the impact of the environment on the genotypes, history and evolution of a population or its susceptibility to diseases or extinction, and others. These assessments may be performed by testing specific known alleles or by full resequencing of some loci to be able to define de novo mutations which may reveal fine variations or presence of mutagens in the environment.

Additionally, biodiversity in the microbial world may be surveyed by resequencing evolutionarily conserved DNA sequences, such as the genes for ribosomal RNAs or genes for highly conservative proteins. DNA may be prepared from the environment and particular genes amplified using primers corresponding to conservative sequences. DNA fragments may be cloned preferentially in a plasmid vector (or diluted to the level of one molecule per well in multiwell plates and than amplified in vitro). Clones prepared this way may be resequenced as described above. Two types of information are obtained. First of all, a catalogue of different species may be defined as well as the density of the individuals for each species. Another segment of information may be used to measure the influence of ecological factors or pollution on the ecosystem. It may reveal whether some species are eradicated or whether the abundance ratios among species is altered due to the pollution. The method also is applicable for sequencing DNAs from fossils.

EXAMPLE 26
Detection or Quantification of Nucleic Acid Species

DNA or RNA species may be detected and quantified by employing a probe pair including an unlabeled probe fixed to a substrate and a labeled probe in a solution. The species may be detected and quantified by exposure to the unlabeled probe in the presence of the labeled probe and ligase. Specifically, the formation of an extended probe by ligation of the labeled and unlabeled probe on the sample nucleic acid backbone is indicative of the presence of the species to be detected. Thus, the presence of label at a specific point in the array on the substrate after removing unligated labeled probe indicates the presence of a sample species while the quantity of label indicates the expression level of the species.

Alternatively, one or more unlabeled probes may be arrayed on a substrate as first members of pairs with one or more labeled probes to be introduced in solution. According to one method, multiplexing of the label on the array may be carried out by using dyes which fluoresce at distinguishable wavelengths. In this manner, a mixture of cDNAs applied to an array with pairs of labeled and unlabeled probes specific for species to be identified may be examined for the presence of and expression level of cDNA species. According to a preferred embodiment this approach may be carried out to sequence portions of cDNAs by selecting pairs of unlabeled and labeled probes pairs comprising sequences which overlap along the sequence of a cDNA to be detected.

Probes may be selected to detect the presence and quantity of particular pathogenic organisms genome by including in the composition selected probe pairs which appear in combination only in target pathogenic genome organisms. Thus, while no single probe pair may necessarily be specific for the pathogenic organism genome, the combination of pairs is. Similarly, in detecting or sequencing cDNAs, it might occur that a particular probe is not be specific for a cDNA or other type of species. Nevertheless, the presence and quantity of a particular species may be determined by a result wherein a combination of selected probes situated at distinct array locations is indicative of the presence of a particular species.

An infectious agent with about 10 kb or more of DNA may be detected using a support-bound detection chip without the use of polymerase chain reaction (PCR) or other target amplification procedures. According to other methods, the genomes of infectious agents including bacteria and viruses are assayed by amplification of a single target nucleotide sequence through PCR and detection of the presence of target by hybridization of a labelled probe specific for the target sequence. Because such an assay is specific for only a single target sequence it therefore is necessary to amplify the gene by methods such as PCR to provide sufficient target to provide a detectable signal.

According to this example, an improved method of detecting nucleotide sequences characteristic of infectious agents through a Format 3-type reaction is provided wherein a solid phase detection chip is prepared which comprises an array of multiple different immobilized oligonucleotide probes specific for the infectious agent of interest. A single dot comprising a mixture of many unlabeled probes complementary to the target nucleic acid concentrates the label specific to a species at one location thereby improving sensitivity over diffuse or single probe labeling. Such multiple probes may be of overlapping sequences of the target nucleotide sequence but may also be non-overlapping sequences as well as non-adjacent. Such probes preferably have a length of about 5 to 12 nucleotides.

A nucleic acid sample exposed to the probe array and target sequences present in the sample will hybridize with the multiple immobilized probes. A pool of multiple labeled probes selected to specifically bind to the target sequences adjacent to the immobilized probes is then applied with the sample to an array of unlabeled oligonucleotide probe mixtures. Ligase enzyme is then applied to the chip to ligate the adjacent probes on the sample. The detection chip is then washed to remove unhybridized and unligated probe and sample nucleic acids and the presence of sample nucleic acid may be determined by the presence or absence of label. This method provides reliable sample detection with about a 1000-fold reduction of molarity of the sample agent.

As a further aspect of the invention, the signal of the labelled probes may be amplified by means such as providing a common tail to the free probe which itself comprises multiple chromogenic, enzymatic or radioactive labels or which is itself susceptible to specific binding by a further probe agent which is multiply labelled. In this way, a second round of signal amplification may be carried out. Labeled or unlabeled probes may be used in a second round of amplification. In this second round of amplification, a lengthy DNA sample with multiple labels may result in an increased amplification intensity signal between 10 to 100 fold which may result in a total signal amplification of 100,000 fold. Through the use of both aspects of this example, an intensity signal approximately 100,000 fold may give a positive result of probe-DNA ligation without having to employ PCR or other amplification procedures.

According to a further aspect of the invention an array or super array may be prepared which consists of a complete set of probes, for example 4096 6-mer probes. Arrays of this type are universal in a sense that they can be used for detection or partial to complete sequencing of any nucleic acid species. Individual spots in an array may contain single probe species or mixtures of probes, for example N(1–3) B(4–6) N(1–3) type of mixtures that are synthesized in the single reaction (N represents all four nucleotides, B one specific nucleotide and where the associated numbers are a range of numbers of bases i.e., 1–3 means "from one to three bases".) These mixtures provide stronger signal for a nucleic acid species present at low concentration by collecting signal from different parts of the same long nucleic acid species molecule. The universal set of probes may be subdivided in many subsets which are spotted as unit arrays separated by barriers that prevent spreading of hybridization buffer with sample and labeled probe(s).

For detection of a nucleic acid species with a known sequence one of more oligonucleotide sequences comprising both unlabelled fixed and labeled probes in solution may be selected. Labeled probes are synthesized or selected from the presynthesized complete sets of, for example, 7-mers. The labeled probes are added to corresponding unit arrays of fixed probes such that a pair of fixed and labeled probes will adjacently hybridize to the target sequence such that upon administration of ligase the probes will be covalently bound.

If a unit array contains more than one fixed probe (as separated spots or within the same spot) that are positive in a given nucleic acid species all corresponding labeled probes may be mixed and added to the same unit array. The mixtures of labeled probes are even more important when mixtures of nucleic acid species are tested. One example of a complex mixture of nucleic acid species are mRNAs in one cell or tissue.

According to one embodiment of the invention unit arrays of fixed probes allow use of every possible immobilized probe with cocktails of a relatively small number of labeled probes. More complex cocktails of labeled probes may be used if a multiplex labeling scheme is implemented. Preferred multiplexing methods may use different fluorescent dyes or molecular tags that may be separated by mass spectroscopy.

Alternatively, according to a preferred embodiment of the invention, relatively short fixed probes may be selected which frequently hybridize to many nucleic acid sequences. Such short probes are used in combination with a cocktail of labeled probes which may be prepared such that at least one labeled probe corresponds to each of the fixed proves. Preferred cocktails are those in which none of the labeled probes corresponds to more than one fixed probe.

EXAMPLE 27
Interrogation of Segments of the HIV Virus with All Possible 10-mers

In this example of Format III SBH, an array was generated on nylon membranes (e.g., Gene Screen) of all possible bound 5-mers (1024 possible pentamers). The bound 5-mer oligonucleotides were synthesized with 5' tails of 5'-TTTTTT-NNN-3' (N=all four bases A, C, G, T, at this step in the synthesis equal molar amounts of all four bases are added). These oligonucleotides were precisely spotted onto the nylon membrane, the spots were allowed to dry, and the oligonucleotides were immobilized by treating the dried spots with UV light. Oligonucleotide densities of up to 18 oligonucleotides per square nanometer were obtained using this method. After the UV treatment, the nylon membranes were treated with a detergent containing buffer at 60–80° C. The spots of oligonucleotides were gridded in subarrays of 10 by 10 spots, and each subarray has 64 5-mer spots and 36 control spots. 16 subarrays give 1024 5-mers which encompasses all possible 5-mers.

The subarrays in the array were partitioned from each other by physical barriers, e.g., a hydrophobic strip, that allowed each subarray to be hybridized to a sample without cross-contamination from adjacent subarrays. In a preferred embodiment, the hydrophobic strip is made from a solution of silicone (e.g., household silicone glue and seal paste) in an appropriate solvent (such solvents are well known in the art). This solution of silicone grease is applied between the subarrays to form lines which after the solvent evaporates act as hydrophobic strips separating the cells.

In this Format III example, the free or solution (nonbound) 5-mers were synthesized with 3' tails of 5'-NN-3' (N=all four bases A, C, G, T). In this embodiment, the free 5-mers and the bound 5-mers are combined to produce all possible 10-mers for sequencing a known DNA sequence of less than 20 kb. 20 kb of double stranded DNA is denatured into 40 kb of single-stranded DNA. This 40 kb of ss DNA hybridizes to about 4% of all possible 10-mers. This low frequency of 10-mer binding and the known target sequence allow the pooling of free or solution (nonbound) 5-mers for treatment of each subarray, without a loss of sequence information. In a preferred embodiment, 16 probes are pooled for each subarray, and all possible 5-mers are represented in 64 total pools of free 5-mers. Thus, all possible 10-mers may be probed against a DNA sample using 1024 subarrays (16 subarrays for each pool of free 5-mers).

The target DNA in this embodiment represents two-600 bp segments of the HIV virus. These 600 bp segments are represented by pools of 60 overlapping 30-mers (the 30-mers overlap each adjacent 30 mer by 20 nucleotides). The pools of 30-mers mimic a target DNA that has been treated using techniques well known in the art to shear, digest, and/or random PCR the target DNA to produce a random pool of very small fragments.

As described above in the previous Format III examples, the free 5-mers are labeled with radioactive isotopes, biotin, fluorescent dyes, etc. The labeled free 5-mers are then hybridized along with the bound 5-mers to the target DNA, and ligated. In a preferred embodiment, 300–1000 units of ligase are added to the reaction. The hybridization conditions were worked out following the teachings of the previous examples. Following ligation and removal of the target DNA and excess free probe, the array is assayed to determine the location of labeled probes (using the techniques described in the examples above).

The known DNA sequence of the target, and the known free and bound 5-mers in each subarray, predict which bound 5-mers will be ligated to a labeled free 5-mer in each subarray. The signal from 20 of these predicted dots were lost and 20 new signals were gained for each change in the target DNA from the predicted sequence. The overlapping sequence of the bound 5-mers in these ten new dots identifies which free, labeled 5-mer is bound in each new dot.

Using the described methods, arrays and pools of free, labeled 5-mers, the test HIV DNA sequence was probed with all possible 10-mers. Using this Format III approach, we properly identified the "wild-type" sequence of the segments tested, as well as several sequence "mutants" that were introduced into these segments.

EXAMPLE 28
Sequencing of Repetitive DNA Sequences

In one embodiment, repetitive DNA sequences in the target DNA are sequenced with "spacer oligonucleotides" in a modified Format III approach. Spacer oligonucleotides of varying lengths of the repetitive DNA sequence (the repeating sequence is identified on a first SBH run) are hybridized to the target DNA along with a first known adjoining oligonucleotide and a second known, or group of possible oligonucleotides adjoining the other side of the spacer (known from the first SBH run). When a spacer matching the length of the repetitive DNA segment is hybridized to the target, the two adjacent oligonucleotides can be ligated to the spacer. If the first known oligonucleotide is fixed to a substrate, and the second known or possible oligonucleotide (s) is labeled, a bound ligation product including the labeled second known or possible oligonucleotide(s) is formed when a spacer of the proper length is hybridized to the target DNA.

EXAMPLE 29

Sequencing Through Branch Points with Format III SBH

In one embodiment, branch points in the target DNA are sequenced using a third set of oligonucleotides and a modified Format III approach. After a first SBH run, several branch points may be identified when the sequence is compiled. These can be solved by hybridizing oligonucleotide(s) that overlap partially with one of the known sequences leading into the branch point and then hybridizing to the target an additional oligonucleotide that is labeled and corresponds to one of the sequences that comes out of the branch point. When the proper oligonucleotides are hybridized to the target DNA, the labeled oligonucleotide can be ligated to the other(s). In a preferred embodiment, a first oligonucleotide that is offset by one to several nucleotides from the branch point is selected (so that it reads into one of the branch sequences), a second oligonucleotide reading from the first and into the branch point sequence is also selected, and a set of third oligonucleotides that correspond to all the possible branch sequences with an overlap of the branch point sequence by one or a few nucleotides (corresponding to the first oligonucleotide) is selected. These oligonucleotides are hybridized to the target DNA, and only the third oligonucleotide with the proper branch sequence (that matches the branch sequence of the first oligonucleotide) will produce a ligation product with the first and second oligonucleotides.

EXAMPLE 30

Multiplexing Probes for Analyzing a Target Nucleic Acid

In this Example, sets of probes are labeled with different labels so that each probe of a set can be differentiated from the other probes in the set. Thus, the set of probes may be contacted with target nucleic acid in a single hybridization reaction without the loss of any probe information. In preferred embodiments, the different labels are different radioisotopes, or different flourescent labels, or different EMLs. These sets of probes may be used in either Format I, Format II or Format III SBH.

In Format I SBH, the set of differently labeled probes are hybridized to target nucleic acid which is fixed to a substrate under conditions that allow differentiation between perfect matches one base-pair mismatches. Specific probes which bind to the target nucleic acid are identified by their different labels and perfect matches are determined, at least in part, from this binding information.

In Format II SBH, the target nucleic acids are labeled with different probes and hybridized to arrays of probes. Specific target nucleic acids which bind to the probes are identified by their different labels and perfect matches are determined, at least in part, form this binding information.

In Format III SBH, the set of differently labeled probes and fixed probes are hybridized to a target nucleic acid under conditions that allow perfect matches to be differentiated from one base-pair mismatches. Labeled probes that are adjacent, on the target, to a fixed probe are bound to the fixed probe, and these products are detected and differentiated by their different labels.

In a preferred embodiment, the different labels are EMLs, which can be detected by electron capture mass spectrometry (EC-MS). EMLs may be prepared from a variety of backbone molecules, with certain aromatic backbones being particularly preferred, e.g., see Xu et al., J. Chromatog. 764:95–102 (1997). The EML is attached to a probe in a reversible and stable manner, and after the probe is hybridized to target nucleic acid, the EML is removed from the probe and identified by standard EC-MS (e.g., the EC-MS may be done by a gas chromatograph-mass spectrometer).

EXAMPLE 31

Detection of Low Frequency Target Nucleic Acids

Format III SBH has sufficient discrimination power to identify a sequence that is present in a sample at 1 part to 99 parts of a similar sequence that differs by a single nucleotide. Thus, Format III can be used to identify a nucleic acid present at a very low concentration in a sample of nucleic acids, e.g., a sample derived from blood.

In one embodiment, the two sequences are for cystic fibrosis and the sequences differ from each other by a deletion of three nucleotides. Probes for the two sequences were as follows, probes distinguishing the deletion from wild type were fixed to a substrate, and a labeled contiguous probe was common to both. Using these targets and probes, the deletion mutant could be detected with Format III SBH when it was present at one part to ninety nine parts of the wild-type.

EXAMPLE 32

Polaroid Apparatus and Method for Analyzing a Target Nucleic Acid

An apparatus for analyzing a nucleic acid can be constructed with two arrays of nucleic acids, and an optional material that prevents the nucleic acids of the two arrays from mixing until such mixing is desired. The arrays of the apparatus may be supported by a variety of substrates, including but not limited to, nylon membranes, nitrocellulose membranes, or other materials disclosed above. In preferred embodiments, one of the substrate is a membrane separated into sectors by hydrophobic strips, or a suitable support material with wells which may contain a gel or sponge. In this embodiment, probes are placed on a sector of the membrane, or in the well, the gel, or sponge, and a solution (with or without target nucleic acids) is added to the membrane or well so that the probes are solubilized. The solution with the solubilized probes is then allowed to contact the second array of nucleic acids. The nucleic acids may be, but are not limited to, oligonucleotide probes, or target nucleic acids, and the probes or target nucleic acids may be labeled. The nucleic acids may be labeled with any labels conventionally used in the art, including but not limited to radioisotopes, fluorescent labels or electrophore mass labels.

The material which prevents mixing of the nucleic acids may be disposed between the two arrays in such a way that when the material is removed the nucleic acids of the two arrays mix together. This material may be in the form of a sheet, membrane, or other barrier, and this material may be comprised of any material that prevents the mixing of the nucleic acids.

This apparatus may be used in Format I SBH as follows: a first array of the apparatus has target nucleic acids that are fixed to the substrate, and a second array of the apparatus has nucleic acid probes that are labeled and can be removed to interrogate the target nucleic acid of the first array. The two arrays are optionally separated by a sheet of material that prevents the probes from contacting the target nucleic acid, and when this sheet is removed the probes can interrogate the target. After appropriate incubation and (optionally) washing steps the array of targets may be "read" to determine which probes formed perfect matches with the target. This reading may be automated or can be done manually (e.g., by eye with an autoradiogram). In Format II SBH, the procedure followed would be similar to that described above except that the target is labeled and the probes are fixed.

Alternatively, the apparatus may be used in Format III SBH as follows: two arrays of nucleic acid probes are formed, the nucleic acid probes of either or both arrays may be labeled, and one of the arrays may be fixed to its substrate. The two arrays are separated by a sheet of material that prevents the probes from mixing. A Format II reaction is initiated by adding target nucleic acid and removing the sheet allowing the probes to mix with each other and the target. Probes which bind to adjacent sites on the target are bound together (e.g., by base-stacking interactions or by covalently joining the backbones), and the results are read to determine which probes bound to the target at adjacent sites. When one set of probes is fixed to the substrate, the fixed array can be read to determine which probes from the other array are bound together with the fixed probes. As with the above method, this reading may be automated (e.g., with an ELISA reader) or can be done manually (e.g., by eye with an autoradiogram).

EXAMPLE 33
Three Dimensional Arrays of Probes

In a preferred embodiment, the oligonucleotide probes are fixed in a three-dimensional array. The three-dimensional array is comprised of multiple layers, such that each layer may be analyzed separate and apart from the other layers, or all the layers of the three-dimensional array may be simultaneously analyzed. Three dimensional arrays include, for example, an array disposed on a substrate having multiple depressions with probes located at different depths within the depressions (each level is made up of probes at similar depths within the depression); or an array disposed on a substrate having depressions of different depths with the probes located at the bottom of the depression, at the peaks separating the depressions or some combination of peaks and depressions (each level is made up of all probes at a certain depth); or an array disposed on a substrate comprised of multiple sheets that are layered to form a three-dimensional array.

Materials for synthesizing these three-dimensional arrays are well known in the art, and include the materials previously recited in this specification as suitable as supports for probe arrays. In addition, other suitable materials which can support oligonucleotide probes, and which preferably, are flexible may be used as substrates.

EXAMPLE 34
Signature Processing for Clustering cDNA Clones

A plurality of distinct nucleic acid sequences were obtained from cDNA library, using standard pcr, SBH sequence signature analysis and Sanger sequencing techniques. The inserts of the library were amplified with per using primers specific for vector sequences which flank the inserts. These samples were spotted onto nylon membranes and interrogated with suitable number of oligonucleotide probes and the intensity of positive binding probes was measured giving sequence signatures. The clones were clustered into groups of similar or identical sequence signatures, and single representative clones were selected from each group for gel sequencing. The 5' sequence of the amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer. The majority of clones which were selected and sequenced by this method had sequences which differed from each other, and a very small number had the same sequence.

EXAMPLE 35
High-Throughput Production of Chips

In a preferred embodiment, an apparatus for mass producing arrays of probes may comprise a rotating drum or plate coupled with an ink-jet deposition apparatus, for example, a microdrop dosing head; and a suitable robotics systems, for example, an anorad gantry.

The apparatus comprises a cylinder to which a suitable substrate is fixed. The substrate may be any of the materials previously described as suitable for an array of probes. In a preferred embodiment, the substrate is a flexible material, and the arrays are made directly on the substrate. In alternative embodiments, a flexible substrate is fixed to the cylinder and individual chips are fixed on the substrate. The arrays are then made on each individual chip.

In a preferred embodiment, physical barriers are applied to the substrate or chip and define an array of wells. The physical barriers may be applied to the substrate or chip by the apparatus, or alternatively, the physical barriers are applied to the chips or substrate before they are fixed to the cylinder. A single spot of oligonucleotide probes is then placed into each well, wherein the probes placed into an individual well may all have the same sequence, or the probes spotted into an individual well may have different sequences. In a more preferred embodiment, the probe or probes spotted into each individual well in an array are different from the probe or probes spotted in the other wells of the array. Sequencing chips comprising multiple arrays can then be assembled from these arrays.

After the substrate or substrate and chips are fixed to the cylinder, a motor rotates the cylinder. The cylinder's rotation speed is precisely determined by any of the ways well known in the art, including, for example using a fixed optical sensor and light source that rotates with the cylinder. A dispensing apparatus moves along an arm and can deliver probes or other reagents through a dispensing tip to precise locations on the substrate or chips using the precise rotation speed calculated above, by methods well known in the art. The dispensing apparatus receives probes or reagents from the reservoir through the feeding line. The reservoir holds all the necessary probes and other reagents for making the arrays.

The dispensing apparatus may have one or multiple dispensing tips. Each dispensing tip has a sample well in a body that receives probes or other reagents through a sample line. The pressure line pressurizes the chamber to a psi sufficient to force probes or reagents through the dispensing tip. The sample line, well and dispensing tip must be flushed between each change in probe or reagent. An appropriate washing buffer is supplied through sample line or through an optional dedicated washing line to the sample well or optionally a portion or all of the chamber may be filled with washing buffer. The washing buffer is then removed from the sample well and chamber if necessary by an evacuation line or through the sample line and dispensing tip.

When the dispensing means has applied probes to all the appropriate sites in each array or chip, the substrate (with or without chips) is removed from the cylinder and a new substrate is fixed to the cylinder.

EXAMPLE 36

Analysis of a Target Nucleic Acid with Probes Complexed to Discrete Particles In this embodiment, a target nucleic acid is interrogated with probes that are complexed (covalent or noncovalent) to a plurality of discrete particles. The discrete particles can be discriminated from each other based on a physical property (or a combination of physical properties), and particles with differentiated by the physical property are complexed with different probes. In a preferred embodiment, the probe is an oligonucleotide of a known sequence and length. Thus, a probe may be identified by the physical property of the discrete particle. Suitable probes for this embodiment include all the probes that are described above in previous sections, including probes which are shorter in an informative sense than the probes full length.

The physical property of the discrete particle may be any property, well known in the art, which allows particles to be differentiated into sets. For example, the particles could be differentiated into sets based on their size, flourescence, absorbance, electromagnetic charge, or weight, or the particles could be labeled with dyes, radionuclides, or EMLs. Other suitable labels include ligands which can serve as specific binding members to a labeled antibody, chemiluminescers, enzymes, antibodies which can serve as a specific binding pair member for a labeled ligand, and the like. A wide variety of labels have been employed in immunoassays which can readily be employed. Still other labels include antigens, groups with specific reactivity, and electrochemically detectable moieties. Still further labels, include any of the labels recited above in previous sections. These labels and properties may be measured quantitatively by methods well known in the art, including for example, those methods described above in previous sections, and the particles may be differentiated on the basis of signal intensity or signal type (for one of the labels, e.g., different dye densities may be applied to a particle, or different types of dyes). In a preferred embodiment, several physical properties are combined and the different combinations of properties allow discrimination of the particles (e.g., ten sizes and ten colors could be combined to differentiate 100 particle groups).

The particle-probes allow the exploitation of standard combinatorial approaches so that, for example, all possible 10-mers can be synthesized using about 2000 reaction containers. A first set of 1024 reactions are done to synthesize all possible 5-mers on 1024 differentially labeled particles. The resulting probe-particles are mixed together, and split into another set of 1024 reaction containers. A second set of reactions are done with these samples to synthesize all possible 5-mer extensions on the probes in the pools of particles. The physical property identifies the first five nucleotides of each probe and the reaction container will identify the identity of the second five nucleotides of every probe. Thus, all possible 10-mer probes are synthesized using 2048 reaction containers. This approach is easily modified to make all possible n-mers for a large range of probe lengths.

In a preferred embodiment, the particles are separated into sets by the intensity of flourescence of the particles. The particles in each set are prepared with varying densities of flourescent label, and thus, the particles have different flourescence intensities. The flourescent intensity of flourescein is related to concentration over a range of 1:300 to 1:300,000 (Lockhart et al., 1986), and between 1:3000 to 1:300,000 there is a linear relationship (so the flourescein intensity is linear over a range of about 1–300). In the linear range of detection, 256 sets of particles are labeled with flourescein (e.g., 3–259). 256 sets of particles allows all possible 4-mers to be attached to different sets of particles. By pooling the particles, all possible 5-mers can be made by having four pools of all possible 4-mers and then extending the probes in each pool by A, G, C, or T. Similarly, all possible 6-mers can be made by having 16 pools of all possible 4-mers in which each pool of 4-mers is extended by one of the 16 possible two base permutations of A, G, C, and T (etc. for 7-mers there are 64 pools, 8-mers there are 256 pools, and so forth).

The 5-mer probes (in four pools) are used to interrogate a target nucleic acid. The target nucleic acid is labeled with another flourescent dye, or other different label (as described above). Labeled target is mixed with the four pools, and complementary probes in each pool hybridize to the target nucleic acid. These hybridization complexes are detected by methods well-known in the art, and the positively hybridizing probes are then identified by detecting the flourescence intensity of the particle. In a most preferred embodiment, the mixture of probe-particles and target nucleic acid are fed through a flow-cytometer or other separating instrument one particle at a time, and the particle label and the target are measured to determine which probes are complementary to the target nucleic acid.

In an alternative embodiment, a set of free probes is labeled with another flourescent dye, or other label (as described above), and individual free probes are mixed with each pool of 5-mer probes (four pools) and then the mixtures are hybridized with the target nucleic acid. An agent is added to covalently attach free probe to 5-mer probe (see previous sections for a description of suitable agents), when the free probe is bound to a site on the target nucleic acid that is adjacent to the site on which the 5-mer probe is bound (the free probe site must be adjacent the end of the 5-mer probe which can be ligated). The particles are then assayed, by methods well known in the art, to determine which particles have been covalently coupled to the free probe, i.e., the particles which have the free probe label, and the 5-mer probe is identified by the flourescent intensity of the particle. In a most preferred embodiment, the mixture of probe-particles, free probes, and target nucleic acid are fed through a flow-cytometer one particle at a time, and the particle label and the free probe label are measured to determine which probes are complementary to the target nucleic acid.

In preferred embodiment, a single apparatus houses all or most of the manipulations for an analysis of a target nucleic acid with the probe-particle complexes. The apparatus has one or more reagent chambers in which buffer and labeled target nucleic acid are thoroughly mixed (target nucleic acid may be added manually or automatically). The mixture is aliquoted from the reagent chamber into a plurality of reaction chambers, and each reaction chamber has a pool of probe-particle complexes. The probe-particles and target nucleic acid react under conditions which allow complementary probes to bind with the target nucleic acid. Excess target nucleic acid, i.e., nonbound, is removed from the reaction chamber (e.g., by washing), and the particles bound to target nucleic acid are identified by the association of target nucleic acid label with the particles, and the probe is identified by the physical property of the particle. In a preferred embodiment, after removing excess target, the particles move single file through a channel from the reaction chamber to the detecting device(s). As single particles move past the detecting device(s) they measure the target label and the physical property of the particle. In an alternative preferred embodiment, before or after removing excess target, the particles are fractionated, for example, by size (e.g., exclusion chromatography), charge (e.g., ion exchange chromatography), and/or density-weight into their sets using one or a combinations of these physical properties. These fractionated particles are then assayed by the detecting device(s).

In an alternative of this embodiment, the main reagent chamber is supplied with buffer, target nucleic acid, a pool of probe-particle complexes, and a chemical or enzymatic ligating reagent. These components are thoroughly mixed and then aliquoted from the reagent chamber into a plurality of reaction chambers. Each of the reaction chambers has a labeled free probe. Alternatively, the pool of probe particle complexes may be placed in the reaction chamber with the free probe instead of adding them to the reagent chamber. Additionally, the free probes could be added to the reagent chamber, and the pool of probe particles could be added to the reaction chamber. The probe-particles, target nucleic acid, and free probe react under conditions which allow free- and particle-probes to bind with adjacent sites on the target nucleic acid so that free probe is ligated to the probe particle. Excess free probe (i.e., nonligated), and target nucleic acid are removed from the reaction chamber (e.g., by washing), and the ligated probes are identified by the association of free probe label with the particles, and the probes complexed to the particles are identified by the physical property of the particle. In a preferred embodiment, after removing excess probe and the target, the particles move single file through a channel from the reaction chamber to the detecting device (s). As single particles move past the detecting device(s) they measure free probe label covalently attached to the particles, and the physical property of the particle. In an alternative preferred embodiment, before or after removing excess probe and the target, the particles are fractionated, for example, by size (e.g., exclusion chromatography), charge (e.g., ion exchange chromatography), and/or density/weight into their sets using the physical property. These fractionated particles are assayed by the detecting device(s).

In a preferred embodiment, there is a set of second reaction chambers in the apparatus, and the pool of probe-particles are placed in the second reaction chamber. Target and buffer are mixed in the reagent chamber and these are fed into the first reaction chamber which contains the labeled free probe. The probe and target are mixed, and optionally the probe may hybridize to the target. This mixture of labeled probe and target is then passed to the second reaction chamber which contains the pool of probe-particles. The free probe and probe-particles hybridize to target and appropriate probes are ligated in the second reaction chamber. The ligating agent may be added at the reagent chamber or in either reaction chamber, preferably, the ligating agent is added in the second reaction chamber. The probe-particle hybridization products in the second reaction chamber are analyzed as above.

In one embodiment, the target nucleic acid is not amplified prior to analysis (either by PCR or in a vector, e.g., a lambda library). Preferably longer free and particle probes are used in this embodiment because of the increase in sequence complexity of the sample (i.e., to distinguish positives over background).

The probe-particle embodiments described in this example are suitable for use in any of the applications previously described, including, but not limited to the previously described diagnostic and sequencing applications. Additionally, these probe particle embodiments may be modified by any the previously described variations or modifications.

EXAMPLE 37

The Interaction of Complementary Polynucleotides in the Presence of Agents which Modify the Binding Between the Polynucleotides In this embodiment, the discrimination of perfect matches from mismatches in the binding of complementary polynucleotides is modulated by the addition of an agent or agents. In a preferred embodiment, the complementary polynucleotides are a target polynucleotide and a polynucleotide probe. The discrimination of perfect matches from mismatches may be modulated by adding an agent wherein the agent is a salt such as tetraalkyl ammonium salt (e.g., TMAC, Ricelli et al., Nucl. Acids Res. 21:3785–3788 (1993)), sodium chloride, phosphate salts, and borate salts, organic solvents such as formamide, glycol, dimethylsulfoxide, and dimethylformamide, urea, guanidinium, amino acid analogs such as betaine (Henke et al., Nucl. Acids Res. 19:3957–3958 (1997); Rees et al., Biochemistry 32:137–144 (1993)), polyamines such as spermidine and spermine (Thomas et al., Nucl. Acids Res. 25:2396–2402 (1997)), or other positively charged molecules which neutralize the negative charge of the phosphate backbone, detergents such as sodium dodecyl sulfate, and sodium lauryl sarcosinate, minor/major groove binding agents, positively charged polypeptides, and intercalating agents such as acridine, ethidium bromide, and anthracine. In a preferred embodiment, a mixture of agents is added to the hybridization reaction to modulate the discrimination of perfect matches from mismatches. Some of these agents effect discrimination by reducing the entropy of melting between two complementary strands.

In a preferred embodiment, the discrimination of perfect matches from mismatches is improved by the agent or agents. For example, formamide, a commonly used denaturing agent, has been shown to preferentially destabilize mismatches versus perfect matches in a format III reaction. As described above, a format III reaction was set up, and then varying amounts of formamide were added (0%, 10%, 20%, 30%, 40%, and 50%). At 0% a perfect match signal was detected and the background (mismatches) was high. At 10% formamide, there was a good perfect match signal and the background/mismatch signal was reduced. At 20% formamide, the perfect match signal was reduced (but detectable) and the background/mismatch signal was eliminated. At 30%–50% formamide there was no perfect match or background/mismatch signal.

In an alternative embodiment, an agent is used to reduce or increase the $T_m$ of a pair of complementary polynucleotides. In a more preferred embodiment, a mixture of the agents is used to reduce or increase the $T_m$ of a pair of complementary polynucleotides. The agents may alter the $T_m$ in a number of ways, two examples, which are not meant to limit the invention, are (1) agents which disrupt the hydrogen bonding between the bases of two complementary polynucleotides (Goodman, Proc. Nat'l Acad. Sci. 94:10493–10495 (1997); Moran et al., Proc. Nat'l Acad. Sci. 94:10506–10511 (1997); Nguyen et al., Nucl. Acids Res. 25:3059–3065 (1997)), and (2) agents which neutralize or shield the negative charges of the phosphates in the sugar phosphate backbone of the polynucleotide (Thomas et al., Nucl. Acids Res. 25:2396–2402 (1997)). By strengthening or weakening (1) and/or (2) one can modulate the $T_m$ of a complementary pair of polynucleotides.

In a preferred embodiment, the formation of complexes between the probe and target nucleic acid is inhibited by the addition of an agent. For example, the formation of ligation products in a format III type reaction was eliminated by the addition of an alkyl polysulphonic acid. When 0.1–1.0% polyanethole sulfonic acid (or polyanethole sulfonate) was added the signal was eliminated.

In a most preferred embodiment, an agent or agents are added to decrease the binding energy of GC base pairs, or increase the binding energy of AT base pairs, or both. In a preferred embodiment, the agent or agents are added so that the binding energy from an AT base pair is approximately equivalent to the binding energy of a GC base pair. Thus, the energy of binding between two complementary polynucleotides is solely dependent on length. The energy of binding of these complementary polynucleotides may be increased by adding an agent that neutralizes or shields the negative charges of the phosphate groups in the polynucleotide backbone.

EXAMPLE 38
Enhancing the Activity of a Nucleic Acid Modifying Polypeptide

In one embodiment, the discrimination of perfect matches from mismatches is enhanced in a format III reaction. The discrimination is enhanced by an agent selected from the group comprising a polyamine such as spermidine or spermine, other positively charged molecules which neutralize the negative charge of the phosphate backbone, and a $Mg^{++}$ ion. The discrimination is also enhanced by changing a physical condition selected from the group comprising temperature, reaction time, or ionic strength. In a most preferred embodiment, several agents are added and several physical conditions are changed. For example, the discrimination of perfect matches from mismatches was increased about 10–100 fold by adding or altering the following agents and physical conditions: 100 mM $MgCl_2$ (increase from 10 mM $MgCl_2$), 100 mM dithiothrietol, 100 $\mu$g/ml BSA (increase from 25 $\mu$g/ml), 10 mM ATP (increase from 1 mM), 10 mM spermadine, 10 units/$\mu$l ligase (increase from 4 units/$\mu$l), at room temperature (increase from 4° C.) for 30 minutes (decrease from 120 minutes). The $MgCl_2$, ATP, dithiothrietol, and BSA, act to stabilize the ligase during the reaction. The increased temperature and ligase concentration increase the rate at which ligation products are produced so that the reaction time can be decreased. These factors may also impact the ligation reaction through a kinetic effect. The $MgCl_2$, and the spermadine enhance discrimination by favoring the formation of perfect matches over mismatches (they preferentially increase the $\Delta G$ of formation for the perfect match over the mismatch). In addition, discrimination in a format III reaction was enhanced by the following agents: 20–100 mM $MgCl_2$ and 5–10 mM ATP, 10–100 mM dithiothrietol, 50–100 $\mu$g/ml BSA, or 5–20 mM spermadine. Other agents that maybe used to enhance discrimination include those recited supra. Discrimination was also enhanced by raising the temperature from 4° C. to 16–37° C., or increasing the ligase concentration to 5–20 units/$\mu$l.

In an alternative embodiment, the activity of a polynucleic acid polymerase is enhanced by the agents which enhance the discrimination of perfect matches and mismatches between a target nucleic acid and a complementary polynucleotide. The reaction mixture for the polymerase includes a target nucleic acid, a polynucleotide primer and an agent(s) which enhances the discrimination of the perfect matches from the mismatches. The polynucleic acid polymerase reacts with the primer to replicate the target nucleic acid and correct (perfect match) priming is favored over mismatch priming by the agent. The agent(s) may include a salt such as tetraalkyl ammonium salt (e.g., TMAC, Ricelli et al., Nucl. Acids Res. 21:3785–3788 (1993)), sodium chloride, phosphate salts, and borate salts, organic solvents such as formamide, glycol, dimethylsulfoxide, and dimethylformamide, urea, guanidinium, amino acid analogs such as betaine (Henke et al., Nucl. Acids Res. 19:3957–3958 (1997); Rees et al., Biochemistry 32:137–144 (1993)), polyamines such as spermidine and spermine (Thomas et al., Nucl. Acids Res. 25:2396–2402 (1997)), or other positively charged molecules which neutralize the negative charge of the phosphate backbone, detergents such as sodium dodecyl sulfate, and sodium lauryl sarcosinate, minor/major groove binding agents, positively charged polypeptides, and intercalating agents such as acridine, ethidium bromide, and anthracine. In a preferred embodiment, a mixture of agents is added to the hybridization reaction to modulate the discrimination of perfect matches from mismatches. In a most preferred embodiment, the agent(s) is used to enhance proper priming in a PCR reaction. For example, when 10 mM spermadine is added to a PCR reaction there was at least a 5-fold increase in product.

In still another alternative embodiment, the activity of polypeptide which modifies a nucleic acid, such as, for example, an integrase, a gyrase, a nuclease, a helicase, a methylase, and a capping enzyme, is enhanced by the agents which enhance the discrimination of perfect matches and mismatches between a target nucleic acid and a complementary polynucleotide. The reaction mixture for the polypeptide includes a target nucleic acid, a complementary polynucleotide and an agent(s) which enhances the discrimination of the perfect matches from the mismatches. The polypeptide reacts with the complex of the polynucleotide and the target nucleic acid and the perfect match complexes are favored over mismatch complexes by the agent. Agents that maybe used to enhance discrimination include those recited supra.

EXAMPLE 39
Enhancing the Discrimination of Perfect Matches from Mismatches Using a Modified Ligase The invention relates to modified DNA ligases which increase the discrimination of perfect matches from mismatches for complementary polynucleotides. The modified ligase enhances discrimination in a number of ways, for example, the ligase may increase the difference in the on rates and/or the off rates between a perfect match product and a mismatch product (a kinetic effect); or the ligase may increase the binding energy difference between a perfect match and a mismatch (a free energy [$\Delta G$] effect); or the ligase may itself discriminate between perfect matches and mismatches ($\Delta G$ or kinetic effect); or some combination of these and other factors.

39.1 Modified Ligases

The modified ligase of the invention may be prepared by methods well known in the art for modifiying polypeptides, such as are found in for e.g., Current Protocols in Protein Science (1997) J. E Coligan, et al., eds. John Wiley & Sons, New York; and Kaiser E T, Lawrence D S, Rokita S E. (1985) "The chemical modification of enzymatic specificity." Annu Rev Biochem, 54:565–595.

The ligases of the invention may also be modified by producing variants of the ligase nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the ligase nucleic acids are preferably constructed by mutating the polynucleotide to give an amino acid sequence that does not occur in nature.

These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the ligase nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487–6500 (1982).

PCR may also be used to create amino acid sequence variants of the ligase nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the ligase at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al.

39.2 Recombinant Expression of the Modified Ligase.

The present invention further provides recombinant constructs comprising a modified ligase nucleic acid. The recombinant constructs of the present invention comprise a vector, such as a plasmid or viral vector, into which a modified ligase nucleic acid is inserted, in a forward or reverse orientation. The vector may further comprise regulatory sequences, including for example, a promoter, operably linked to the ORF. The vector may further comprise a marker sequence or heterologous ORF operably linked to an expression modulating fragment ("EMF") or uptake modulating fragment ("UMF"). Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Generally, recombinant expression vectors will include origins of replication and selectable markers permitting transformation of the host cell, e.g., the ampicillin resistance gene of *E.coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting the modified ligase nucleic acid together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Any host/vector system can be used to express the modified ligases of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the modified ligase or which expresses the modified ligase at a low natural level.

The modified ligase can be expressed in mammalian cells, yeast, bacteria, or other cells under the control of appropriate promoters. Cell-free translation systems can also be employed to produce the modified ligase using RNAs derived from the DNA constructs of the present invention. Appropriate cloning and expression vectors for use with prokaryotic and eukaryotic hosts are described by Sambrook, et al., in *Molecular Cloning: A Laboratory Manual,* Second Edition, Cold Spring Harbor, N.Y. (1989), the disclosure of which is hereby incorporated by reference.

Various mammalian cell culture systems can also be employed to express the modified ligase. Examples of mammalian expression systems include the COS-7 lines of monkey kidney fibroblasts, described by Gluznan, *Cell* 23:175 (1981), and other cell lines capable of expressing a compatible vector, for example, the C127, 3T3, CHO, HeLa and BHK cell tines. Mammalian expression vectors will comprise an origin of replication, a suitable promoter and, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant modified ligase produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A variety of methodologies known in the art can be utilized to obtain the modified ligase of the present invention. At the simplest level, the amino acid sequence can be synthesized using commercially available peptide synthesizers. This is particularly useful in producing small peptides and fragments of larger polypeptides. Fragments are useful, for example, in generating antibodies against the modified ligase. In an alternative method, the modified ligase is purified from bacterial cells which produce the modified ligase. One skilled in the art can readily follow known methods for isolating polypeptides and proteins in order to purify the modified ligase of the present invention. These include, but are not limited to, immunochromatography, HPLC, size-exclusion chromatography, ion-exchange chromatography, and immuno-affinity chromatography. See, e.g., Scopes, *Protein Purification: Principles and Practice,* Springer-Verlag (1994); Sambrook, et al., in *Molecular Cloning: A Laboratory Manual;* Ausubel et al., *Current Protocols in Molecular Biology.*

The modified ligase of the present invention can alternatively be purified from cells which have been altered to express the modified ligase. As used herein, a cell is said to be altered to express the modified ligase when the cell, through genetic manipulation, is made to produce the modified ligase which it normally does not produce or which the cell normally produces at a lower level. One skilled in the art can readily adapt procedures for introducing and expressing either recombinant or synthetic sequences into eukaryotic or prokaryotic cells in order to generate a cell which produces the modified ligase of the present invention.

39.3 Modified Ligases Which Enhance Discrimination.

In one embodiment, the discrimination of perfect matches from mismatches is enhanced in a format III reaction. In the format III reaction, the target nucleic acid interacts with complementary probes and the discrimination of perfect matches from mismatches is enhanced by the modified ligase. The modified ligase enhances discrimination in a number of ways, for example, the ligase may increase the difference in the on rates and/or the off rates between a perfect match product and a mismatch product (a kinetic effect—e.g., the ligase may preferentially bind to perfect matches and slow the off-rate of perfect matches versus mismatches); or the ligase may increase the binding energy difference between a perfect match and a mismatch (a free energy [$\Delta G$] effect—e.g., the ligase may preferentially bind to perfect matches and increase the stability of perfect matches versus mismatches); or the ligase may itself discriminate between perfect matches and mismatches ($\Delta G$ or kinetic effect—e.g., the modified ligase may ligate only perfect matches); or some combination of these and other factors.

EXAMPLE 40

Preparation and Use of Nucleic Acid Pools Based on Representation in a Sample

Nucleic acids from a sample are pooled for hybridization studies to allow hybridization conditions to be adjusted to increase the likelihood that hybridization to the nucleic acids within each pool is within the linear range of detection. Pooling for this purpose is generally carried out by combining nucleic acids having similar degrees of representation in a sample into a pool. Suitable nucleic acids include genomic DNA, DNA produced by amplification, cDNA, and RNA. Methods for obtaining nucleic acids from samples are well-known (see, e.g., Sambrook et al. (1989), Supra, at 9.14–9.23) and exemplary methods are described in Example 20.

The degrees of representation of nucleic acids in a sample can be determined by any convenient method, such as large-scale EST (expressed sequence tag) analysis, differential display, Southern or Northern hybridization, and cDNA microarray hybridization. For complex samples, SBH can be used to cluster nucleic acids into groups having the same or similar nucleotide sequences. For a cDNA library containing $10^7$ million clones, SBH can be carried out using 100–500 (preferably 300) 5–10-mer (preferably 6–8-mer, more preferably 7-mer) oligonucleotide probes. Conveniently, SBH Format 1 is employed, i.e., nucleic acids are arrayed on a substrate and hybridized with a soluble, labeled probe.

Nucleic acids can be fragmented and denatured as described in Example 7 and one or more arrays can be produced as described in Example 8. Oligonucleotide probes are labeled with a detectable label, such as, for example, a radiolabel (as discussed in Example 10) a fluorescent label, a chemiluminescent label, an enzyme label, an electrophore mass label, or a particle label. Particle labels are described in Example 36 and include, for example, nanoparticles imprinted with a detectable code (e.g., "bar-coded nanoprobes"). Hybridization is carried out according to the principles discussed in Examples 9 and 10. The array(s) is (are) washed to remove unhybridized label. Suitable washing conditions depend on the length of the hybrids and can readily be determined by those skilled in the art. Exemplary conditions are discussed in Example 10. After washing, hybridization can be detected, for example, as discussed in Examples 9 and 15 (radio- and fluorescent labeling).

For each clone, the bound oligonucleotide probes are identified. The panel of bound probes defines a signature.

Signatures can be determined based on perfectly matched probes (i.e., those that are 100% complementary to the sequences they bind). In general, however, the signatures also include probes having a slight mismatch (e.g., a single base mismatch for a 7-mer probe). Slightly mismatched probes generally produce a hybridization signal of at least about 90% the intensity of that observed with perfectly matched probes.

Nucleic acids sharing a common signature are expected to have the same or similar nucleotide sequences and are therefore clustered into a group. For example, a half million clones from a cDNA library, as discussed above, can be conveniently analyzed and clustered to yield on the order of 20,000 groups. A representative clone is selected from each group. The number of clones in each group is noted as an indication of the degree of representation of each selected clone in the original cDNA library. The representative clones are then divided into pools based on degree of representation.

The number of pools produced and the cut-off points between the pools depend on the distribution of degrees of representation of the nucleic acids to be pooled. If degree of representation is determined by clustering, as discussed above, this distribution is obtained by plotting the group size (i.e., number of clones/group) on the x-axis versus the number of groups of that size on the y-axis. The object is to pool those nucleic acids having similar degrees of representation. In particular, the degrees of representation of the nucleic acids in each pool should be sufficiently similar to allow the selection of hybridization conditions wherein hybridization is linear for substantially all of the nucleic acids in the pool.

For a typical cDNA library, e.g., one generated from bone marrow, the production of three pools corresponding to low, intermediate, and high representation sequences, provides significant enhancements in the ability to identify and characterize hybridizing nucleic acid sequences. If, for example, 20,000 representative clones are selected and the number of high, intermediate, and low representation clones is roughly equal, three pools of approximately 6,000–7,000 clones each can be produced, provided the degrees of representation of the clones in each pool are sufficiently similar to allow linear hybridization.

If the initial pooling does not yield pools of nucleic acids having sufficiently similar degrees of representation to allow linear hybridization, one or more of the initial pools can be further subdivided. Thus, if in the above example, linear hybridization could not be achieved for the high representation pool of clones by adjusting hybridization conditions, that pool would be sub-divided into "high" and "very high" representation pools according to the principles discussed above. The final set of pools would include the 6,000–7, 000-clone low and intermediate representation pools and the smaller pools containing the high and very high representation clones.

Once the pools are produced, the nucleic acids in each pool can be contacted with one or more target nucleic acids and/or oligonucleotide probes (labeled as described above) under conditions suitable for hybridization. Different hybridization conditions are used for each pool, with the hybridization conditions for each pool designed to help ensure that hybridization remains within the linear range. More specifically, hybridization conditions are selected based on the degree of representation of the pooled nucleic acids in the sample from which they were derived. Where the sample is a cDNA library, the hybridization conditions for each pool are a function of the representation of the pooled clones in the cDNA library, which in turn reflects the abundance or expression level of the corresponding mRNAs.

For low representation pools, the hybridization conditions are selected to produce a relatively high yield of hybrids, thereby boosting the hybridization signal. For example, the hybridization time can be increased or the association rate can be increased. Factors affecting the association rate are well known and include nucleic acid concentrations, nucleic acid lengths, base composition, ionic strength, viscosity, denaturing agents (e.g., formamide), polymers (e.g., dextran sulfate), detergents (e.g., Sarcosyl), mismatching, temperature, and pH. See, e.g., Hames, B. D., and Higgins, S. J. (eds.) *Nucleic Acid Hybridisation: A Practical Approach* (IRL Press 1990) (hereafter *Nucleic Acid Hybridisation*), which is hereby incorporated by reference in its entirety. See also Example 10 (discussing hybridization conditions that ensure discrimination between matched and mismatched oligonucleotide-target DNA hybrids). For high representation pools, the hybridization conditions are selected so that the pooled nucleic acids do not become saturated during hybridization. Intermediate representation nucleic acid pools are hybridized for a time in between the hybridization times of the high and low representation pools and/or other conditions are adjusted to produce an association rate in between that for the high and low representation pools.

The conditions selected depend on whether hybridization is carried out in solution or with one nucleic acid strand in the hybridizing pairs affixed to a substrate, such as a nitrocellulose filter. See *Nucleic Acid Hybridisation*, Supra. The determination of suitable hybridization conditions for a given pool of nucleic acids derived as described above is well within the level of skill in the art. Pools of cDNA clones, for example, derived as discussed above can be arrayed on a substrate, such as a nitrocellulose filter or chip, and then hybridized under standard conditions (see, e.g., Example 10, for instance) for 10 minutes, 1 hour, and overnight (e.g., 18 hours) for the high, intermediate, and low representation pools, respectively. If non-linear hybridization is observed, the study can be repeated under modified conditions until linearity is achieved.

Hybridization can be carried out in any of a variety of formats. Pooled nucleic acids can conveniently be affixed to one or more substrates and hybridized with soluble target nucleic acid(s) and/or oligonucleotide probe(s) (i.e., SBH Format 1). Alternatively, target nucleic acid(s) and/or oligonucleotide probe(s) can be affixed to one or more substrates and hybridized with the pooled nucleic acids (i.e., SBH Format 2). Pooled nucleic acids can also employed in SBH Format 3 hybridization studies, in which target nucleic acids are hybridized to substrate-affixed pooled nucleic acids and to a set of soluble oligonucleotide probes. In another format, both the pooled nucleic acids and the target nucleic acid(s) and/or oligonucleotide probe(s) are in solution.

When the pooled nucleic acids are affixed to a substrate, each nucleic acid pool is conveniently arrayed on a substrate in a separate array to facilitate the use of different hybridization conditions for each pool. The nucleic acid pools arrays can be on the same substrate or different substrates. If the nucleic acid pools are arrayed on the same substrate, the pools are separated by a physical barrier that allows the pools to be subjected to different hybridization times, temperatures, and/or buffers. For example, a hydrophobic material can be used to separate arrays and prevent the mixing of different hybridization buffers.

The nucleic acids can also be affixed to one or more substrates in one or more arrays including nucleic acids from different pools. The problem of non-linear hybridization in arrays containing, e.g., high, medium, and low representation nucleic acids, can be avoided by conducting multiple parallel hybridizations. More specifically, the nucleic acids are arrayed such that, for each dot in the array, the corresponding pool is known, and thus the degree of representation of the nucleic acid in the dot is known. Sets of hybridization conditions are selected to facilitate linear hybridization with the nucleic acids of a each pool (i.e., one set of hybridization conditions/pool). An identical array is prepared for each set of hybridization conditions to be employed, and the arrays are hybridized to target nucleic acids and/or oligonucleotide probes. For each array, hybridization at all dots corresponding to a single pool is then determined. Thus, if "array 1" was hybridized under conditions that facilitated linear hybridization of "pool 1" nucleic acids, array 1 would be analyzed to determine hybridization at dots corresponding to pool 1. Analysis of all arrays allows the analysis of the nucleic acids in all pools.

Pooled nucleic acids can also be analyzed in studies in which hybridization is carried out in solution. Such studies require the use of at least two types of labels, at least one of which identifies the specific nucleic acid to which the label is attached. When nucleic acids are arrayed on a substrate, the identity of the nucleic acid is "encoded" in its location in the array. However, in solution hybridization, the identities of the nucleic acids are encoded in the attached labels. Thus, different labels identify different nucleic acids from different pools. A separate hybridization reaction can be carried out for each pool under conditions suitable for hybridization of that pool. The hybridization signals for the labeled nucleic acids corresponding to that pool can then be scored.

A wide variety of labels and detection systems are available, and the selection of appropriate labels and detection system for use in hybridization studies employing the nucleic acid pools of this embodiment is within the level of skill in the art. Pooled nucleic acids and/or target nucleic acids or oligonucleotide probes can be labeled with any of the detectable labels discussed above and in Examples 10, 30, and 36. Labels and detection systems useful in hybridization studies employing multiple labels (i.e., "label multiplexing") are as described in Example 30 (radioisotopes, fluorescent labels, electrophore mass labels) and/or Example 36 (particles). In complex formats, for example those employing nucleic acids labeled with one set of distinct identifying labels and target nucleic acids or oligonucleotide probes labeled with a second set of distinct identifying labels, electrophore mass labels and particle labels, such as "bar-coded" nanoprobes, provide the necessary discrimination among sequences to allow identification of the hybrids produced in solution hybridization. Regardless of the label-detection system employed, standard procedures are followed to ensure that the detection conditions allow determination of hybridization within the linear range of detection.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

What is claimed is:

1. A method for preparing a plurality of nucleic acid pools comprising:

(a) providing a sample of nucleic acids;

(b) contacting each nucleic acid with each of a plurality of oligonucleotide probes under conditions for hybridization of oligonucleotide probes to nucleic acids;

(c) identifying nucleic acids that hybridize to the same plurality of oligonucleotide probes thereby clustering the nucleic acids in a plurality of groups, wherein each group comprises nucleic acids having tht same or similar nucleotide sequences;

(d) determining the number of nucleic acids in each group as an indication of the degree of representation in the sample of the nucleic acids within said group;

(e) selecting a single nucleic acid from each group to obtain a series of representative nucleic acids;

(f) combining different representative nucleic acids in a plurality of pools based on degree of representation in the sample, wherein the degree of representation of a representative nucleic acid in each pool is sufficiently similar to other different representative nucleic acids in that pool to allow one set of hybridization conditions to be selected for that pool that is suitable for all nucleic acids in that pool.

2. The method of claim 1 additionally comprising affixing said representative nucleic acids to one or more substrates.

3. The method of claim 2 wherein each pool of representative nucleic acids is arrayed on a substrate to form a plurality of arrayed pools of representative nucleic acids on said on said substrate.

4. A method for preparing a plurality of nucleic acid arrays comprising:

(a) providing a series of different nucleic acids derived from a sample;

(b) subdividing said series of nucleic acids into a plurality of pools based on degree of representation in the sample, wherein the degree of representation of a nucleic acid in each pool is sufficienty similar to other different nucleic acids in that pool to allow one set of hybridization conditions to be selected for that pool that is suitable for all nucleic acids in that pool;

(c) affixing each pool of nucleic acids to a substrate to form a plurality of arrays of nucleic acids.

5. An array of pools of different nucleic acids affixed to a substrate, wherein the nucleic acids in each pool have a degree of representation in the sample that is within a predetermined range allowing selection of one set of hybridization conditions that is suitable for all nucleic acids in that pool.

6. A kit comprising a plurality of arrays of different nucleic acids affixed to one or more substrates, wherein the nucleic acids are derived from a sample, and wherein the nucleic acids in each array have a degree of representation in the sample that is within a predetermined range, said range being different for each array and said range for each array allowing one set of hybridization conditions to be selected for that array that is suitable for all nucleic acids in that array.

7. An improved method for determining the presence or representation of a nucleic acid sequence in a sample comprising:

(a) providing a series of different nucleic acids derived from a sample, wherein said series has been subdivided in a plurality of pools based on degree of representation in the sample;

(b) contacting the nucleic acids in each pool with one or more target nucleic acids and/or oligonucleotide probes under conditions suitable for hybridization, wherein said suitable hybridization conditions are different for each pool, wherein the degree of representation of a nucleic acid in each pool is sufficiently similar to other different representative nucleic acids in that pool to allow one set of hybridization conditions to be selected for that pool that is suitable for all nucleic acids in that pool; and (c) detecting hybridization between said nucleic acids and said one or more targets nucleic acids and/or probes as an indication of the presence or representation of one or more nucleic acid sequences in said sample.

8. The method of claim 7 wherein said nucleic acids are affixed to one or more substrates.

9. The method of claim 8 wherein each pool of representative nucleic acids is arrayed on a substrate to form a plurality of arrays of nucleic acids.

10. The method of claim 7 wherein each nucleic acid is labeled and is contacted with one or more target nucleic acids and or oligonucleotide probes in solution.

* * * * *

UNITED STATES PATENT AND TRADEMARK OFFICE
CERTIFICATE OF CORRECTION

PATENT NO.   : 6,355,419 B1
DATED        : March 12, 2002
INVENTOR(S)  : Alfenito Page 1 of 1

It is certified that error appears in the above-identified patent and that said Letters Patent is hereby corrected as shown below:

<u>Column 85,</u>
Line 30, replace "having tht same", with -- having the same --.

Signed and Sealed this

Fourth Day of March, 2003

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Exemplary
      nucleotide hybridization sequence used in sequence
      assembly process.

<400> SEQUENCE: 1
aaaaaatttt tt                                                                12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Exemplary
      nucleotide hybridization sequence used in sequence
      assembly process.

<400> SEQUENCE: 2
aaaaattttt ta                                                                12

```
<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 3
aaaaattttt t                                                              11

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 4
aaaaattttt tc                                                             12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 5
aaaaattttt tg                                                             12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 6
taaaaatttt tt                                                             12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 7
caaaaatttt tt                                                             12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:  Exemplary
      nucleotide hybridization used in sequence assembly
      process.
```

```
<400> SEQUENCE: 8
gaaaaatttt tt                                                                                    12

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence:  Exemplary
      nucleotide hybridization sequence used in sequence
      assembly process.

<400> SEQUENCE: 9
aaaaaatttt t                                                                                     11
```